(12) United States Patent
Carter et al.

(10) Patent No.: US 7,687,508 B2
(45) Date of Patent: *Mar. 30, 2010

(54) CYCLIC DERIVATIVES AS MODULATORS OF CHEMOKINE RECEPTOR ACTIVITY

(75) Inventors: Percy H. Carter, Princeton, NJ (US); Robert J. Cherney, Newtown, PA (US); John Hynes, Washington Crossing, PA (US); Soo S. Ko, Hockessin, DE (US); Anurag S. Srivastava, Belle Mead, NJ (US); Zili Xiao, West Windsor, NJ (US); Michael G. Yang, Narbeth, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/782,810

(22) Filed: Jul. 25, 2007

(65) Prior Publication Data

US 2008/0027080 A1    Jan. 31, 2008

Related U.S. Application Data

(60) Provisional application No. 60/834,235, filed on Jul. 28, 2006, provisional application No. 60/896,026, filed on Mar. 21, 2007.

(51) Int. Cl.
*A61K 31/517* (2006.01)
*C07D 401/12* (2006.01)
*A61K 31/501* (2006.01)
*A61K 31/5025* (2006.01)
*A61K 31/519* (2006.01)
*C07D 403/12* (2006.01)
*C07D 413/12* (2006.01)
*C07D 417/12* (2006.01)
*C07D 419/12* (2006.01)
*C07D 239/36* (2006.01)

(52) U.S. Cl. .............. 514/266.2; 544/293; 544/335; 544/256; 514/343; 514/252.05; 514/262.1; 546/278.4

(58) Field of Classification Search .......... 544/284, 544/293; 514/362.1, 266.2
See application file for complete search history.

(56) References Cited

U.S. PATENT DOCUMENTS

| | | | |
|---|---|---|---|
| 6,706,712 | B2 | 3/2004 | Cherney |
| 6,974,836 | B2 | 12/2005 | Carter et al. |
| 7,087,604 | B2 | 8/2006 | Cherney |
| 7,157,470 | B2 | 1/2007 | Smallheer et al. |
| 7,163,937 | B2 * | 1/2007 | Carter et al. ........... 514/210.18 |
| 7,183,270 | B2 | 2/2007 | Cherney et al. |
| 7,230,133 | B2 | 6/2007 | Carter |
| 2003/0171218 | A1 | 9/2003 | Bojack et al. |
| 2004/0186143 | A1 | 9/2004 | Carter et al. |
| 2004/0235836 | A1 | 11/2004 | Cherney |
| 2005/0043392 | A1 | 2/2005 | Carter |
| 2005/0054626 | A1 | 3/2005 | Carter et al. |
| 2005/0054627 | A1 | 3/2005 | Carter et al. |
| 2005/0065147 | A1 | 3/2005 | Carter |
| 2006/0069123 | A1 | 3/2006 | Xia et al. |
| 2007/0197516 | A1 | 8/2007 | Carter |

FOREIGN PATENT DOCUMENTS

| | | |
|---|---|---|
| EP | 0 550 924 | 7/1993 |
| JP | 63-83082 | 4/1988 |
| WO | WO 97/05111 | 2/1997 |
| WO | WO 97/43257 | 11/1997 |
| WO | WO 98/01426 | 1/1998 |
| WO | WO 99/00362 | 1/1999 |
| WO | WO 99/07678 | 2/1999 |
| WO | WO 99/37304 | 7/1999 |
| WO | WO 99/38844 | 8/1999 |
| WO | WO 99/40914 | 8/1999 |
| WO | WO 99/46991 | 9/1999 |
| WO | WO 01/10799 | 2/2001 |
| WO | WO 01/17992 | 3/2001 |
| WO | WO 02/04416 | 1/2002 |
| WO | WO 02/060859 | 8/2002 |
| WO | WO 02/078679 | 10/2002 |
| WO | WO 02/102372 | 12/2002 |
| WO | WO 03/005824 | 1/2003 |
| WO | WO 03/075853 | 9/2003 |
| WO | WO 2004/022536 | 3/2004 |
| WO | WO 2004/071460 | 8/2004 |
| WO | WO 2004/098516 | 11/2004 |
| WO | WO 2004/110376 | 12/2004 |
| WO | WO 2005/021500 | 3/2005 |
| WO | WO 2006/013427 | 2/2006 |

OTHER PUBLICATIONS

Mascolini, et al. XVI Internat. AIDS Conf., Toronto, Canada, Aug. 2006.*
Lu, et al., Bioorg. Med. Chem. Lett. 17 (2007) 1883-1887.*
de Groot, et al., Arch. Dermatol. Res., Sep. 2007; 299(7): 305-313.*
Herfarth, et al., Immunol. Lett., 77 (2001), 113-117.*
Abbadie, C. et al., "Impaired neuropathic pain responses in mice lacking the chemokine receptor CCR2", Proceedings of the National Academy of Sciences, vol. 100, No. 13, pp. 7947-7952 (2003).

(Continued)

*Primary Examiner*—Mark L Berch
*Assistant Examiner*—Cecilia M Jaisle
(74) *Attorney, Agent, or Firm*—Terence J. Bogie; Laurelee A. Duncan

(57) ABSTRACT

This invention relates generally to modulators of chemokine receptor activity having unexpected combination of desirable pharmacological properties. Pharmaceutical compositions containing the same, and methods of using the same as agents for treatment and prevention of inflammatory, allergic, autoimmune, metabolic, cancer and/or cardiovascular diseases, particularly diabetes, Crohn's disease, atherosclerosis, and multiple sclerosis, along with methods of preparing compounds and intermediates therefor. Metabolites of active compounds are also provided herein, pharmaceutical compositions and use thereof are also provided.

11 Claims, 1 Drawing Sheet

OTHER PUBLICATIONS

Abdi, R. et al., "Differential Role of CCR2 in Islet and Heart Allograft Rejection: Tissue Specificity of Chemokine/Chemokine Receptor Function In Vivo", The Journal of Immunology, vol. 172, pp. 767-775 (2004).

Andres, P.G. et al., "Mice with a Selective Deletion of the CC Chemokine Receptors 5 or 2 are Protected from Dextran Sodium Sulfate-Mediated Colitis: Lack of CC Chemokine Receptor 5 Expression Results in a NK1.1+ Lymphocyte-Associated Th2-Type Immune Response in the Intestine", The Journal of Immunology, vol. 164, pp. 6303-6312 (2000).

Antoniades, H.N. et al., "Expression of monocyte chemoattractant protein 1 mRNA in human idiopathic pulmonary fibrosis", Proc. Natl. Acad. Sci. USA, vol. 89, pp. 5371-5375 (1992).

Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).

Belperio, J.A. et al., "Critical role for the chemokine MCP-1/CCR2 in the pathogenesis of bronchiolitis obliterans syndrome", The Journal of Clinical Investigation, vol. 108, No. 4, pp. 547-556 (2001).

Berman, J.W. et al., "Localization of Monocyte Chemoattractant Peptide-1 Expression in the Central Nervous System in Experimental Autoimmune Encephalomyelitis and Trauma in the Rat", The Journal of Immunology, vol. 156, pp. 3017-3023 (1996).

Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).

Boring, L. et al., "Decreased lesion formation in $CCR2^{-/-}$ mice reveals a role for chemokines in the initiation of atherosclerosis", Nature, vol. 394, pp. 894-897 (1998).

Boring, L. et al., "Impaired Monocyte Migration and Reduced Type 1 (Th1) Cytokine Responses in C-C Chemokine Receptor 2 Knockout Mice", The Journal of Clinical Investigation, vol. 100, No. 10, pp. 2552-2561 (1997).

Brodmerkel, C.M. et al., "Discovery and Pharmacological Characterization of a Novel Rodent-Active CCR2 Antagonist, INCB3344", The Journal of Immunology, vol. 175, pp. 5370-5378 (2005).

Brühl, H. et al., "Dual Role of CCR2 during Initiation and Progression of Collagen-Induced Arthritis: Evidence for Regulatory Activity of $CCR2^+$ T Cells", The Journal of Immunology, vol. 172, pp. 890-898 (2004).

Bruun, J.M. et al., "Monocyte Chemoattractant Protein-1 Release is Higher in Visceral than Subcutaneous Human Adipose Tissue (AT): Implication of Macrophages Resident in the AT", The Journal of Clinical Endocrinology & Metabolism, vol. 90, No. 4, pp. 2282-2289 (2005).

Bush, E. et al., "CC Chemokine Receptor 2 is Required for Macrophage Infiltration and Vascular Hypertrophy in Angiotensin II-Induced Hypertension", Hypertension, vol. 36, pp. 360-363 (2000).

Carter, P.H., "Chemokine receptor antagonism as an approach to anti-inflammatory therapy: 'just right' or plain wrong?", Current Opinion in Chemical Biology, vol. 6, pp. 510-525 (2002).

Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).

Charo, I.F. et al., "The Many Roles of Chemokines and Chemokine Receptors in Inflammation", The New England Journal of Medicine, vol. 354, No. 6, pp. 610-621 (2006).

Chen, A. et al., "Diet Induction of Monocyte Chemoattractant Protein-1 and its Impact on Obesity", Obesity Research, vol. 13, No. 8, pp. 1311-1320 (2005).

Chen, H., "Cellular inflammatory responses: Novel insights for obesity and insulin resistance", Pharmacological Research, vol. 53, pp. 469-477 (2006).

Chow, F.Y. et al., "Monocyte chemoattractant protein-1-induced tissue inflammation is critical for the development of renal injury but not type 2 diabetes in obese db/db mice", Diabetologia, vol. 50, pp. 471-480 (2007).

Cipollone, F. et al., "Elevated Circulating Levels of Monocyte Chemoattractant Protein-1 in Patients with Restenosis After Coronary Angioplasty", Arterioscler. Thromb. Vasc. Biol., vol. 21, pp. 327-334 (2001).

Combadiere, C. et al., "Cloning and Functional Expression of a Human Eosinophil CC Chemokine Receptor", The Journal of Biological Chemistry, vol. 270, No. 27, pp. 16491-16494 (1995).

Connor, R.I. et al., "Change in Coreceptor Use Correlates with Disease Progression in HIV-1-Infected Individuals", J. Exp. Med., vol. 185, No. 4, pp. 621-628 (1997).

Connor, S.J. et al., "CCR2 expressing $CD4^+$ lymphocytes are preferentially recruited to the ileum in Crohn's disease", Gut, vol. 53, pp. 1287-1294 (2004).

Conti, I. et al., "CCL2 (monocyte chemoattractant protein-1) and cancer", Seminars in Cancer Biology, vol. 14, pp. 149-154 (2004).

Costain, W.J. et al., "Modulatory effects of PLG and its peptidomimetics on haloperidol-induced catalepsy in rats", Peptides, vol. 20, pp. 761-767 (1999).

Craig, M.J. et al., "CCL2 (Monocyte Chemoattractant Protein-1) in cancer bone metastases", Cancer Metastasis Rev., vol. 25, pp. 611-619 (2006).

Dandona, P. et al., "A Rational Approach to Pathogenesis and Treatment of Type 2 Diabetes Mellitus, Insulin Resistance, Inflammation, and Atherosclerosis", The American Journal of Cardiology, vol. 90, No. 5A, pp. 27G-33G (2002).

Dawson, J. et al., "Targeting monocyte chemoattractant protein-1 signalling in disease", Expert Opin. Ther. Targets, vol. 7, No. 1, pp. 35-48 (2003).

Dawson, T.C. et al., "Absence of CC chemokine receptor-2 reduces atherosclerosis in apolipoprotein E-deficient mice", Atherosclerosis, vol. 143, pp. 205-211 (1999).

Deleuran, M. et al., "Localization of monocyte chemotactic and activating factor (MCAF/MCP-1) in psoriasis", Journal of Dermatological Science, vol. 13, pp. 228-236 (1996).

Dimitrijevic, O.B. et al., "Absence of the Chemokine Receptor CCR2 Protects Against Cerebral Ischemia/Reperfusion Injury in Mice", Stroke, Vol. 38, pp. 1345-1353 (2007).

Doranz, B.J. et al., "A Dual-Tropic Primary HIV-1 Isolate that Uses Fusin and the β-Chemokine Receptors CKR-5, CKR-3, and CKR-2b as Fusion Cofactors", Cell, vol. 85, pp. 1149-1158 (1996).

Dresser, G.K. et al., "Pharmacokinetic-Pharmacodynamic Consequences and Clinical Relevance of Cytochrome P450 3A4 Inhibition", Clin. Pharmacokinet., vol. 38, No. 1, pp. 41-57 (2000).

Eckel, R.H. et al., "The metabolic syndrome", The Lancet, vol. 365, pp. 1415-1428 (2005).

Egashira, K. et al., "Importance of Monocyte Chemoattractant Protein-1 Pathway in Neointimal Hyperplasia After Periarterial Injury in Mice and Monkeys", Circulation Research, vol. 90, pp. 1167-1172 (2002).

Evans, M.C. et al., "Synthesis and Dopamine Receptor Modulating Activity of Novel Peptidomimetics of L-Prolyl-L-leucyl-glycinamide Featuring α,α-Disubstituted Amino Acids", Journal of Medicinal Chemistry, vol. 42, No. 8, pp. 1441-1447 (1999).

Feria, M. et al., "The CCR2 receptor as a therapeutic target", Expert Opin. Ther. Patents, vol. 16, No. 1, pp. 49-57 (2006).

Ferreira, A.M. et al., "Diminished Induction of Skin Fibrosis in Mice with MCP-1 Deficiency", Journal of Investigative Dermatology, vol. 126, pp. 1900-1908 (2006).

Fife, B.T. et al., "CC Chemokine Receptor 2 is Critical for Induction of Experimental Autoimmune Encephalomyelitis", J. Exp. Med., vol. 192, No. 6, pp. 899-905 (2000).

Frangogiannis, N.G. et al., "Critical Role of Monocyte Chemoattractant Protein-1/CC Chemokine Ligand 2 in the Pathogenesis of Ischemic Cardiomyopathy", Circulation, vol. 115, pp. 584-592 (2007).

Gao, Z. et al., "Unraveling the Chemistry of Chemokine Receptor Ligands", Chemical Reviews, vol. 103, No. 9, pp. 3733-3752 (2003).

Gaupp, S. et al., "Experimental Autoimmune Encephalomyelitis (EAE) in $CCR24^{-/-}$ Mice", American Journal of Pathology, vol. 162, No. 1, pp. 139-150 (2003).

Gerhardt, C.C. et al., "Chemokines control fat accumulation and leptin secretion by cultured human adipocytes", Molecular and Cellular Endocrinology, vol. 175, pp. 81-92 (2001).

Gharaee-Kermani, M. et al., "CC-chemokine receptor 2 required for bleomycin-induced pulmonary fibrosis", Cytokine, vol. 24, pp. 266-276 (2003).

Giles, R. et al., "Can We Target the Chemokine Network for Cancer Therapeutics?", Current Cancer Drug Targets, vol. 6, No. 8, pp. 659-670 (2006).

Gillitzer, R. et al., "MCP-1 mRNA Expression in Basal Keratinocytes of Psoriatic Lesions", The Journal of Investigative Dermatology, vol. 101, No. 2, pp. 127-131 (1993).

Gong, J.-H. et al., "An Antagonist of Monocyte Chemoattractant Protein 1 (MCP-1) Inhibits Arthritis in the MRL-/pr Mouse Model", J. Exp. Med., vol. 186, No. 1, pp. 131-137 (1997).

Gonzalo, J.-A. et al., "The Coordinated Action of CC Chemokines in the Lung Orchestrates Allergic Inflammation and Airway Hyperresponsiveness", J. Exp. Med., vol. 188, No. 1, pp. 157-167 (1998).

Gosling, J. et al., "MCP-1 deficiency reduces susceptibility to atherosclerosis in mice that overexpress human apolipoprotein B", The Journal of Clinical Investigation, vol. 103, No. 6, pp. 773-778 (1999).

Grimm, M.C. et al., "Enhanced expression and production of monocyte chemoattractant protein-1 in inflammatory bowel disease mucosa", Journal of Leukocyte Biology, vol. 59, pp. 804-812 (1996).

Gu, L. et al., "Absence of Monocyte Chemoattractant Protein-1 Reduces Atherosclerosis in Low Density Lipoprotein Receptor-Deficient Mice", Molecular Cell, vol. 2, pp. 275-281 (1998).

Guo, J. et al., "Repopulation of Apolipoprotein E Knockout Mice with CCR2-Deficient Bone Marrow Progenitor Cells Does Not Inhibit Ongoing Atherosclerotic Lesion Development", Arterioscler. Thromb. Vasc. Biol., vol. 25, pp. 1014-1019 (2005).

Guo, J. et al., "Transplantation of Monocyte CC-Chemokine Receptor 2-Deficient Bone Marrow into ApoE3-Leiden Mice Inhibits Atherogenesis", Arterioscler. Thromb. Vasc. Biol., vol. 23, pp. 447-453 (2003).

Hasegawa, H. et al., "Antagonist of Monocyte Chemoattractant Protein 1 Ameliorates the Initiation and Progression of Lupus Nephritis and Renal Vasculitis in MRL/lpr Mice", Arthritis & Rheumatism, vol. 48, No. 9, pp. 2555-2566 (2003).

Hayashidani, S. et al., "Anti-Monocyte Chemoattractant Protein-1 Gene Therapy Attenuates Left Ventricular Remodeling and Failure After Experimental Myocardial Infarction", Circulation, vol. 108, pp. 2134-2140 (2003).

Horiguchi, K. et al., "Selective Chemokine and Receptor Gene Expressions in Allografts that Develop Transplant Vasculopathy", The Journal of Heart and Lung Transplantation, vol. 21, No. 10, pp. 1090-1100 (2002).

Horuk, R., "Molecular properties of the chemokine receptor family", Trends in Pharmacological Sciences, vol. 15, pp. 159-165 (1994).

Horvath, C. et al., "Targeting CCR2 or CD18 Inhibits Experimental In-Stent Restenosis in Primates: Inhibitory Potential Depends on Type of Injury and Leukocytes Targeted", Circulation Research, vol. 90, pp. 488-494 (2002).

Hughes, P.M. et al., "Monocyte Chemoattractant Protein-1 Deficiency is Protective in a Murine Stroke Model", Journal of Cerebral Blood Flow & Metabolism, vol. 22, No. 3, pp. 308-317 (2002).

Iarlori, C. et al., "Interferon β-1b modulates MCP-1 expression and production in relapsing-remitting multiple sclerosis", Journal of Neuroimmunology, vol. 123, pp. 170-179 (2002).

Ishibashi, M. et al., "Critical Role of Monocyte Chemoattractant Protein-1 Receptor CCR2 on Monocytes in Hypertension-Induced Vascular Inflammation and Remodeling", Circulation Research, vol. 94, pp. 1203-1210 (2004).

Izikson, L. et al., "Resistance to Experimental Autoimmune Encephalomyelitis in Mice Lacking the CC Chemokine Receptor (CCR)2", J. Exp. Med., vol. 192, No. 7, pp. 1075-1080 (2000).

Jones, M.L. et al., "Potential Role of Monocyte Chemoattractant Protein 1/JE in Monocyte/Macrophage-Dependent IgA Immune Complex Alveolitis in the Rat", The Journal of Immunology, vol. 149, No. 6, pp. 2147-2154 (1992).

Kamei, N. et al., "Overexpression of Monocyte Chemoattractant Protein-1 in Adipose Tissues Causes Macrophage Recruitment and Insulin Resistance", The Journal of Biological Chemistry, vol. 281, No. 36, pp. 26602-26614 (2006).

Kanda, H. et al., "MCP-1 contributes to macrophage infiltration into adipose tissue, insulin resistance, and hepatic steatosis in obesity", The Journal of Clinical Investigation, vol. 116, No. 6, pp. 1494-1505 (2006).

Karrer, S. et al., "The-2518 Promotor Polymorphism in the MCP-1 Gene is Associated with Systemic Sclerosis", The Journal of Investigative Dermatology, vol. 124, vol. 1, pp. 92-98 (2005).

Kennedy, K.J. et al., "Acute and relapsing experimental autoimmune encephalomyelitis are regulated by differential expression of the CC chemokines macrophage inflammatory protein-1α and monocyte chemotactic protein-1", Journal of Neuroimmunology, vol. 92, pp. 98-108 (1998).

Khan, W.I. et al., "Critical role of MCP-1 in the pathogenesis of experimental colitis in the context of immune and enterochromaffin cells", Am. J. Physiol. Gastrointest. Liver Physiol., vol. 291, pp. G803-G811 (2006).

Kim, J.S. et al., "Expression of monocyte chemoattractant protein-1 and macrophage inflammatory protein-1 after focal cerebral ischemia in the rat", Journal of Neuroimmunology, vol. 56, pp. 127-134 (1995).

Kim, W.J.H. et al., "MCP-1 deficiency is associated with reduced intimal hyperplasia after arterial injury", Biochemical and Biophysical Research Communications, vol. 310, pp. 936-942 (2003).

Kitagawa, K. et al., "Blockade of CCR2 Ameliorates Progressive Fibrosis in Kidney", American Journal of Pathology, vol. 165, No. 1, pp. 237-246 (2004).

Koch, a.E. et al., "Enhanced Production of Monocyte Chemoattractant Protein-1 in Rheumatoid Arthritis", The Journal of Clinical Investigation, vol. 90, pp. 772-779 (1992).

Kurihara, T. et al., "Defects in Macrophage Recruitment and Host Defense in Mice Lacking the CCR2 Chemokine Receptor", J. Exp. Med., vol. 186, No. 10, pp. 1757-1762 (1997).

Kuziel, W.A. et al., "Severe reduction in leukocyte adhesion and monocyte extravasation in mice deficient in CC chemokine receptor 2", Proc. Natl. Acad. Sci. USA, vol. 94, pp. 12053-12058 (1997).

Lee, I. et al., "Blocking the Monocyte Chemoattractant Protein-1/CCR2 Chemokine Pathway Induces Permanent Survival of Islet Allografts through a Programmed Death-1 Ligand-1-Dependent Mechanism", The Journal of Immunology, vol. 171, pp. 6929-6935 (2003).

Liu, T. et al., "Depletion of macrophages reduces axonal degeneration and hyperalgesia following nerve injury", Pain, vol. 86, pp. 25-32 (2000).

Lloyd, C.M. et al., "RANTES and Monocyte Chemoattractant Protein-1 (MCP-1) Play an Important Role in the Inflammatory Phase of Crescentic Nephritis, but Only MCP-1 is Involved in Crescent Formation and Interstitial Fibrosis", J. Exp. Med., vol. 185, No. 7, pp. 1371-1380 (1997).

Lu, B. et al., "Abnormalities in Monocyte Recruitment and Cytokine Expression in Monocyte Chemoattractant Protein 1-deficient Mice", J. Exp. Med., vol. 187, No. 4, pp. 601-608 (1998).

Lu, Y. et al., "CCR2 Expression Correlates with Prostate Cancer Progression", Journal of Cellular Biochemistry, vol. 101, pp. 676-685 (2007).

Lu, Y. et al., "Monocyte Chemotactic Protein-1 (MCP-1) Acts as a Paracrine and Autocrine Factor for Prostate Cancer Growth and Invasion", The Prostate, vol. 66, pp. 1311-1318 (2006).

Lu, Y. et al., "Monocyte Chemotactic Protein-1 Mediates Prostate Cancer-Induced Bone Resorption", Cancer Research, vol. 67, No. 8, pp. 3646-3653 (2007).

Lukacs, N.W. et al., "Differential Recruitment of Leukocyte Populations and Alteration of Airway Hyperreactivity by C-C Family Chemokines in Allergic Airway Inflammation", The Journal of Immunology, vol. 158, pp. 4398-4404 (1997).

Lumeng, C.N. et al., "Increased Inflammatory Properties of Adipose Tissue Macrophages Recruited During Diet-Induced Obesity", Diabetes, vol. 56, pp. 16-23 (2007).

Lumeng, C.N. et al., "Obesity induces a phenotypic switch in adipose tissue macrophage polarization", The Journal of Clinical Investigation, vol. 117, No. 1, pp. 175-184 (2007).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of *TER1*, a Chemokine Receptor-Like Gene Expressed by Lymphoid Tissues", The Journal of Immunology, vol. 157, pp. 2759-2763 (1996).

Neels, J.G. et al., "Inflamed fat: what starts the fire?", The Journal of Clinical Investigation, vol. 116, No. 1, pp. 33-35 (2006).

Neote, K. et al., "Molecular Cloning, Functional Expression, and Signaling Characteristics of a C-C Chemokine Receptor", Cell, vol. 72, pp. 415-425 (1993).

Ni, W. et al., "New Anti-Monocyte Chemoattractant Protein-1 Gene Therapy Attenuates Atherosclerosis in Apolipoprotein E-Knockout Mice", Circulation, vol. 103, pp. 2096-2101 (2001).

Nomura, S. et al., "Significance of chemokines and activated platelets in patients with diabetes", Clinical and Experimental Immunology, vol. 121, pp. 437-443 (2000).

Ogata, H. et al., "The Role of Monocyte Chemoattractant Protein-1 (MCP-1) in the Pathogenesis of Collagen-Induced Arthritis in Rats", Journal of Pathology, vol. 182, pp. 106-114 (1997).

Okuma, T. et al., "C-C chemokine receptor 2 (CCR2) deficiency improves bleomycin-induced pulmonary fibrosis by attenuation of both macrophage infiltration and production of macrophage-derived matrix metalloproteinases", Journal of Pathology, vol. 204, pp. 594-604 (2004).

Pérez de Lema, G. et al., "Chemokine Receptor Ccr2 Deficiency Reduces Renal Disease and Prolongs Survival in MRL/Ipr Lupus-Prone Mice", Journal of the American Society of Nephrology, vol. 16, pp. 3592-3601 (2005).

Pickup, J.C. et al., "Is Type II diabetes mellitus a disease of the innate immune system?", Diabetologia, vol. 41, pp. 1241-1248 (1998).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Quinones, M.P. et al., "CC chemokine receptor (CCR)-2 prevents arthritis development following infection by *Mycobacterium avium*", J. Mol. Med., vol. 84, pp. 503-512 (2006).

Quinones, M.P. et al., "Experimental arthritis in CC chemokine receptor 2-null mice closely mimics severe human rheumatoid arthritis", The Journal of Clinical Investigation, vol. 113, No. 6, pp. 856-866 (2004).

Reinecker, H.-C. et al., "Monocyte-Chemoattractant Protein 1 Gene Expression in Intestinal Epithelial Cells and Inflammatory Bowel Disease Mucosa", Gastroenterology, vol. 108, No. 1, pp. 40-50 (1995).

Reynaud-Gaubert, M. et al., "Upregulation of Chemokines in Bronchoalveolar Lavage Fluid as a Predictive Marker of Post-Transplant Airway Obliteration", The Journal of Heart and Lung Transplantation, vol. 21, No. 7, pp. 721-730 (2002).

Rezaie-Majd, A. et al., "Simvastatin Reduces Expression of Cytokines Interleukin-6, Interleukin-8, and Monocyte Chemoattractant Protein-1 in Circulating Monocytes from Hypercholesterolemic Patients", Arterioscler. Thromb. Vasc. Biol., vol. 22, pp. 1194-1199 (2002).

Rollins, B.J., "Chemokines", Blood, vol. 90, No. 3, pp. 909-928 (1997).

Roque, M. et al., "CCR2 Deficiency Decreases Intimal Hyperplasia After Arterial Injury", Arterioscler. Thromb. Vasc. Biol., vol. 22, pp. 554-559 (2002).

Russell, M.E. et al., "Early and persistent induction of monocyte chemoattractant protein 1 in rat cardiac allografts", Proc. Natl. Acad. Sci. USA, vol. 90, pp. 6086-6090 (1993).

Saiura, A. et al., "Antimonocyte Chemoattractant Protein-1 Gene Therapy Attenuates Graft Vasculopathy", Arterioscler. Thromb. Vasc. Biol., vol. 24, pp. 1886-1890 (2004).

Salcedo, R. et al., "Human endothelial cells express CCR2 and respond to MCP-1: direct role of MCP-1 in angiogenesis and tumor progression", Blood, vol. 96, No. 1, pp. 34-40 (2000).

Samad, F. et al., "Tumor necrosis factor α is a key component in the obesity-linked elevation of plasminogen activator inhibitor 1", Proc. Natl. Acad. Sci. USA, vol. 96, pp. 6902-6907 (1999).

Samson, M. et al., "Molecular Cloning and Functional Expression of a New Human CC-Chemokine Receptor Gene", Biochemistry, vol. 35, No. 11, pp. 3362-3367 (1996).

Sartipy, P. et al., "Monocyte chemoattractant protein 1 in obesity and insulin resistance", Proceedings of the National Academy of Sciences, vol. 100, No. 12, pp. 7265-7270 (2003).

Saunders, J. et al., "Opportunities for novel therapeutic agents acting at chemokine receptors", Drug Discovery Today, vol. 4, No. 2, pp. 80-92 (1999).

Schimmer, R.C. et al., "Streptococcal Cell Wall-Induced Arthritis: Requirements for IL-4, IL-10, IFN-γ, and Monocyte Chemoattractant Protein-1", The Journal of Immunology, vol. 160, pp. 1466-1471 (1998).

Schober, A. et al., "Crucial Role of the CCL2/CCR2 Axis in Neointimal Hyperplasia After Arterial Injury in Hyperlipidemic Mice Involves Early Monocyte Recruitment and CCL2 Presentation on Platelets", Circulation Research, vol. 95, pp. 1125-1133 (2004).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shimizu, S. et al., "Anti-monocyte chemoattractant protein-1 gene therapy attenuates nephritis in MRL/Ipr mice", Rheumatology, vol. 43, pp. 1121-1128 (2004).

Smith, M.W. et al., "Contrasting Genetic Influence of *CCR2* and *CCR5* Variants on HIV-1 Infection and Disease Progression", Science, vol. 277, pp. 959-965 (1997).

Spagnolo, P. et al., "C-C Chemokine Receptor 2 and Sarcoidosis: Association with Löfgren's Syndrome", American Journal of Respiratory and Critical Care Medicine, vol. 168, pp. 1162-1166 (2003).

Tacke, F. et al., "Monocyte subsets differentially employ CCR2, CCR5, and CX3CR1 to accumulate within atherosclerotic plaques", The Journal of Clinical Investigation, vol. 117, No. 1, pp. 185-194 (2007).

Tatewaki, H. et al., "Blockade of monocyte chemoattractant protein-1 by adenoviral gene transfer inhibits experimental vein graft neointimal formation", Journal of Vascular Surgery, vol. 45, No. 6, pp. 1236-1243 (2007).

Tesch, G.H. et al., "Monocyte Chemoattractant Protein 1-dependent Leukocyte Infiltrates are Responsible for Autoimmune Disease in MRL-$Fas^{lpr}$ Mice", J. Exp. Med., vol. 190, No. 12, pp. 1813-1824 (1999).

Tesch, G.H. et al., "Monocyte chemoattractant protein-1 promotes macrophage-mediated tubular injury, but not glomerular injury, in nephrotoxic serum nephritis", The Journal of Clinical Investigation, vol. 103, No. 1, pp. 73-80 (1999).

Tokuyama, H. et al., "The simultaneous blockade of chemokine receptors CCR2, CCR5 and CXCR3 by a non-peptide chemokine receptor antagonist protects mice from dextran sodium sulfate-mediated colitis", International Immunology, vol. 17, No. 8, pp. 1023-1034 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Tsou, C.-L. et al., "Critical roles for CCR2 and MCP-3 in monocyte mobilization from bone marrow and recruitment to inflammatory sites", The Journal of Clinical Investigation, vol. 117, No. 4, pp. 902-909 (2007).

Tsuruta, S. et al., "Anti-monocyte chemoattractant protein-1 gene therapy prevents dimethylnitrosamine-induced hepatic fibrosis in rats", International Journal of Molecular Medicine, vol. 14, pp. 837-842 (2004).

Vestergaard, C. et al., "Expression of CCR2 on Monocytes and Macrophages in Chronically Inflamed Skin in Atopic Dermatitis and Psoriasis", Acta Derm. Venereol., vol. 84, pp. 353-358 (2004).

Wada, T. et al., "Gene Therapy via Blockade of Monocyte Chemoattractant Protein-1 for Renal Fibrosis", Journal of the American Society of Nephrology, vol. 15, pp. 940-948 (2004).

Weisberg, S.P. et al., "CCR2 modulates inflammatory and metabolic effects of high-fat feeding", The Journal of Clinical Investigation, vol. 116, No. 1, pp. 115-124 (2006).

Weisberg, S.P. et al., "Obesity is associated with macrophage accumulation in adipose tissue", The Journal of Clinical Investigation, vol. 112, No. 12, pp. 1796-1808 (2003).

Wells, T.N.C. et al., "Plagiarism of the host immune system: lessons about chemokine immunology from viruses", Current Opinion in Biotechnology, vol. 8, pp. 741-748 (1997).

Xu, H. et al., "Chronic inflammation in fat plays a crucial role in the development of obesity-related insulin resistance", The Journal of Clinical Investigation, vol. 112, No. 12, pp. 1821-1830 (2003).

Yamamoto, T. et al., "Role of Monocyte Chemoattractant Protein-1 and its Receptor, CCR-2, in the Pathogenesis of Bleomycin-Induced Scleroderma", The Journal of Investigative Dermatology, vol. 121, No. 3, pp. 510-516 (2003).

Yoshie, O. et al., "Novel lymphocyte-specific CC chemokines and their receptors", Journal of Leukocyte Biology, vol. 62, pp. 634-644 (1997).

Youssef, S. et al., "C-C chemokine-encoding DNA vaccines enhance breakdown of tolerance to their gene products and treat ongoing adjuvant arthritis", The Journal of Clinical Investigation, vol. 106, No. 3, pp. 361-371 (2000).

Zlotnik, A. et al., "Chemokines: A New Classification System and Their Role in Immunity", Immunity, vol. 12, pp. 127-127 (2000).

\* cited by examiner

CYCLIC DERIVATIVES AS MODULATORS OF CHEMOKINE RECEPTOR ACTIVITY

This application claims priority from U.S. Provisional Application Nos. 60/834,235, and 60/896,026 filed Jul. 28, 2006 and Mar. 21, 2007, respectively, the disclosures of both of which are incorporated herein by reference.

FIELD OF THE INVENTION

The invention relates generally to modulators of chemokine receptor activity having an unexpected combination of desirable pharmacological properties. Pharmaceutical compositions containing the same, and methods of using the same as agents for treatment and prevention of inflammatory, allergic, autoimmune, metabolic, cancer and/or cardiovascular diseases and in particular, diabetes, atherosclerosis, Crohn's disease, and multiple sclerosis, along with methods of preparing compounds and intermediates therefor. Metabolites of active compounds, pharmaceutical compositions, and use thereof are also provided herein.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Charo and Rasonhoff, *New Eng J. Med.* 2006, 354, 610-621; Luster, *New Eng. J. Med.* 1998, 338, 436-445; and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-11β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., J. Immunol., 1996, 157, 2759-2763); CCR-10 (or "CKR-10" or "CC-CKR-10") [MCP-1, MCP-3] (Bonini, et al., *DNA and Cell Biol.* 1997, 16, 1249-1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo and Rasonhoff, *New Eng J. Med.* 2006, 354, 610-621; Z. Gao and W. A. Metz, *Chem. Rev.* 2003, 103, 3733; P. H. Carter, *Current Opinion in Chemical Biology* 2002, 6, 510; Trivedi, et al, *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1$^{-/-}$ mice were unable to recruit monocytes into sites of inflammation after several different types of immune challenge (Bao Lu, et al., *J. Exp. Med.* 1998, 187, 601). Likewise, CCR-2−/− mice were unable to recruit monocytes or produce interferon-γ when challenged with various exogenous agents; moreover, the leukocytes of CCR-2 null mice did not migrate in response to MCP-1 (Landin Boring, et al., *J. Clin. Invest.* 1997, 100, 2552), thereby demonstrating the specificity of the MCP-1/CCR-2 interaction. Two other groups have independently reported equivalent results with different strains of CCR-2−/− mice (William A. Kuziel, et al., *Proc. Natl. Acad. Sci. USA* 1997, 94, 12053, and Takao Kurihara, et al., *J. Exp. Med.* 1997, 186, 1757). The viability and generally normal health of the MCP-1−/− and CCR-2−/− animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (reviewed in: M. Feria and F. Diaz-González, *Exp. Opin. Ther. Patents* 2006, 16, 49; and J. Dawson, W. Miltz, and C. Wiessner, C. *Exp. Opin. Ther. Targets* 2003, 7, 35). This hypothesis has now been validated in a number of different animal disease models, as described below.

It is known that MCP-1 is upregulated in patients with rheumatoid arthritis (Alisa Koch, et al., *J. Clin. Invest.* 1992, 90, 772-779). Moreover, several preclinical studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, the disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-lpr mouse model of arthritis (Jiang-Hong Gong, et al., *J. Exp. Med.* 1997, 186, 131). Moreover, it has been demonstrated the administration of small molecule CCR2 antagonists reduced clinical score in rodent models of arthritis (C. M. Brodmerkel, et al, *J. Immunol.* 2005, 175, 5370; and M. Xia, et al. US patent application 0069123, 2006). Administration of an anti-CCR2 antibody had varying effects on murine CIA, depending on the time of administration (H. Bruhl, et al. *J. Immunol.* 2004, 172, 890). Recent studies with CCR2−/− mice have suggested that deletion of CCR2 can exacerbate rodent arthritis models in specific experimental circumstances (M. P. Quinones, et al. *J. Clin. Invest.* 2004, 113, 856; M. P. Quinones, et al. *J. Mol. Med.* 2006, 84, 503).

It is known that MCP-1 is upregulated in atherosclerotic lesions, and it has been shown that circulating levels of MCP-1 are reduced through treatment with therapeutic agents (Abdolreza Rezaie-Majd, et al, *Arterioscler. Thromb. Vasc. Biol.* 2002, 22, 1194-1199). Several key studies have demonstrated the potential therapeutic value of antagonism of the MCP-1/CCR2 interaction in treating atherosclerosis. For example, when MCP-1−/− mice are crossed with LDL receptor-deficient mice, an 83% reduction in aortic lipid deposition was observed (Long Gu, et al., *Mol. Cell.* 1998, 2, 275). Similarly, when MCP-1 was genetically ablated from mice which already overexpressed human apolipoprotein B, the resulting mice were protected from atherosclerotic lesion formation relative to the MCP-1+/+ apoB control mice (Jennifa Gosling, et al., *J. Clin. Invest.* 1999, 103, 773). Likewise, when CCR-2−/− mice are crossed with apolipoprotein E−/− mice, a significant decrease in the incidence of atherosclerotic lesions was observed (Landin Boring, et al, *Nature* 1998, 394, 894; T. C. Dawson, et al. *Atherosclerosis* 1999, 143, 205). Finally, when apolipoprotein E−/− mice are administered a gene encoding a peptide antagonist of CCR2, then lesion size is decreased and plaque stability is increased (W. Ni, et al. *Circulation* 2001, 103, 2096-2101). Transplantation of bone marrow from CCR2−/− mice into ApoE3-Leiden mice inhibited early atherogenesis (J. Guo, et al. *Arterioscler. Thromb. Vasc. Biol.* 2003, 23, 447), but had minimal effects on advanced lesions (J. Guo, et al. *Arterioscler. Thromb. Vasc. Biol.* 2005, 25, 1014).

Patients with type 2 diabetes mellitus typically exhibit insulin resistance as one of the hallmark features of the disease. Insulin resistance is also associated with the grouping of abnormalities known as the "metabolic syndrome" or "syndrome X," which includes obesity, atherosclerosis, hypertension, and dyslipidemia (reviewed in: Eckel, et al. *Lancet* 2005, 365, 1415). It is well-recognized that inflammation plays a role in exacerbating the disease process in type 2 diabetes and the "syndrome X" pathologies (reviewed in: Chen, *Pharmacological Research* 2006, 53, 469; Neels and Olefsky, *J. Clin. Invest.* 2006, 116, 33; Danadona and Aljada, *Am J Cardiol.* 2002 90, 27G-33G; Pickup and Crook, *Diabetologia* 1998, 41, 1241). MCP-1 is recognized as playing a role in obesity-induced insulin resistance. In culture, human preadipocytes constitutively expressed MCP-1 (Gerhardt, *Mol. Cell. Endocrinology* 2001, 175, 81). CCR2 is expressed on adipocytes; Addition of MCP-1 to differentiated adipocytes in vitro decreases insulin-stimulated glucose uptake and the expression of several adipogenic genes (LpL, adipsin, GLU-4), aP2, β3-adrenergic receptor, and PPARγ) (P. Sartipy and D. Loskutoff, *Proc. Natl. Acad. Sci. USA* 1999, 96, 6902). Patients with type 2 diabetes had greater levels of circulating MCP-1 than non-diabetic controls (S. Nomura, et al. *Clin. Exp. Immunol.* 2000, 121, 437), and release of MCP-1 from adipose tissue could be reduced by treatment with anti-diabetic therapies such as metformin or thiazolidinediones (J. M. Bruun, et al. *J. Clin. Endocrinol. Metab.* 2005, 90, 2282). Likewise, MCP-1 was also overexpressed in murine experimental models of obesity, and was primarily produced by adipose tissue (Sartipy and Loskutoff, *Proc. Natl. Acad. Sci. USA* 2003, 100, 7265). In obese mice, the expression of MCP-1 both preceded and occurred concurrently with the onset of insulin resistance (H. Xu, et al. *J. Clin. Invest.* 2003, 112, 1821). Another study showed that the expression of MCP-1 positively correlated with body mass in the perigonadal adipose tissue of mice (Weisberg, et al. *J. Clin. Invest.* 2003, 112, 1796). Consistent with these data, the development of insulin resistance in db/db mice was ameliorated either via genetic deletion of MCP-1 or by gene-induced expression of a dominant negative peptide (H. Kanda, et al. *J. Clin. Invest.* 2006, 116, 1494). The logical converse could also be demonstrated: overexpression of MCP-1 in adipose tissue promoted insulin resistance (N. Kamei, et al. *J. Biol. Chem.* 2006, 281, 26602). One conflicting result showing that genetic deletion of MCP-1 does not effect insulin resistance in the db/db mouse has also appeared (F. Y. Chow, et al. *Diabetologia* 2007, 50, 471). Consistent with the data on MCP-1, direct studies with CCR2 (the MCP-1 receptor) have showed that it plays a role in the formation of obesity and obesity-induced insulin resistance. Maintenance of a high fat diet increased the numbers of circulating $CCR2^+$ inflammatory monocytes in both wild-type (C. L. Tsou, et al. *J. Clin. Invest.* 2007, 117, 902) and $ApoE^{-/-}$ mice (F. Tacke, et al. *J. Clin. Invest.* 2007, 117, 185). Genetic deletion of CCR2 reduced numbers of activated macrophages in murine adipose tissue (C. N. Lumeng, et al. *Diabetes* 2007, 56, 16), but did not affect a population of M2 adipose macrophages thought to maintain the "lean" state (C. N. Lumeng, et al. *J. Clin. Invest.* 2007, 117, 175). Genetic deletion of CCR2 reduced diet-induced obesity and improved insulin sensitivity in diet-induced obesity model (S. P. Weisberg, et al. *J. Clin. Invest.* 2006, 116, 115; P Cornelius, R P Gladue, R S Sebastian, WO patent 2006/013427 A2), 2006), depending on experimental conditions (A. Chen, et al. *Obes. Res.* 2005, 13, 1311). Administration of a small molecule CCR2 antagonist also improved insulin sensitivity in this same model (S. P. Weisberg, et al. *J. Clin. Invest.* 2006, 116, 115).

Two studies described the important role of CCR2 in hypertension-induced vascular inflammation, remodeling, and hypertrophy (E Bush et al., *Hypertension* 2000, 36, 360; M Ishibashi, et al. *Circ. Res.* 2004, 94, 1203).

It is known that MCP-1 is upregulated in human multiple sclerosis, and it has been shown that effective therapy with interferon β-1b reduces MCP-1 expression in peripheral blood mononuclear cells, suggesting that MCP-1 plays a role in disease progression (Carla Jarlori, et al., *J. Neuroimmunol.* 2002, 123, 170-179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple sclerosis. Administration of antibodies for MCP-1 to animals with EAE significantly diminished disease relapse (K. J. Kennedy, et al., *J. Neuroimmunol.* 1998, 92, 98). Furthermore, two reports have shown that CCR-2-/- mice are resistant to EAE (B. T. Fife, et al., *J. Exp. Med.* 2000, 192, 899; L. Izikson, et al., *J. Exp. Med.* 2000, 192, 1075). A subsequent report extended these initial observations by examining the effects of CCR2 deletion in mice from different strains (S. Gaupp, et al. *Am. J. Pathol.* 2003, 162, 139). Notably, administration of a small molecule CCR2 antagonist also blunted disease progression in C57BL/6 mice (C. M. Brodmerkel, et al. *J. Immunol.* 2005, 175, 5370).

It is known that MCP-1 is upregulated in patients who develop bronchiolitis obliterans syndrome after lung transplantation (Martine Reynaud-Gaubert, et al., *J. of Heart and Lung Transplant.*, 2002, 21, 721-730; John Belperio, et al., *J. Clin. Invest.* 2001, 108, 547-556). In a murine model of bronchiolitis obliterans syndrome, administration of an antibody to MCP-1 led to attenuation of airway obliteration; likewise, CCR2-/- mice were resistant to airway obliteration in this same model (John Belperio, et al., *J. Clin. Invest.* 2001, 108, 547-556). These data suggest that antagonism of MCP-1/CCR2 may be beneficial in treating rejection of organs following transplantation. In addition, studies have shown that disruption of MCP-1/CCR2 axis was able to prolong the survival of islet transplant (I Lee et al. *J Immunol* 2003, 171, 6929; R Abdi et al., *J Immunol* 2004, 172, 767). In rat graft models, CCR2 and MCP-1 was shown to be upregulated in grafts that develop graft vasculopathy (K Horiguchi et al., *J Heart Lung Transplant.* 2002, 21, 1090). In another study, anti-MCP-1 gene therapy attenuated graft vasculopathy (A Saiura et al., *Artherioscler Thromb Vasc Biol* 2004, 24, 1886). One study described inhibition of experimental vein graft neoinitimal formation by blockage of MCP-1 (H Tatewaki et al., *J Vasc Surg.* 2007, 45, 1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., *J. Immunol.* 1997, 158, 4398). Consistent with this, MCP-1-/- mice displayed a reduced response to challenge with *Schistosoma mansoni* egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1-/- mice with induced nephrotoxic serum nephritis showed significantly less tubular damage than their MCP-1+/+ counterparts (Gregory H. Tesch, et al., *J. Clin. Invest.* 1999, 103, 73).

Several studies have demonstrated the potential therapeutic value of antagonism of the MCP-1/CCR2 interaction in treating systemic lupus erythematosus. $CCR2^{-/-}$ mice exhibited prolonged survival and reduced renal disease relative to their WT counterparts in a murine model of systemic lupus erythematosus (G. Perez de Lema, et al. *J. Am. Soc. Neph.* 2005, 16, 3592). These data are consistent with the disease-modifying activity found in recent studies on genetic deletion of MCP-1 (S. Shimizu, et al. *Rheumatology (Oxford)* 2004, 43, 1121; Gregory H. Tesch, et al., *J. Exp. Med.* 1999, 190, 1813) or administration of a peptide antagonist of CCR2 (H. Hasegawa, et al. *Arthritis & Rheumatism* 2003, 48, 2555) in rodent models of lupus.

A remarkable 30-fold increase in $CCR2^+$ lamina propria lymphocytes was observed in the small bowels from Crohn's patients relative to non-diseased ileum (S. J. Connor, et al. *Gut* 2004, 53, 1287). Also of note, there was an expansion in the subset of circulating $CCR2^+/CD14^+/CD56^+$ monocytes in patients with active Crohn's disease relative to controls. Several rodent studies have demonstrated the potential therapeutic value of antagonism of the MCP-1/CCR2 interaction in treating Crohn's disease/colitis. $CCR-2^{-/-}$ mice were protected from the effects of dextran sodium sulfate-induced colitis (Pietro G. Andres, et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (H. Tokuyama, et al. *Int. Immunol.* 2005, 17, 1023). Finally, MCP-1-/- mice showed substantially reduced colonic damage (both macroscopic and histological) in a hapten-induced model of colitis (W. I. Khan, et al. *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804).

One study described the association of promoter polymorphism in the MCP-1 gene with sceroderma (systemic sclerosis) (S Karrer et al., *J Invest Dermatol.* 2005, 124, 92). In related models of tissue fibrosis, inhibition of CCR2/MCP-1 axis reduced fibrosis in skin (T Yamamoto and K Nishioka, *J Invest Dermatol* 2003, 121, 510; A M Ferreira et al., *J Invest Dermatol.* 2006, 126, 1900), lung (T Okuma et al., *J Pathol.* 2004, 204, 594; M Gharaee-Kermani et al., *Cytokine* 2003, 24, 266), kidney (K Kitagawa et al., *Am J Pathol* 2004, 165, 237; T Wada et al., *J Am Soc Nephrol* 2004, 15, 940), heart (S Hayashidani et al., *Circulation* 2003, 108, 2134), and liver (S Tsuruta et al., *Int J Mol Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

Several studies have shown the potential therapeutic value of antagonism of the MCP-1/CCR2 interaction in treating cancer (reviewed in: M. J. Craig and R. D. Loberg, *Cancer Metastasis Rev.* 2006, 25, 611; I. Conti and B. Rollins, *Seminars in Cancer Biology* 2004, 14, 149; R. Giles and R. D. Loberg, *Curr. Cancer Drug Targets* 2006, 6, 659). When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34-40). Using human clinical tumor specimens, CCR2 expression was associated with prostrate cancer progression (Y. Lu, et al. *J. Cell. Biochem.* 2007, 101, 676). In vitro, MCP-1 expression has been shown to mediate prostrate cancer cell growth and invasion (Y. Lu, et al. *Prostate* 2006, 66, 1311); furthermore, MCP-1 expressed by prostate cancer cells induced human bone marrow progenitors for bone resorption (Y. Lu, et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (F. Cipollone, et al. *Arterioscler. Thromb. Vasc. Biol.* 2001, 21, 327). Mice deficient in CCR2 or in MCP-1 showed reductions in the intimal area and in the intima/media ratio (relative to wildtype littermates) after arterial injury (Merce Roque, et al. *Arterioscler. Thromb. Vasc. Biol.* 2002, 22, 554; A. Schober, et al. *Circ. Res.* 2004, 95, 1125; W. J. Kim, et al. *Biochem Biophys Res Commun.* 2003, 310, 936). In mice, transfection of a dominant negative inhibitor of MCP-1 in the skeletal muscle (K. Egashira, et al. *Circ. Res.* 2002, 90, 1167) also reduced intimal hyperplasia after arterial injury. Blockade of CCR2 using a neutralizing antibody reduced neointimal hyperplasia after stenting in primates (C. Horvath, et al. *Circ. Res.* 2002, 90, 488).

Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). In addition, studies have shown that both CCR2$^{-/-}$ (O. B. Dimitrijevic, et al. *Stroke* 2007, 38, 1345) and MCP-1$^{-/-}$ mice (P. M. Hughes, et al. *J. Cereb. Blood Flow Metab.* 2002, 22, 308) are partially protected from ischemia/reperfusion injury.

It is known that monocytes/macrophages play an important role in the development of neuropathic pain (Liu T, van Rooijen N, Tracey D J, *Pain* 2000, 86, 25). Consistent with this notion, a potential role for CCR2 in the treatment of both inflammatory and neuropathic pain has been described recently. CCR2$^{-/-}$ mice showed altered responses to inflammatory pain relative to their WT counterparts, including reduced pain behavior after intraplantar formalin injection and slightly reduced mechanical allodynia after intraplantar CFA injection (C. Abbadie, et al. *Proc. Natl. Acad. Sci., USA* 2003, 100, 7947). In addition, CCR2$^{-/-}$ mice did not display significant mechanical allodynia after sciatic nerve injury. Likewise, a small molecule CCR2 antagonist reduced mechanical allodynia to ~80% of pre-injury levels after oral administration (C. Abbadie, J. A. Lindia, and H. Wang, WO PCT 110376, 2004).

One study described the critical role of MCP-1 in ischemic cardiomyopathy (N. G. Frangogiannis, et al., *Circulation* 2007, 115, 584). Another study described the attenuation of experimental heart failure following inhibition of MCP-1 (S Hayashidani et al., *Circulation* 2003, 108, 2134).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127); correlative findings with predominance of CCR2+ cells have also been reported (C. Vestergaard, et al. *Acta Derm. Venerol.* 2004, 84, 353). Finally, a recent report has shown that MCP-1 is overexpressed in the brains and cerebrospinal fluid of patients with HIV-1-associated dementia (Alfredo Garzino-Demo, WO 99/46991).

In addition, CCR2 polymorphism has been shown to be associated with sarcoidosis at least in one subset of patients (P. Spagnolo, et al. *Am J Respir Crit. Care Med.* 2003, 168, 1162).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR2 is also the receptor for the human chemokines MCP-2, MCP-3, and MCP-4 (Luster, *New Eng J. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

Accordingly, compounds that modulate chemokine activity could demonstrate a wide range of utilities in treating inflammatory, allergic, autoimmune, metabolic, cancer and/or cardiovascular diseases. Patent application publication WO2005021500 (incorporated herein by reference and assigned to present applicant) discloses compounds that modulate MCP-1, MCP-2, MCP-3 and MCP-4 activity via CCR2. The reference also discloses various processes to prepare these compounds including multistep syntheses that include the introduction and subsequent removal of protecting groups.

It is desirable to find new compounds with improved pharmacological characteristics compared with known chemokine modulators. For example, it is desirable to find new compounds with improved CCR-2 inhibitory activity and selectivity for CCR-2 versus other G protein-coupled receptors (i.e. 5HT2A receptor). It is also desirable to find compounds with advantageous and improved characteristics in one or more of the following categories:

(a) pharmaceutical properties (i.e. solubility, permeability, amenability to sustained release formulations);

(b) dosage requirements (e.g., lower dosages and/or once-daily dosing);

(c) factors which decrease blood concentration peak-to-trough characteristics (i.e. clearance and/or volume of distribution);

(d) factors that increase the concentration of active drug at the receptor (i.e. protein binding, volume of distribution);

(e) factors that decrease the liability for clinical drug-drug interactions (cytochrome P450 enzyme inhibition or induction, such as CYP 2D6 inhibition, see G. K. Dresser, J. D. Spence, D. G. Bailey, *Clin. Pharmacokinet.* 2000, 38, 41-57, which is hereby incorporated by reference);

(f) factors that decrease the potential for adverse side-effects (e.g. pharmacological selectivity beyond G protein-coupled receptors, potential chemical or metabolic reactivity, limited CNS penetration, ion-channel selectivity). It is especially desirable to find compounds having a desirable combination of the aforementioned pharmacological characteristics.

It is also desirable in the art to provide new and/or improved processes to prepare such compounds. These processes may be characterized, without limitation, by a) facile adaptation to larger scale production, such as pilot plant or manufacturing scales; b) process steps and/or techniques enabling improvements in the purity (including chiral purity), stability and/or ease of handling of intermediates and/or final compounds; and/or c) fewer process steps.

SUMMARY OF THE INVENTION

Accordingly, disclosed herein are novel modulators of chemokine activity, or pharmaceutically acceptable salts or prodrugs thereof, having an unexpected combination of desirable pharmacological characteristics.

The present disclosure provides pharmaceutical compositions comprising a pharmaceutically acceptable carrier and a therapeutically effective amount of at least one of the compounds of the present invention or a pharmaceutically acceptable salt or prodrug form thereof.

The present disclosure also provides methods for treating inflammatory, allergic, autoimmune, metabolic, cancer and/or cardiovascular diseases, particularly diabetes, multiple sclerosis, Crohn's disease and/or atherosclerosis, comprising administering to a host in need of such treatment a therapeutically effective amount of at least one of the compounds of the present invention, or a pharmaceutically acceptable salt or prodrug form thereof.

The present disclosure provides a process for preparing compounds disclosed herein and intermediates useful therefore.

The present disclosure also provides metabolites of active compounds, or pharmaceutically acceptable salts or prodrugs thereof, pharmaceutical compositions thereof and methods of using the metabolites in the treatment of inflammatory, allergic, autoimmune, metabolic, cancer and/or cardiovascular diseases, particularly diabetes, multiple sclerosis, Crohn's disease and/or atherosclerosis.

The present disclosure provides novel cyclic derivatives for use in therapy.

The present disclosure provides the use of novel cyclic derivatives for the manufacture of a medicament for the treatment of inflammatory, allergic, autoimmune, metabolic, cancer and/or cardiovascular diseases.

DETAILED DESCRIPTION

Figure 1:
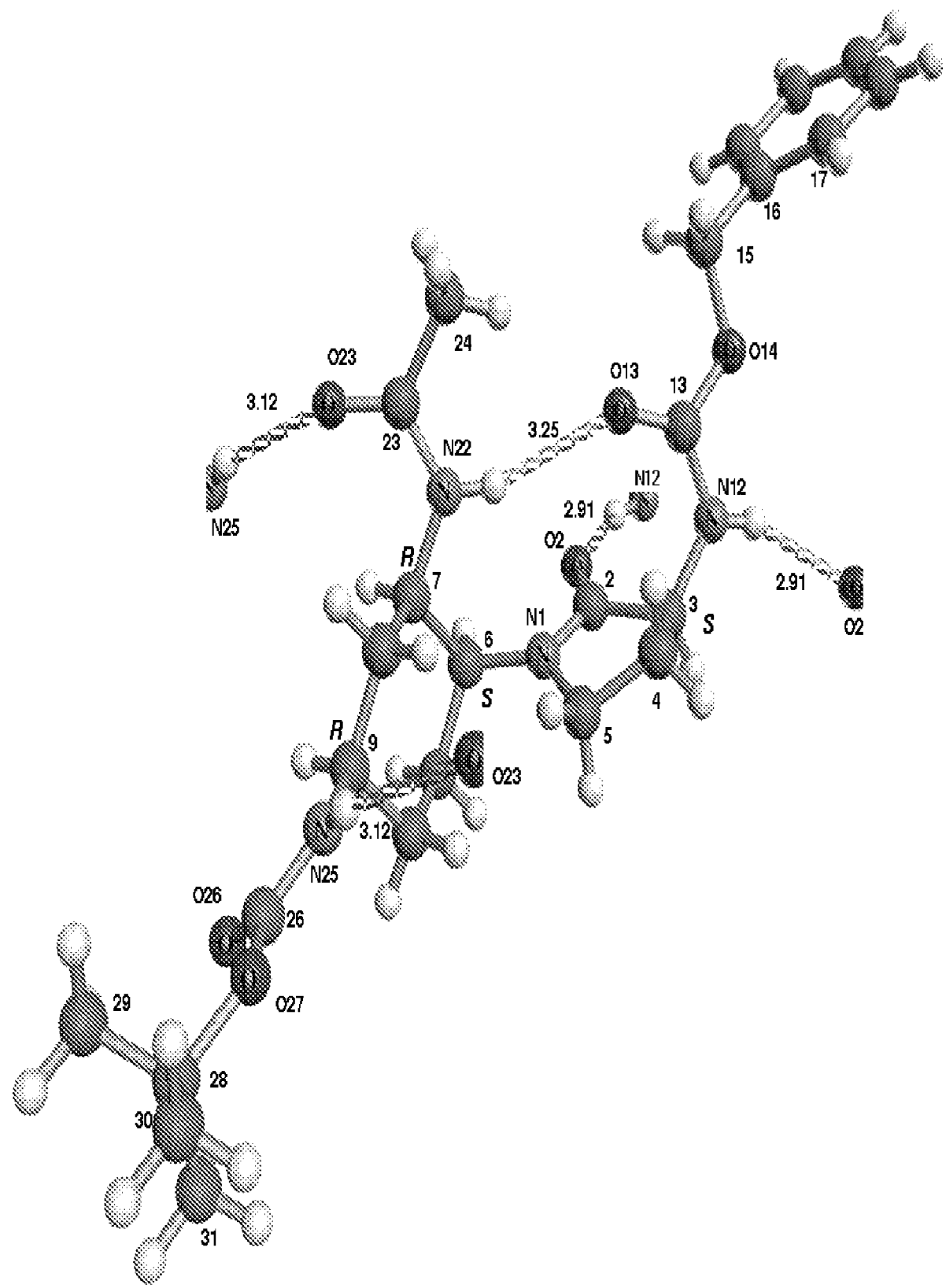
FIG. 1 discloses an X-ray crystal structure of tert-butyl (1R,3R,4S)-3-acetamido-4-((S)-3-(benzyloxycarbonylamino)-2-oxopyrrolidin-1-yl)cyclohexylcarbamate.

This disclosure relates generally to modulators of chemokine receptor activity having unexpected combination of desirable pharmacological properties. Pharmaceutical compositions containing the same, and methods of using the same as agents for the treatment and prevention of inflammatory, allergic, autoimmune, metabolic, cancer and/or cardiovascular diseases, particularly diabetes, atherosclerosis, Crohn's disease and multiple sclerosis, along with methods of preparing compounds and intermediates therefor.

Compounds of the present invention unexpectedly demonstrate a desirable combination of pharmacological characteristics including a surprisingly high degree of oral bioavailability in combination with indications that the compounds are highly efficacious and have excellent safety criteria.

Known modulators of CCR2 receptors, such as those disclosed in patent publication WO2005021500 published Mar. 10, 2005 (U.S. Pat. No. 7,163,937, issued Jan. 16, 2007, assigned to present Applicant) that demonstrate an adequate degree of membrane permeability (a critical factor of oral bioavailability), are not sufficiently efficacious, as measured by their CCR2-binding ability, and/or they lack appropriate criteria for safety as indicated by ion channel selectivity as measured by hERG and Ca ion channel studies.

In contrast, as illustrated by the data presented herein in the section titled "Comparative Pharmacological Characteristics", infra, the relatively polar molecules of the present invention demonstrate a surprisingly high degree of membrane permeability, and yet maintain potent CCR2 binding ability with excellent ion channel selectivity.

Accordingly, the present invention provides new chemokine modulators having improved pharmacological characteristics that are expected to be useful in treating inflammatory, allergic, autoimmune, metabolic, cancer and/or cardiovascular diseases.

Also provided herein are metabolites of active compounds, pharmaceutical compositions, and a method of using the same for the treatment and prevention of inflammatory, allergic, autoimmune, metabolic, cancer and/or cardiovascular diseases, particularly diabetes, atherosclerosis, Crohn's disease and multiple sclerosis, along with methods of preparing compounds and intermediates therefor. The active compounds are N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide (described in co-pending patent application Ser. No. 11/782,742) and N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide (described in co-pending patent application Ser. No. 11/782,704). The activity of these metabolites is presented herein in the section titled "Comparative Pharmacological Characteristics" infra.

EMBODIMENTS

In one embodiment, the disclosure is directed to a compound selected from (i) N-((1R,2S,5R)-2-((3S)-3-((6-tert-butylpyrimido[5,4-d]pyrimidin-4-yl)amino)-2-oxo-1-pyrrolidinyl)-5-(isopropyl(methyl)amino)cyclohexyl)acetamide;

N-((1R,2S,5R)-5-(methylamino)-2-((3S)-2-oxo-3-((6-(trifluoromethyl)-4-quinazolinyl)amino)-1-pyrrolidinyl)cyclohexyl)acetamide;

N-((1R,2S,5R)-5-(isopropyl(methyl)amino)-2-((3S)-2-oxo-3-((6-(trifluoromethyl)-4-quinazolinyl)amino)-1-pyrrolidinyl)cyclohexyl)formamide;

N-((1R,2S,5R)-5-(dimethylamino)-2-((3S)-2-oxo-3-((6-(trifluoromethyl)-4-quinazolinyl)amino)-1-pyrrolidinyl)cyclohexyl)acetamide;

N-((3S)-1-((1S,2R,4R)-2-acetamido-4-(isopropyl(methyl)amino)cyclohexyl)-2-oxo-3-pyrrolidinyl)-6-tert-butyl-2-pyridinecarboxamide;

N-((1R,2S,5R)-5-amino-2-((3S)-2-oxo-3-((6-(trifluoromethyl)-4-quinazolinyl)amino)-1-pyrrolidinyl)cyclohexyl) propanamide;

2-tert-butyl-N-((3S)-1-((1S,2R,4R)-4-(tert-butylamino)-2-(methanesulfonylamino)cyclohexyl)-2-oxo-3-pyrrolidinyl)-4-pyrimidinecarboxamide;

2-tert-butyl-N-((3S)-1-((1S,2R,4R)-4-(tert-butylamino)-2-(propionylamino)cyclohexyl)-2-oxo-3-pyrrolidinyl)-4-pyrimidinecarboxamide;

N-((1R,2S,5R)-5-(tert-butylamino)-2-((3S)-3-((6-tert-butylpyrimido[5,4-d]pyrimidin-4-yl)amino)-2-oxo-1-pyrrolidinyl)cyclohexyl)methanesulfonamide; and N-(((1S,2S,5R)-5-methoxy-2-((3S)-2-oxo-3-((6-(trifluoromethyl)-4-quinazolinyl)amino)-1-pyrrolidinyl)cyclohexyl)methyl)acetamide; or (ii) a pharmaceutically acceptable salt of (i) thereof.

In another embodiment, the disclosure is directed to a compound that is N-((1R,2S,5R)-2-((3S)-3-((6-tert-butylpyrimido[5,4-d]pyrimidin-4-yl)amino)-2-oxo-1-pyrrolidinyl)-5-(isopropyl(methyl)amino)cyclohexyl)acetamide, or a pharmaceutically acceptable salt thereof.

In one embodiment, the disclosure is directed to a compound that is N-((1R,2S,5R)-5-(methylamino)-2-((3S)-2-oxo-3-((6-(trifluoromethyl)-4-quinazolinyl)amino)-1-pyrrolidinyl)cyclohexyl)acetamide, or a pharmaceutically acceptable salt thereof.

In another embodiment, the disclosure is directed to a compound that is N-((1R,2S,5R)-5-(isopropyl(methyl)amino)-2-((3S)-2-oxo-3-((6-(trifluoromethyl)-4-quinazolinyl)amino)-1-pyrrolidinyl)cyclohexyl)formamide, or a pharmaceutically acceptable salt thereof.

In another embodiment, the disclosure is directed to a compound that is N-((1R,2S,5R)-5-(dimethylamino)-2-((3S)-2-oxo-3-((6-(trifluoromethyl)-4-quinazolinyl)amino)-1-pyrrolidinyl)cyclohexyl)acetamide, or a pharmaceutically acceptable salt thereof.

In another embodiment, the disclosure is directed to a compound that is N-((3S)-1-((1S,2R,4R)-2-acetamido-4-(isopropyl(methyl)amino)cyclohexyl)-2-oxo-3-pyrrolidinyl)-6-tert-butyl-2-pyridinecarboxamide, or a pharmaceutically acceptable salt thereof.

In another embodiment, the disclosure is directed to a compound that is N-((1R,2S,5R)-5-amino-2-((3S)-2-oxo-3-((6-(trifluoromethyl)-4-quinazolinyl)amino)-1-pyrrolidinyl)cyclohexyl)propanamide, or a pharmaceutically acceptable salt thereof.

In another embodiment, the disclosure is directed to a compound that is 2-tert-butyl-N-((3S)-1-((1S,2R,4R)-4-(tert-butylamino)-2-(methanesulfonylamino)cyclohexyl)-2-oxo-3-pyrrolidinyl)-4-pyrimidinecarboxamide, or a pharmaceutically acceptable salt thereof.

In another embodiment, the disclosure is directed to a compound that is 2-tert-butyl-N-((3S)-1-((1S,2R,4R)-4-(tert-butylamino)-2-(propionylamino)cyclohexyl)-2-oxo-3-pyrrolidinyl)-4-pyrimidinecarboxamide, or a pharmaceutically acceptable salt thereof.

In another embodiment, the disclosure is directed to a compound that is N-((1R,2S,5R)-5-(tert-butylamino)-2-((3S)-3-((6-tert-butylpyrimido[5,4-d]pyrimidin-4-yl)amino)-2-oxo-1-pyrrolidinyl)cyclohexyl)methanesulfonamide, or a pharmaceutically acceptable salt thereof.

In another embodiment, the disclosure is directed to a compound that is N-(((1S,2S,5R)-5-methoxy-2-((3S)-2-oxo-3-((6-(trifluoromethyl)-4-quinazolinyl)amino)-1-pyrrolidinyl)cyclohexyl)methyl)acetamide, or a pharmaceutically acceptable salt thereof.

Another embodiment is a pharmaceutical composition, comprising a pharmaceutically acceptable carrier and a compound of the Examples.

Another embodiment is a method for modulation of chemokine or chemokine receptor activity comprising administering to a patient in need thereof a therapeutically effective amount of a compound of the Examples.

Another embodiment is a method for modulation of CCR-2 receptor activity comprising administering to a patient in need thereof a therapeutically effective amount of a compound of the Examples.

Another embodiment is a method for modulation of MCP-1, MCP-2, MCP-3 and MCP-4, and MCP-5 activity that is mediated by the CCR2 receptor comprising administering to a patient in need thereof a therapeutically effective amount of a compound of the Examples.

Another embodiment is a method for modulation of MCP-1 activity comprising administering to a patient in need thereof a therapeutically effective amount of a compound of the Examples.

Another embodiment is a method for inhibiting CCR2 and CCR5 activity comprising administering to a patient in need thereof a therapeutically effective amount of a compound of the Examples.

Another embodiment is a method for treating inflammatory, allergic, autoimmune, metabolic, cancer and/or cardiovascular diseases, comprising administering to a patient in need thereof a therapeutically effective amount of a compound of the Examples.

Another embodiment is a method for treating disorders, comprising administering to a patient in need thereof a therapeutically effective amount of a compound of the Examples, said disorders being selected from diabetes, obesity, metabolic syndrome, stroke, neuropathic pain, ischemic cardiomyopathy, psoriasis, hypertension, scheroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a method for treating disorders, comprising administering to a patient in need thereof a therapeutically effective amount of a compound of the Examples, wherein said disorders being selected from diabetes, obesity, Crohn's disease, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, and rheumatoid arthritis, restenosis, organ transplantation, and cancer.

Another embodiment is a method for treating disorders, comprising administering to a patient in need thereof a therapeutically effective amount of a compound of the Examples, wherein said disorders being selected from diabetes, obesity, Crohn's disease, systemic lupus erythematosus, glomerulonephritis, multiple sclerosis, atherosclerosis, restenosis, and organ transplantation.

Another embodiment is a method for treating disorders, comprising administering to a patient in need thereof a therapeutically effective amount of a compound of the Examples, wherein said disorders being selected from multiple sclerosis, atherosclerosis, Crohn's disease, and diabetes.

Another embodiment is a method for treating disorders, comprising administering to a patient in need thereof a therapeutically effective amount of a compound of the Examples, wherein said disorders being selected from restenosis, organ transplantation, and cancer.

Another embodiment is a method for treating diabetes, comprising administering to a patient in need thereof a therapeutically effective amount of a compound of the Examples.

Another embodiment is a method for treating multiple sclerosis, comprising administering to a patient in need thereof a therapeutically effective amount of a compound of the Examples.

Another embodiment is a method for treating atherosclerosis, comprising administering to a patient in need thereof a therapeutically effective amount of a compound of the Examples.

Another embodiment is a method for treating restenosis, comprising administering to a patient in need thereof a therapeutically effective amount of a compound of the Examples.

Another embodiment is a method for treating organ transplantation, comprising administering to a patient in need thereof a therapeutically effective amount of a compound of the Examples.

Another embodiment is a method for treating cancer, comprising administering to a patient in need thereof a therapeutically effective amount of a compound of the Examples.

Another embodiment is a method for treating cancer, wherein the cancer is selected from breast cancer, liver cancer, prostate cancer and melanoma.

Another embodiment is a method for treating inflammatory, allergic, autoimmune, metabolic, cancer and/or cardiovascular diseases which are at least partially mediated by CCR-2, comprising administering to a patient in need thereof a therapeutically effective amount of a compound of the Examples.

Another embodiment is a method for modulation of CCR2 activity comprising administering to a patient in need thereof a therapeutically effective amount of a compound of the Examples.

Another embodiment is a method for modulation of MIP-1β and RANTES activity that is mediated by the CCR5 receptor comprising administering to a patient in need thereof a therapeutically effective amount of a compound of the Examples.

Another embodiment is a compound of Examples in the preparation of a medicament for the treatment of diabetes, obesity, metabolic syndrome, stroke, neuropathic pain, ischemic cardiomyopathy, psoriasis, hypertension, scheroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a compound of the Examples for use in therapy.

Another embodiment is a method of preparing the compounds of the examples.

Another embodiment is a compound selected from:
(i) N-((1R,2S,5R)-5-(isopropylamino)-2-((3S)-2-oxo-3-((6-(trifluoromethyl)-4-quinazolinyl)amino)-1-pyrrolidinyl) cyclohexyl)acetamide;
N-((1R,2S,5R)-5-amino-2-((3S)-2-oxo-3-((6-(trifluoromethyl)-4-quinazolinyl)amino)-1-pyrrolidinyl)cyclohexyl) acetamide;
N-((1R,2S,5R)-5-(isopropyl(methyl)amino)-2-((3S)-3-((1-oxido-6-(trifluoromethyl)-4-quinazolinyl)amino)-2-oxo-1-pyrrolidinyl)cyclohexyl)acetamide;
N-((1R,2S,5R)-5-(isopropylamino)-2-((3S)-3-((1-oxido-6-(trifluoromethyl)-4-quinazolinyl)amino)-2-oxo-1-pyrrolidinyl)cyclohexyl)acetamide; and
N-((1R,2S,5R)-5-(tert-butylamino)-2-((3S)-3-((1-oxido-6-(trifluoromethyl)-4-quinazolinyl)amino)-2-oxo-1-pyrrolidinyl)cyclohexyl)acetamide; or
(ii) a pharmaceutically acceptable salt or prodrug or (i) thereof; wherein said compounds are useful as human metabolites of pharmaceutically active compounds.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment (including preferred aspects) are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of the compounds disclosed herein may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young et al., *Antimicrobial Agents and Chemotherapy*, 1995, 2602-2605.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

EXAMPLES

The following Examples illustrate embodiments of the inventive compounds and starting materials, and are not intended to limit the scope of the claims.

As appropriate, reactions were conducted under an atmosphere of dry nitrogen (or argon). For anhydrous reactions, Dri-Solv solvents from EM were employed. For other reactions, reagent grade or HPLC grade solvents were utilized. Unless otherwise stated, all commercially obtained reagents were used as received.

LC/MS measurements were obtained using a Shimadzu HPLC/Waters ZQ single quadropole mass spectrometer hybrid system. Data for the peak of interest are reported from positive-mode electrospray ionization. NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein. For ease of reference, the abbreviations include, but are not necessarily limited to: sat.=saturated, HPLC=high-performance liquid chromatography, AP=area percent, KF=Karl-Fischer, RT=room temperature, mmol=millimoles, HRMS=high-resolution mass spectroscopy, TBTU=O-benzotriazol-2-yl-N,N,N',N'-tetramethyluronium tetrafluoroborate, MTBE=TBME=tert-butyl methyl ether, EDAC=N-(3-dimethylaminopropyl)-N'-ethylcarbodiimide hydrochloride, EDC=N-(3-dimethylaminopropyl)-N'-ethylcarbodiimide, TEA=triethylamine, DPPA=diphenyl phosphoryl azide, IPA=isopropyl alcohol, TFA=trifluoroacetic acid, DCM=dichloromethane, THF=tetrahydrofuran, DMF=N,N-dimethylformamide, BOP=(benzotriazol-1-yloxy)tris(dimethylamino)phosphonium hexafluorophosphate, EtOAc=Ethyl acetate, DMSO=dimethylsulfoxide, ° C.=degrees Celsius, eq=equivalent or equivalents, g=gram or grams, mg=milligram or milligrams, mL (or ml)=milliliter or milliliters, h=hour or hours, M=molar, N=normal, min=minute or minutes, MHz=megahertz, tlc=thin layer chromatography, v/v=volume to volume ratio.

"α", "β", "R" and "S" are stereochemical designations familiar to those skilled in the art.

Example 1

N-((1R,2S,5R)-2-((3S)-3-((6-tert-butylpyrimido[5,4-d]pyrimidin-4-yl)amino)-2-oxo-1-pyrrolidinyl)-5-(isopropyl(methyl)amino)cyclohexyl)acetamide

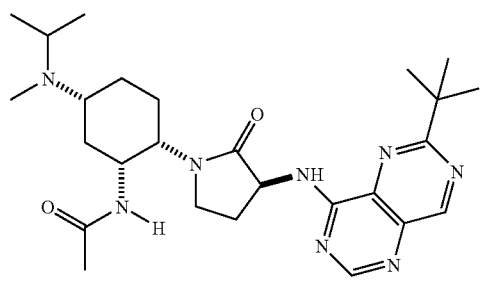

Example 1, Step 1: (1R,2S,5R)-tert-Butyl 2-benzyloxycarbonylamino-7-oxo-6-aza-bicyclo[3.2.1]octane-6-carboxylate (89.6 g, 0.24 mol, see: P. H. Carter, et al. PCT application WO 2005/021500) was dissolved in ethyl acetate (1.5 L) and the resulting solution was washed with sat. NaHCO$_3$ (2×0.45 L) and sat. NaCl (1×0.45 L). The solution was dried (Na$_2$SO$_4$) and then filtered directly into a 3-necked 3 L round-bottom flask. The solution was purged with direct nitrogen injection before being charged with 10% Pd/C (13.65 g) under nitrogen atmosphere. The flask was evacuated and back-filled with hydrogen; this was repeated twice more. Hydrogen was bubbled through the solution for 30 min and then the reaction was stirred under 1 atm H$_2$ for 18 h. The flask was evacuated, back-filled with nitrogen, and charged with fresh catalyst (6 g of 10% Pd/C). Hydrogen was bubbled through the solution for 30 min and then the reaction was stirred under 1 atm H$_2$ for 18 h. The flask was evacuated and back-filled with nitrogen. The mixture was filtered through Celite; the filter pad was then washed with ethyl acetate. The filtrate (~1.6 L EtOAc volume) was diluted with acetonitrile (0.3 L) and charged sequentially with T-N-Cbz-methionine (68 g, 0.24 mol), TBTU (77 g, 0.24 mol), and N,N-diisopropylethylamine (42 mL, 0.24 mol). The reaction was stirred at room temperature for 4 h, during which time it changed from a suspension to a clear solution. The reaction was quenched with the addition of sat. NH$_4$Cl (0.75 L) and water (0.15 L); the mixture was diluted further with EtOAc (0.75 L). The phases were mixed and separated and the organic phase was washed with sat. Na$_2$CO$_3$ (2×0.9 L) and sat. NaCl (1×0.75 L). The solution was dried (Na$_2$SO$_4$), filtered, and concentrated in vacuo to give (1R,2S,5R)-tert-butyl 2-((S)-2-(benzyloxycarbonylamino)-4-(methylthio)butanamido)-7-oxo-6-aza-bicyclo[3.2.1]octane-6-carboxylate as an oil, which was taken into the next step without further purification. LC/MS for primary peak: [M-Boc+H]$^+$=406.3; [M+Na]$^+$=528.3. $^1$H-NMR (400 MHz, d$_4$-MeOH): δ 7.36 (m, 5H), 5.11 (s, 2H), 4.32 (m, 1H), 4.2 (m, 1H), 4.0 (m, 1H), 2.5-2.7 (m, 3H), 2.25 (m, 1H), 2.11 (s, 3H), 2.05 (m, 4H), 1.9 (m, 1H), 1.7 (m, 2H), 1.54 (s, 9H). Also present are EtOAc [1.26 (t), 2.03 (s), 4.12 (q)] and N,N,N,N-tetramethylurea [2.83 (s)].

Example 1, Step 2: A sample of (1R,2S,5R)-tert-butyl 2-((S)-2-(benzyloxycarbonylamino)-4-(methylthio)butanamido)-7-oxo-6-aza-bicyclo[3.2.1]octane-6-carboxylate (0.24 mol assumed; see previous procedure) was dissolved in iodomethane (1,250 g) and stirred for 48 h at room temperature. The reaction was concentrated in vacuo. The residue was dissolved in dichloromethane and concentrated in vacuo. This was repeated twice more. The resultant sludge was dissolved in dichloromethane (0.4 L) and poured into a rapidly stirring solution of MTBE (4.0 L). The resultant yellow solids were collected via suction filtration and dried under high vacuum to afford the sulfonium salt (179 g). This material was taken into the next step without further purification. LC/MS for primary peak: [M-Me$_2$S+H]$^+$=458.4; [M]$^+$=520.4. $^1$H-NMR (400 MHz, d$_4$-MeOH): δ 7.35 (m, 5H), 5.09 (s, 2H), 4.33 (m, 1H), 4.28 (m, 1H), 3.98 (m, 1H), 3.3-3.45 (m, 2H), 2.97 (s, 3H), 2.94 (s, 3H), 2.78 (m, 1H), 2.0-2.3 (m, 4H), 1.7 (m, 2H), 1.52 (s, 9H). Also present are MTBE [1.18 (s), 3.2 (s)] and traces of N,N,N,N-tetramethylurea [2.81 (s)].

Example 1, Step 3: All of the sulfonium salt from the previous step (0.24 mol assumed) was dissolved in DMSO (2.0 L). The resultant solution was stirred under nitrogen at room temperature and charged with cesium carbonate (216 g) portionwise. The suspension was stirred at room temperature for 3 h and then filtered to remove the solids. The solution was divided into ~0.22 L portions and worked up as follows: the reaction mixture (~0.22 L) was diluted with ethyl acetate (1.5 L) and washed successively with water (3×0.5 L) and brine (1×0.3 L). The organic phase was dried (Na$_2$SO$_4$), filtered, and concentrated in vacuo. The desired (1R,2S,5R)-tert-butyl 2-((S)-3-(benzyloxycarbonylamino)-2-oxopyrrolidin-1-yl)-7-oxo-6-azabicyclo[3.2.1]octane-6-carboxylate (90.8 g, 83%) was obtained as a microcrystalline foam, free from tetramethyl urea impurity. LC/MS for primary peak: [M-Boc+H]$^+$=358.4; [M+Na]$^+$=480.4. $^1$H-NMR (400 MHz, d$_4$-MeOH): δ 7.35 (m, 5H), 5.12 (s, 2H), 4.35 (m, 2H), 4.2 (m, 1H), 3.6 (m, 1H), 3.3 (m, 1H), 2.64 (m, 1H), 2.28-2.42 (m, 2H), 2.15 (m, 1H), 1.7-2.0 (m, 5H), 1.55 (s, 9H). If desired, this material can be isolated as a solid by dissolving in MTBE (1 volume), adding to heptane (3.3 volumes), and collecting the resultant precipitate.

Example 1, Step 4: A stirring solution of (1R,2S,5R)-tert-butyl 2-((S)-3-(benzyloxycarbonylamino)-2-oxopyrrolidin-1-yl)-7-oxo-6-azabicyclo[3.2.1]octane-6-carboxylate (108 g, 0.236 mol) in THF (1 L) was charged with lithium hydroxide monohydrate (21.74 g, 0.519 mol). Water (0.3 L) was added slowly, such that the temperature did not exceed 20° C. The reaction was stirred at room temperature overnight and the volatiles were removed in vacuo. The pH was adjusted to ~4 through the addition of 1N HCl (450 mL) and NaH$_2$PO$_4$. The resultant white precipitates were collected by filtration and washed with water (2×1 L). The solid was dissolved in dichloromethane (1.5 L) and water (~1 L). The organic layer was dried (Na$_2$SO$_4$), filtered, and concentrated in vacuo. The residue was dissolved in EtOAc (0.7 L) and the resultant solution was heated at reflux for 1 h. Solids separated after cooling to RT, and were collected via filtration. These solids were purified by recrystallization in isopropanol to afford the desired (1R,2S,5R)-2-((S)-3-(benzyloxycarbonylamino)-2-oxopyrrolidin-1-yl)-5-(tert-butoxycarbonylamino)cyclohexanecarboxylic acid as a white solid (104.5 g, 93% yield). LC/MS for primary peak: [M-tBu+H]$^+$=420.2; [M-Boc+H]$^+$=376.2; [M+H]$^+$=476.2. $^1$H-NMR (400 MHz, d$_4$-MeOH): δ 7.35 (m, 5H), 5.11 (s, 2H), 4.35 (m, 2H), 3.71 (m, 1H), 3.45-3.6 (m, 2H), 2.99 (m, 1H), 2.41 (m, 1H), 2.15 (m, 1H), 2.0 (m, 2H), 1.6-1.9 (m, 4H), 1.46 (s, 9H).

Example 1, Step 5: A 3 L round bottom flask was charged with (1R,2S,5R)-2-((S)-3-(benzyloxycarbonylamino)-2-oxopyrrolidin-1-yl)-5-(tert-butoxycarbonylamino)cyclohexanecarboxylic acid (75.5 g, 0.158 mol), EDC.HCl (33.5 g, 0.175 mol), 1-hydroxybenzotriazole (23.6 g, 0.175 mol), and dichloromethane (1 L). The reaction was stirred at room temperature for 2 h, during which time it changed from a white suspension to a clear solution. Ammonia (gas) was bubbled into the solution until the pH was strongly basic (paper) and the reaction was stirred for 10 min; this ammonia addition was repeated and the reaction was stirred for an additional 10 min. Water was added. The organic phase was washed with sat. NaHCO$_3$, NaH$_2$PO$_4$, and brine before being concentrated in vacuo. The residue was slurried with acetonitrile (0.5 L) and then concentrated in to give (1R,2S,5R)-2-((S)-3-(benzyloxycarbonylamino)-2-oxopyrrolidin-1-yl)-5-(tert-butoxycarbonylamino)cyclohexanecarboxamide as a white solid (75.9 g, ~100%), which was used in the next step without further purification. LC/MS for primary peak: [M-Boc+H]$^+$=375.3; [M+H]$^+$=475.4; [M-tBu+H]$^+$=419.3. $^1$H-NMR (400 MHz, d-MeOH): δ 7.35 (m, 5H), 5.11 (s, 2H), 4.25 (m, 2H), 3.70 (m, 1H), 3.6 (m, 1H), 3.45 (m, 1H), 2.91 (m, 1H), 2.38 (m, 1H), 2.12 (m, 1H), 1.9-2.05 (m, 2H), 1.65-1.9 (m, 4H), 1.46 (s, 9H).

Example 1, Step 6: The reaction was run in three equal portions and combined for aqueous workup. A 5 L, 3-necked round bottom flask was charged with (1R,2S,5R)-2-((S)-3-(benzyloxycarbonylamino)-2-oxopyrrolidin-1-yl)-5-(tert-butoxycarbonylamino)cyclohexanecarboxamide (25.3 g, 53 mmol), acetonitrile (1.9 L), and 2.6 L of water/ice. The mixture was stirred and cooled to 0° C. Iodobenzene diacetate (25.77 g, 80 mmol) was added and the reaction was stirred for 2 h; another 0.5 eq of iodobenzene diacetate was added. The reaction was stirred for 9 h (reaction temp<10° C.). The mixture was charged with 8 eq N,N-diisopropylethylamine and 2 eq acetic anhydride. Over the next thirty minutes, 4 eq N,N-diisopropylethylamine and 2 eq acetic anhydride were added every ten minutes, until the reaction had proceeded to completion (HPLC). The acetonitrile was removed in vacuo; some solid separated from the residue, and this was collected by filtration. The remaining residue was extracted with dichloromethane (3 L, then 1 L). The organic phase was washed sequentially with water, sat. $NaHCO_3$, and brine. The collected solids were added to the organic phase, along with activated carbon (15 g). The mixture was stirred for 30 minutes at 40° C. before being filtered and concentrated in vacuo. The residue was dissolved in EtOAc (1 L), and the resultant solution was stirred at 75° C. for 1 h before being allowed to cool to room temperature. A solid separated and was collected by filtration. This solid was purified further by recrystallization: it was first dissolved in 0.5 L $CH_2Cl_2$, then concentrated in vacuo, then re-crystallized from 1 L EtOAc; this was repeated three times. The solids obtained from the mother liquors of the above were recrystallized three times using the same method. The combined solids were recrystallized twice more from acetonitrile (0.7 L) to provide 66 g (84%) of tert-butyl (1R,3R,4S)-3-acetamido-4-((S)-3-(benzyloxycarbonylamino)-2-oxopyrrolidin-1-yl)cyclohexylcarbamate (purity>99.5% by HPLC). LC/MS for primary peak: $[M+H]^+$=489.4; $[M-tBu+H]^+$=433.3. $^1$H-NMR (400 MHz, $d_4$-MeOH): δ 7.3-7.4 (m, 5H), 5.11 (s, 2H), 4.35 (m, 1H), 4.15 (m, 1H), 4.04 (m, 1H), 3.8 (m, 1H), 3.6 (m, 2H), 2.44 (m, 1H), 2.12 (m, 1H), 1.87-2.05 (m, 4H), 1.87 (s, 3H), 1.55-1.7 (m, 2H), 1.46 (s, 9H). The stereochemical fidelity of the Hofmann rearrangement was confirmed through X-ray crystal structure analysis of this compound, as shown in FIG. 1.

Example 1, Step 7: A stirring solution of tert-butyl (1R,3R,4S)-3-acetamido-4-((S)-3-(benzyloxycarbonylamino)-2-oxopyrrolidin-1-yl)cyclohexylcarbamate (66 g, 0.135 mol) in dichloromethane (216 mL) was charged with trifluoroacetic acid (216 mL). The reaction was stirred for 2 h at room temperature and concentrated in vacuo. The residue was dissolved in methanol and the resultant solution was concentrated in vacuo; this was repeated once. Benzyl (S)-1-((1S,2R,4R)-2-acetamido-4-aminocyclohexyl)-2-oxopyrrolidin-3-ylcarbamate was obtained as an oil and used directly in Step 8 below. LC/MS found $[M+H]^+$=389.4. $^1$H-NMR (400 MHz, $d_4$-MeOH): δ 7.3-7.4 (m, 5H), 5.12 (s, 2H), 4.41 (br. s, 1H), 4.15 (m, 1H), 4.00 (t, J=9.3 Hz, 1H), 3.81 (t, J=9.1 Hz, 1H), 3.65 (q, J=8.4 Hz, 1H), 3.3-3.4 (m, 1H), 2.45 (m, 1H), 1.95-2.24 (m, 5H), 2.00 (s, 3H), 1.6-1.8 (m, 2H).

Example 1, Step 8: A stirring solution of benzyl (S)-1-((1S,2R,4R)-2-acetamido-4-aminocyclohexyl)-2-oxopyrrolidin-3-ylcarbamate (~0.135 mol) in methanol (675 mL) was charged sequentially with acetone (37.8 g, 4 eq), sodium acetate (33.2 g, 3 eq), and sodium cyanoborohydride (16.9 g, 2 eq). The mixture was stirred at room temperature for 6 h and filtered. The filtrate was dissolved in dichloromethane (1 L); this solution was washed with 1N NaOH (1 L). The solids collected in the filtration were dissolved in 1N NaOH (1 L) at 0° C. and then extracted with dichloromethane (1 L). The organic extracts were combined and extracted with aqueous HCl (200 mL 1N HCl+800 mL water). The aqueous phase was basified with sat. $NaHCO_3$ (500 mL) and then 1N NaOH (100 mL) until pH 11. The aqueous phase was extracted with dichloromethane (2 L). The organic extracts were combined, dried ($Na_2SO_4$), filtered, and concentrated in vacuo to give benzyl (S)-1-((1S,2R,4R)-2-acetamido-4-(isopropylamino)cyclohexyl)-2-oxopyrrolidin-3-ylcarbamate as an oil. LC/MS found $[M+H]^+$=431.45. $^1$H-NMR (400 MHz, $d_4$-MeOH): δ 7.3-7.4 (m, 5H), 5.12 (s, 2H), 4.31 (m, 1H), 4.24 (t, J=9.4 Hz, 1H), 4.11 (m, 1H), 3.61 (t, J=9.1 Hz, 1H), 3.52 (q, J=8.6 Hz, 1H), 3.04 (br. s, 1H), 2.96 (sep, J=6.3 Hz, 1H), 2.40 (m, 1H), 2.15 (m, 1H), 1.92 (s, 3H), 1.7-1.9 (m, 5H), 1.65 (m, 1H), 1.12 (app. dd, J=6.3, 1.1 Hz, 6H).

Example 1, Step 9 (See Alternative Step 9, below): A stirring solution of benzyl (S)-1-((1S,2R,4R)-2-acetamido-4-(isopropylamino)cyclohexyl)-2-oxopyrrolidin-3-ylcarbamate (~115 mmol) in dichloromethane (600 mL) was cooled to 0° C. and charged sequentially with formaldehyde (18.6 g, 37 wt % solution), triethylamine (23 mL), and sodium triacetoxyborohydride (28.7 g). The mixture was stirred at room temperature for 30 minutes and diluted with dichloromethane (up to 1.2 L). This solution was washed thrice with 500 mL sat. $NaHCO_3$+NaOH (sat. $NaHCO_3$, pH to 11 w/1N NaOH). The organic layer was extracted with aq. HCl (200 mL 1N HCl+600 mL water). The aqueous phase was basified with sat. $NaHCO_3$ (500 mL) and then 1N NaOH (100 mL) until pH 11. The aqueous phase was extracted with dichloromethane (1.2 L). The organic extracts were combined, dried ($Na_2SO_4$), filtered, and concentrated in vacuo to give benzyl (S)-1-((1S,2R,4R)-2-acetamido-4-(isopropyl(methyl)amino)cyclohexyl)-2-oxopyrrolidin-3-ylcarbamate as an oil, which was used directly in Step 10 below. LC/MS found $[M+H]^+$=445.4. $^1$H-NMR (400 MHz, $d_4$-MeOH): δ 7.3-7.4 (m, 5H), 5.12 (s, 2H), 4.33 (br s, 1H), 4.25 (t, J=9.2 Hz, 1H), 4.11 (br s, 1H), 3.5-3.6 (m, 2H), 2.77 (v br s, 2H), 2.41 (m, 1H), 2.26 (s, 3H), 2.0-2.1 (m, 2H), 1.92 (s, 3H), 1.7-1.9 (m, 5H), 1.10 (app. dd, J=17, 6.4 Hz, 6H).

Example 1, Step 10: To a solution of benzyl (S)-1-((1S,2R,4R)-2-acetamido-4-(isopropyl(methyl)amino)-cyclohexyl)-2-oxopyrrolidin-3-ylcarbamate (~0.115 mol) in methanol (600 mL) was added 10% Pd/C (6 g of 50% wet catalyst). The flask was evacuated and back-filled with hydrogen. The mixture was stirred under 1 atm $H_2$ for 2 h and the catalyst was removed by filtration through Celite. The filtrate was concentrated in vacuo to provide N-((1R,2S,5R)-2-((S)-3-amino-2-oxopyrrolidin-1-yl)-5-(isopropyl(methyl)amino)cyclohexyl)acetamide as an oil, which was taken on to the next step without further purification. LC/MS found $[M+H]^+$=311.47. $^1$H-NMR (400 MHz, $d_4$-MeOH): δ 4.39 (br s, 1H), 4.00 (m, 1H), 3.3-3.5 (m, 4H), 2.73 (m, 1H), 2.38 (m, 1H), 2.25 (s, 3H), 2.0-2.2 (m, 3H), 1.94 (s, 3H), 1.6-1.75 (m, 4H), 1.07 (app. dd, J=21, 6.4 Hz, 6H).

Example 1, Step 11: To a solution of N-((1R,2S,5R)-2-((S)-3-amino-2-oxopyrrolidin-1-yl)-5-(isopropyl(methyl)amino)cyclohexyl)acetamide (62 mg, 0.2 mmol) in isopropanol (3 mL) was added 2-tert-Butyl-8-chloro-pyrimido[5,4-d]pyrimidine (49 mg, 1.1 eq, see: P. H. Carter et al., PCT application WO 2005/021500) and triethylamine (40.4 mg, 2 eq). The mixture was stirred at room temperature for 1 h. The solvent was removed under reduced pressure. The residue was purified with preparative HPLC to provide the title compound as its TFA salt (125 mg, 86.3%). LC/MS found $[M+H]^+$=497. $^1$H-NMR (400 MHz, $CD_3OD$), δ ppm: 9.31 (1H, s), 8.67 (1H, s), 5.07 (1H, t, J=9.92 Hz), 4.14-4.31 (2H, m), 3.57-3.89 (4H, m), 2.78 (3H, s), 2.58-2.67 (1H, m), 2.38-2.50 (1H, m), 1.94-2.29 (6H, m), 1.92 (3H, s), 1.51 (9H, s), 1.41 (3H, d, J=6.61 Hz), 1.34 (3H, dd, J=6.36, 3.81 Hz).

Example 2

N-((1R,2S,5R)-5-(isopropylamino)-2-((3S)-2-oxo-3-((6-(trifluoromethyl)-4-quinazolinyl)amino)-1-pyrrolidinyl)cyclohexyl)acetamide

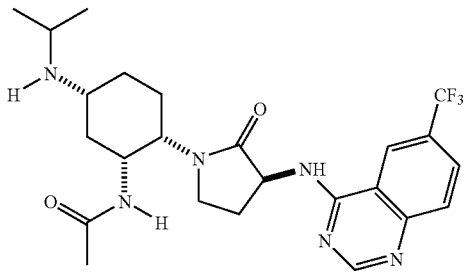

Example 2, Step 1: To a solution of benzyl (S)-1-((1S,2R,4R)-2-acetamido-4-(isopropylamino)cyclohexyl)-2-oxopyrrolidin-3-ylcarbamate (30 mg, 0.07 mmol; see Example 1, Step 8) in methanol (3 mL) was added 10% Pd/C (30 mg of 50% wet catalyst). The flask was evacuated and back-filled with hydrogen from a hydrogen balloon. The mixture was stirred at room temperature for 1.5 h under 1 atm hydrogen and then the catalyst was removed by filtration. The filtrate was concentrated in vacuo. The residue was dissolved in isopropanol (3 mL) and charged sequentially with 4-chloro-6-(trifluoromethyl)quinazoline (19.4 mg, 1.2 eq) and diisopropylethylamine (18 mg, 2 eq). The mixture was stirred at room temperature for 1 h. The solvent was removed under reduced pressure. The residue was purified by preparative reverse-phase HPLC to provide the title compound as its TFA salt (47 mg, 93%). LC/MS found [M+H]$^+$=493. $^1$H-NMR (400 MHz, CD$_3$OD), δ ppm: 8.90 (1H, s), 8.81 (1H, s), 8.25-8.29 (1H, m), 7.96 (1H, d, J=8.65 Hz), 5.44 (1H, t, J=9.92 Hz), 4.42 (1H, d, J=2.54 Hz), 4.15-4.24 (1H, m), 3.90 (1H, t, J=8.65 Hz), 3.70-3.79 (1H, m), 3.46-3.62 (2H, m), 2.56-2.67 (1H, m), 2.33-2.47 (1H, m), 1.70-2.23 (9H, m), 1.35 (6H, d, J=6.10 Hz).

Example 3

N-((1R,2S,5R)-5-(methylamino)-2-((3S)-2-oxo-3-((6-(trifluoromethyl)-4-quinazolinyl)amino)-1-pyrrolidinyl)cyclohexyl)acetamide

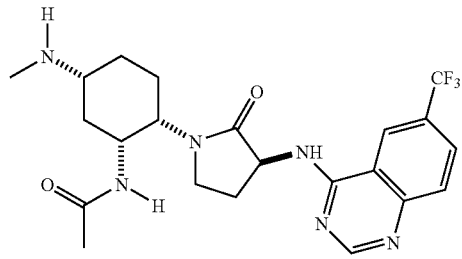

Example 3, Step 1: A sample of tert-butyl (1R,3R,4S)-3-acetamido-4-((S)-3-(benzyloxycarbonylamino)-2-oxopyrrolidin-1-yl)cyclohexylcarbamate (43.2 g, 88 mmol; see Example 1, Step 6 was dissolved in dichloromethane (200 mL). The solution was charged with TFA (100 mL), stirred for 2.5 h, and concentrated in vacuo. The residue was re-dissolved in dichloromethane (200 mL) and the resultant solution was added dropwise to a stirring solution of pure diethyl ether (2.0 L). The white solid was collected with ether washes and then dissolved in a basic saline solution (2.0 M in NaCl and 1.0 M in K$_2$CO$_3$, 350 mL total). Dichloromethane (1.2 L) was added, and the two phases were mixed vigorously before being separated. The aqueous phase was extracted with dichloromethane (3×450 mL). The organic extracts were combined, dried (MgSO$_4$), filtered, and concentrated in vacuo to afford benzyl (S)-1-((1S,2R,4R)-2-acetamido-4-aminocyclohexyl)-2-oxopyrrolidin-3-ylcarbamate (34.8 g, quantitative) as a microcrystalline solid after pumping on high vacuum. LC/MS found [M+H]$^+$=389.5.

Example 3, Step 2: A sample of benzyl (S)-1-((1S,2R,4R)-2-acetamido-4-aminocyclohexyl)-2-oxopyrrolidin-3-ylcarbamate (34.8 g, ca. 90 mmol) was dissolved in methanol (400 ml). The flask was purged with nitrogen and charged with triethylamine (15.61 ml, 112 mmol), followed by 4-methoxybenzaldehyde (13.62 ml, 112 mmol). The reaction was stirred at RT for 14 h, at which time LC/MS of reaction showed complete consumption of primary amine and formation of desired imine (LC/MS found [M+H]$^+$=507.4). The reaction was cooled to 0° C. and charged with sodium borohydride (5.08 g, 134 mmol) in portions over 1 minute. The ice bath was removed after 30 min and the solution stirred for an additional 3.5 h. The reaction was concentrated in vacuo to give a white solid/gum, which was dissolved in 400 mL sat. NaHCO$_3$ and 1200 mL EtOAc. The phases were mixed vigorously and then separated. The organic phase was washed 2×800 mL 0.5N HCl (note: a small third, oily phase was on the bottom in the first extraction; took along with the acid phase). The acid washes were combined, basified with solid NaOH to pH 13, cooled to RT, and then extracted with EtOAc (1×1000 mL; 2×600 mL). The organic extracts were combined, washed with brine (1×120 mL), dried (MgSO$_4$), filtered, and concentrated in vacuo. The residue was dissolved in dichlormethane and concentrated; this procedure was repeated to give benzyl (S)-1-((1S,2R,4R)-2-acetamido-4-(4-methoxybenzylamino)cyclohexyl)-2-oxopyrrolidin-3-ylcarbamate (43.68 g, 86 mmol, 96% yield) as a flowing microcrystalline solid after pumping on high vacuum. LC/MS found [M+H]$^+$=509.6.

Example 3, Step 3: A sample of benzyl (S)-1-((1S,2R,4R)-2-acetamido-4-(4-methoxybenzylamino)cyclohexyl)-2-oxopyrrolidin-3-ylcarbamate (54.45 g, 107 mmol) was dissolved in dichloromethane (400 mL). The resultant solution was cooled to 0° C. under N$_2$ stream and then charged sequentially with triethylamine (29.8 mL, 214 mmol), aqueous formaldehyde (11.96 mL of a 37% solution, 161 mmol), and sodium triacetoxyborohydride (34.0 g, 161 mmol). The ice bath was removed and the reaction was stirred at RT for 2 h before being diluted with 750 mL EtOAc and washed with sat. NaHCO$_3$ (2×250 mL). The organic phase was concentrated in vacuo and the resultant residue was dissolved in EtOAc (750 mL). The organic phase was washed with acid [2×(200 mL 1N HCl/300 mL H$_2$O)]. The acidic washes were combined and then basified with 6N NaOH (80 mL) and sat. NaHCO$_3$ (70 mL). The mixture was extracted with EtOAc (3×500 mL). The organic extracts were combined, washed with brine (1×100 mL), dried (MgSO$_4$), filtered, and concentrated in vacuo. The residue was dissolved in methylene chloride and concentrated; this was repeated twice to afford benzyl (S)-1-((1S,2R,4R)-2-acetamido-4-((4-methoxybenzyl)(methyl)amino)cyclohexyl)-2-oxopyrrolidin-3-ylcarbamate (54.14 g, 104 mmol, 97% yield) as a hard white microcrystalline foam after pumping on high vacuum. LC/MS found [M+H]$^+$=523.6.

Example 3, Step 4: A sample of benzyl (S)-1-((1S,2R,4R)-2-acetamido-4-((4-methoxybenzyl)(methyl)amino)cyclohexyl)-2-oxopyrrolidin-3-ylcarbamate (25.0 g, 47.8 mmol) was dissolved in MeOH. The flask was charged with dihydroxypalladium (6 g, 8.54 mmol), evacuated, and back filled with hydrogen from a hydrogen balloon. The mixture was stirred at RT overnight and then filtered (3×80 mL isopropanol washes). The residue was concentrated under high vacuum to dryness. The residue was dried azeotropically with iso-propanol (4×150 mL) under reduced pressure to afford N-((1R,2S,5R)-2-((S)-3-amino-2-oxopyrrolidin-1-yl)-5-(methylamino)cyclohexyl)acetamide (12.5 g, 46.6 mmol, 97% yield). LC/MS found [M+H]$^+$=269.

Example 3, Step 5: To a solution of N-((1R,2S,5R)-2-((S)-3-amino-2-oxopyrrolidin-1-yl)-5-(methylamino)cyclohexyl)acetamide (12.5 g, 46.6 mmol) in dichloromethane was added triethylamine (12.98 mL, 93 mmol) and 4-chloro-6-(trifluoromethyl)quinazoline (10.83 g, 46.6 mmol). The mixture was stirred at room temperature overnight and then concentrated under reduced pressure to dryness. The residue was dissolved in dichloromethane (350 mL) and extracted with a solution of aqueous acetic acid (1×200 mL, 1×100 mL; made from 300 mL of H$_2$O and 16 mL of acetic acid. The acidic aqueous layer (pH 4-5) was extracted with dichloromethane (2×300 mL), basified with Na$_2$CO$_3$ to pH 10-11, and then extracted with dichloromethane (2×350 mL; maintained pH of aqueous layer at 10-11 with Na$_2$CO$_3$ as necessary). The organic phase was washed with saturated NaCl solution (1×200 mL); the NaCl layer was back-extracted with dichloromethane (1×100 mL). The organic extracts were combined, dried (Na$_2$SO$_4$), filtered, and concentrated in vacuo to give the title compound (19.4 g, 90%). LC/MS found [M+H]$^+$=465. HPLC shows the purity as 99.4%, with the largest single impurity as 0.5%. $^1$H-NMR (500 MHz, CD$_3$OD), δ ppm: 8.77 (1H, s), 8.56 (1H, s), 8.02 (1H, dd, J=8.80, 1.37 Hz), 7.87 (1H, d, J=8.52 Hz), 5.25 (1H, t, J=8.52 Hz), 4.53 (1H, q, J=3.94 Hz), 4.01 (1H, dt, J=11.96, 3.85, 3.71 Hz), 3.46-3.64 (2H, m), 2.77-2.86 (1H, m), 2.47-2.57 (1H, m), 2.41 (3H, s), 2.22 (1H, dq, J=12.51, 12.44, 3.57 Hz), 1.98 (3H, s), 1.95-1.98 (1H, m), 1.92-1.98 (1H, m), 1.84-1.91 (1H, m), 1.78 (1H, t, J=3.44 Hz), 1.71-1.76 (1H, m), 1.62-1.69 (1H, m).

Example 3, Recrystallization: A sample of the title compound (19.4 g) from Step 5 was added to 300 mL of absolute ethanol. The mixture was brought to reflux under nitrogen atmosphere, resulting in complete dissolution of solid, and then cooled slowly to ~60° C. with stirring (some solid formed before concentration). The mixture was concentrated slowly under reduced pressure with stirring (oil bath maintained ~64° C.) until the total weight of the product and ethanol was ~62 g. A substantial amount of solid precipitated during the concentration. The mixture was cooled down to RT slowly and then cooled in an ice bath for 1 h. The cold mixture was filtered and the solid was washed with cold ethanol (~15 mL). The solid was dried at 55-60° C. overnight under reduced pressure to afford the free base of the title compound (17.4 g; 90% recovery). HPLC shows the purity as 99.9%.

Example 4

N-((1R,2S,5R)-5-amino-2-((3S)-2-oxo-3-((6-(trifluoromethyl)-4-quinazolinyl)amino)-1-pyrrolidinyl)cyclohexyl)acetamide

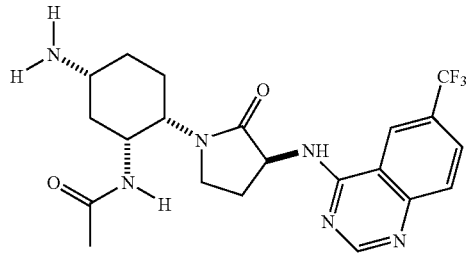

Example 4, Step 1: To a solution of tert-butyl (1R,3R,4S)-3-acetamido-4-((S)-3-(benzyloxycarbonylamino)-2-oxopyrrolidin-1-yl)cyclohexylcarbamate (1.7 g, 3.48 mmol; see Example 1, Step 6) in methanol (10 mL) was added 10% Pd/C (0.6 g of 50% wet catalyst). The flask was evacuated and back-filled with hydrogen with a hydrogen balloon. The mixture was stirred at room temperature under 1 atm of hydrogen for 14 h and the catalyst was removed by filtration. The filtrate was concentrated in vacuo to provide tert-butyl (1R,3R,4S)-3-acetamido-4-((S)-3-amino-2-oxopyrrolidin-1-yl)cyclohexylcarbamate, which was taken on to the next step without further purification. LC/MS found [M+H]$^+$=355.

Example 4, Step 2: To a solution of tert-butyl (1R,3R,4S)-3-acetamido-4-((S)-3-amino-2-oxopyrrolidin-1-yl)cyclohexylcarbamate (~3.4 mmol) in isopropanol (10 mL) was added 4-chloro-6-(trifluoromethyl)quinazoline (0.97 g, 1.2 eq) and diisopropylethylamine (0.88 g, 2 eq). The mixture was stirred at room temperature for 2.5 h. The solvent was removed under reduced pressure. The residue was purified with silica gel column chromatography eluting with 1% and 5% MeOH in dichloromethane to provide tert-butyl (1R,3R,4S)-3-acetamido-4-((S)-2-oxo-3-(6-(trifluoromethyl)quinazolin-4-ylamino)pyrrolidin-1-yl)cyclohexylcarbamate (2.0 g, ~100%). LC/MS found [M+H]$^+$=551.

Example 4, Step 3: A stirring solution of tert-butyl (1R,3R,4S)-3-acetamido-4-((S)-2-oxo-3-(6-(trifluoromethyl)quinazolin-4-ylamino)pyrrolidin-1-yl)cyclohexylcarbamate (1.65 g, 3 mmol) in dichloromethane (8 mL) was charged with trifluoroacetic acid (4 mL). The reaction was stirred for 1 h at room temperature and concentrated in vacuo. The residue was dissolved in a mixture of 1 mL of methanol and 5 mL of dichloromethane. The resulting solution was added dropwise to 80 mL of t-butylmethylether with stirring. The solid formed was collected with filtration and dried to give the title compound as its TFA salt (1.75 g, 86%). LC/MS found [M+H]$^+$=451. $^1$H-NMR (400 MHz, CD$_3$OD), δ ppm: 8.82 (1H, s), 8.77 (1H, s), 8.20-8.27 (1H, m), 7.95 (1H, d, J=8.65 Hz), 5.32 (1H, t, J=9.92 Hz), 4.36 (1H, t, J=4.07 Hz), 4.16-4.23 (1H, m), 3.87 (1H, t, J=9.16 Hz), 3.70-3.79 (1H, m), 3.39 (1H, s), 2.54-2.67 (1H, m), 2.32-2.45 (1H, m), 2.08-2.23 (2H, m), 1.88-2.04 (6H, m), 1.73-1.87 (1H, m).

Example 5

N-((1R,2S,5R)-5-(isopropyl(methyl)amino)-2-((3S)-3-((1-oxido-6-(trifluoromethyl)-4-quinazolinyl)amino)-2-oxo-1-pyrrolidinyl)cyclohexyl)acetamide

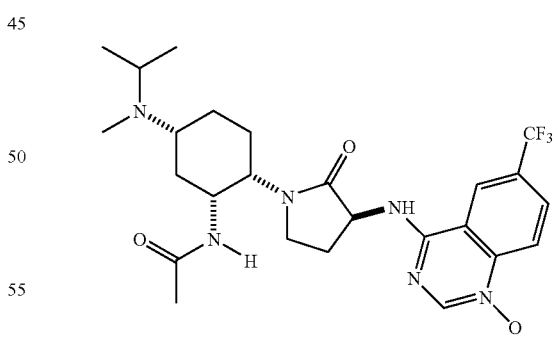

Example 5, Step 1: A sample of tert-butyl (1R,3R,4S)-3-acetamido-4-((S)-2-oxo-3-(6-(trifluoromethyl)quinazolin-4-ylamino)pyrrolidin-1-yl)cyclohexylcarbamate (see Example 4, Step 2) was purified by reverse-phase HPLC. The resultant TFA salt was dissolved in EtOAc and washed successively with 1N NaOH and sat. NaCl. The organic extracts were dried (Na$_2$SO$_4$), filtered, and concentrated in vacuo. The resultant free base (117 mg, 0.21 mmol) was dissolved in methylene chloride (4 mL) and the resultant solution was charged with meta-chloroperoxybenzoic acid (105 mg of 77% purity commercial reagent). The solution turned yellow within 5 min. The reaction was stirred for 3 h before being quenched with the addition of aq. Na$_2$S$_2$O$_3$. The mixture was diluted with EtOAc and the layers were separated. The organic phase was washed successively with sat. NaHCO$_3$ and brine before being dried (Na$_2$SO$_4$), filtered, and concentrated in vacuo to afford 4-((S)-1-((1S,2R,4R)-2-acetamido-4-(tert-butoxycarbonylamino)cyclohexyl)-2-oxopyrrolidin-3-ylamino)-6-(trifluoromethyl)quinazoline 1-oxide as a yellow solid. LC/MS found [M+H]$^+$=567. The entirety of this material was dissolved in methylene chloride (6 mL) and treated with trifluoroacetic acid (2.5 mL). The resultant solution was allowed to stand for 3 h before being concentrated in vacuo. The residue was re-dissolved in methylene chloride (6 mL) and treated with trifluoroacetic acid (2.5 mL). The resultant solution was allowed to stand for 0.5 h before being concentrated in vacuo. The residue was purified by reverse-phase HPLC to afford the TFA salt of 4-((S)-1-((1S,2R,4R)-2-acetamido-4-aminocyclohexyl)-2-oxopyrrolidin-3-ylamino)-6-(trifluoromethyl) quinazoline 1-oxide as a yellow powder (13.6 mg) after lypholization. LC/MS found [M+H]$^+$=467.3.

Example 5, Step 2: A sample of 4-((S)-1-((1S,2R,4R)-2-acetamido-4-aminocyclohexyl)-2-oxopyrrolidin-3-ylamino)-6-(trifluoromethyl)quinazoline 1-oxide (TFA salt, 13.6 mg) was dissolved in 2 mL of 1:1 acetone/methanol and the resultant solution was charged with sodium cyanoborohydride (0.3 mL of a 0.1 M solution in methanol). LC/MS analysis after 1.5 h shows consumption of starting material and conversion to 4-((S)-1-((1S,2R,4R)-2-acetamido-4-(isopropylamino)cyclohexyl)-2-oxopyrrolidin-3-ylamino)-6-(trifluoromethyl)quinazoline 1-oxide, MS found [M+H]$^+$=509.3. This material was not isolated by rather reacted further: the solution was charged with 37% aq. formaldehyde (0.06 mL) and stirred for 30 min, at which point LC/MS analysis showed production of the desired 4-((S)-1-((1S,2R,4R)-2-acetamido-4-(isopropyl(methyl)amino)cyclohexyl)-2-oxopyrrolidin-3-ylamino)-6-(trifluoromethyl)quinazoline 1-oxide, [M+H]$^+$=523.3. The volume was reduced by nitrogen stream and the resultant residue was purified by reverse-phase HPLC to afford the TFA salt of the title compound as a yellow powder (1.7 mg). LC/MS found [M+H]$^+$=523.3.

Alternative Preparation of Example 5

Example 5, Alternative Preparation, Step 1: A sample of 4-chloro-6-(trifluoromethyl)quinazoline (3.25 g, 13.97 mmol) was dissolved in acetonitrile (60 mL) under N$_2$ atmosphere. The resultant cloudy solution was charged with Cs$_2$CO$_3$ (6.83 g, 20.96 mmol) and phenol (1.578 g, 16.77 mmol) and stirred at room temperature. After ~65 hours, the reaction was filtered to remove the solids. The organic phase was concentrated in vacuo to yield an orange solid. The material was purified by automated flash chromatography (80 g silica gel) using 1:3 EtOAc/Hexanes as the eluant to afford the desired 4-phenoxy-6-(trifluoromethyl)quinazoline as a crystalline solid. LC/MS found (M+H)$^+$=291.1.

Example 5, Alternative Preparation, Step 2: To a solution of 4-phenoxy-6-(trifluoromethyl)quinazoline (1.61 g, 5.55 mmol) in anhydrous CH$_2$Cl$_2$ (20 ml) was added 3-chlorobenzoperoxoic acid (1.243 g, 5.55 mmol) and the mixture was stirred at RT for 5 h. At this point, white solids started to precipitate. The reaction was quenched with several drops of Me$_2$S. To the mixture was added 40 mL of hexane to precipitate the undesired 2-hydroxy-4-phenoxy-6-(trifluoromethyl) quinazoline 1-oxide (0.43 g), which was collected by filtration. The filtrate was concentrated to precipitate desired 4-phenoxy-6-(trifluoromethyl)quinazoline 1-oxide (0.93 g), contaminated with benzoic acid by-products and ca. 15% of 2-hydroxy-4-phenoxy-6-(trifluoromethyl)quinazoline 1-oxide. This material was used without further purification for subsequent chemistry. LC/MS found (M+H)$^+$=307.06.

Example 5, Alternative Preparation, Step 3: To a solution of N-((1R,2S,5R)-2-((S)-3-amino-2-oxopyrrolidin-1-yl)-5-(isopropyl(methyl)amino)cyclohexyl)acetamide (50 mg, 0.161 mmol; see Example 1, Step 10) and 4-phenoxy-6-(trifluoromethyl)quinazoline 1-oxide (99 mg, 0.161 mmol) in i-PrOH (2 ml) was added N,N-diisopropylethylamine (0.056 ml, 0.322 mmol). The vessel was sealed under argon and heated in a microwave for 1 hr at 120° C. LC/MS found: (M+H)$^+$=523.3 as the major product peak. The mixture was concentrated and purified by automated flash chromatography (40 g silica gel, eluting with 8:92 10% cNH$_4$OH/MeOH). The fractions containing the desired product were pooled and concentrated in vacuo. The residue was crystallized from CH$_2$Cl$_2$ and hexane. The two crops were combined and dried under vacuum to afford the title compound, 4-((S)-1-((1S,2R,4R)-2-acetamido-4-(isopropyl(methyl)amino)cyclohexyl)-2-oxopyrrolidin-3-ylamino)-6-(trifluoromethyl)quinazoline 1-oxide (93 mg). Analysis by $^1$H-NMR showed that this material contained ~0.75 molar equivalents of CH$_2$Cl$_2$. $^1$H-NMR (400 MHz, d$_4$-MeOH): δ 8.99 (s, 1H), 8.81 (s, 1H), 8.62 (d, J=8.9 Hz, 1H), 8.32 (dd, J=9.0, 1.5 Hz, 1H), 5.28 (t, J=8.4 Hz, 1H), 4.59 (br s, 1H), 4.05 (m, 1H), 3.55-3.65 (m, 2H), 3.43 (m, 1H), 2.75 (br s, 1H), 2.55 (m, 1H), 2.27 (s, 3H), 2.1-2.3 (m, 3H), 2.02 (s, 3H), 2.0 (m, 1H), 1.65-1.7 (m, 3H), 1.12 (d, J=6.0 Hz, 3H), 1.06 (d, J=6.0 Hz, 3H). LC/MS found: [M+H]$^+$=523.33.

Example 6

N-((1R,2S,5R)-5-(isopropylamino)-2-((3S)-3-((1-oxido-6-(trifluoromethyl)-4-quinazolinyl)amino)-2-oxo-1-pyrrolidinyl)cyclohexyl)acetamide

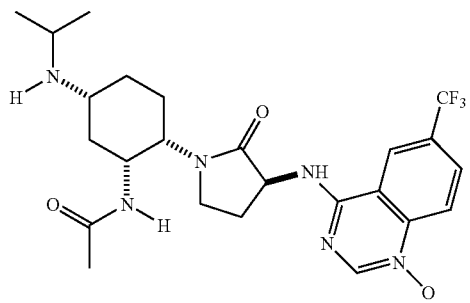

Example 6, Step 1: The title product is synthesized as part of the first listed synthesis of Example 5 (conducted in two steps). If desired, the title compound could be purified from this procedure rather than reacted further to form Example 5.

Alternative Preparation of Example 6

Example 6, Alternative Preparation, Step 1: To a solution of benzyl (S)-1-((1S,2R,4R)-2-acetamido-4-(isopropylamino) cyclohexyl)-2-oxopyrrolidin-3-ylcarbamate (0.090 g, 0.209 mmol; see Example 1, Step 8) in MeOH (10 mL) was added ~100 mg of 10% Pd/C (50%, wet). The mixture was stirred under H$_2$ (50 psi) for 14 h. The catalyst was filtered off and the solvent was evaporated to give N-((1R,2S,5R)-2-((S)-3- amino-2-oxopyrrolidin-1-yl)-5-(isopropylamino)cyclohexyl)acetamide as a foamy solid residue (50 mg, 0.169 mmol). This material was dissolved in i-PrOH (2 mL), and the resultant solution was charged with 4-phenoxy-6-(trifluoromethyl)quinazoline 1-oxide (103 mg, 0.169 mmol; see Example 5, Alternative Preparation, Step 2) and N,N-diisopropylethylamine (0.059 ml, 0.337 mmol). The vessel was sealed under argon atmosphere and heated in a microwave for 1 hr at 120° C. The reaction was evaporated to give an oily residue, which was purified by automated flash chromatography to give a yellow solid. This was re-crystallized from $CH_2Cl_2$-hexane to afford the desired 4-((S)-1-((1S,2R,4R)-2-acetamido-4-(isopropylamino)cyclohexyl)-2-oxopyrrolidin-3-ylamino)-6-(trifluoromethyl)quinazoline 1-oxide (1st crop, 43.5 mg and 2nd crop, 3.1 mg). LC/MS found: $(M+H)^+$=509.32. $^1$H-NMR (400 MHz, $CD_3OD$), δ ppm: 8.99 (s, 1H), 8.81 (s, 1H), 8.62 (d, J=9.0 Hz, 1H), 8.33 (dd, J=9.0, 1.6 Hz, 1H), 5.28 (t, J=8.3 Hz, 1H), 4.56 (brs, 1H), 4.02 (brd, 1H), 3.63 (m, 2H), 3.18 (brs, 1H), 2.55 (m, 1H), 2.27 (m, 1H), 2.03 (s, 3H), 1.97-1.67 (m, 7H), 1.16 (d, J=5.5 Hz, 3H), 1.15 (d, J=5.5 Hz, 3H).

Example 7

N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)formamide

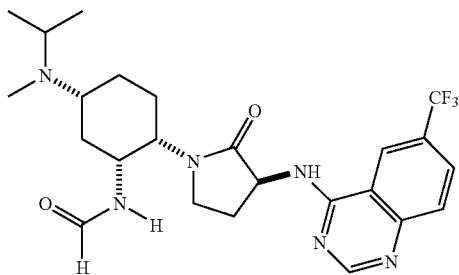

Example 7, Step 1: A stirring solution of (1R,2S,5R)-2-((S)-3-(benzyloxycarbonylamino)-2-oxopyrrolidin-1-yl)-5-(tert-butoxycarbonylamino)cyclohexanecarboxylic acid (38 g, 0.0799 mol; see Example 1, Step 4) in dichloromethane (400 mL) was charged with trifluoroacetic acid (100 mL) at 0° C. The reaction was stirred for 2 h at room temperature and concentrated in vacuo. The residue was dissolved in dichloromethane (100 ml) and the resultant solution was added dropwise to diethyl ether (1500 ml) with stirring. The solid formed was collected with filtration and washed with diethyl ether (3×50 ml). The white solid was dried in vacuo to give (1R,2S,5R)-5-amino-2-((S)-3-(benzyloxycarbonylamino)-2-oxopyrrolidin-1-yl)cyclohexanecarboxylic acid as its TFA salt (35.5 g, 86%). The compound was used to next step without further purification. LC/MS found $[M+H]^+$=376.

Example 7, Step 2: A stirring solution of (1R,2S,5R)-5-amino-2-((S)-3-(benzyloxycarbonylamino)-2-oxopyrrolidin-1-yl)cyclohexanecarboxylic acid (TFA salt, 35.5 g, 0.0725 mol) in dichloroethane (350 mL) was charged sequentially with N-methylmorpholine (29.3 g, 4.0 eq) and acetone (42.05 g, 10 eq). The mixture was stirred at room temperature for 10 min. and sodium triacetoxyborohydride (30.7 g, 2 eq) was added at 0° C. The mixture was stirred at room temperature for 14 h, then formaldehyde (37 wt % solution, 28.4 g, 5 eq) and sodium triacetoxyborohydride (18.4 g, 1.2 eq) were added. The mixture was stirred at room temperature for 2 h. Water (70 ml) was added and the stirring was continued for 10 minutes. The mixture was concentrated under reduced pressure to remove the organic solvents. The resulting mixture was adjusted pH to 7-8 with saturated $NaHCO_3$ solution and then to pH~6 with 1 N HCl. The mixture was extracted with dichloromethane (5×250 ml). The extracts were combined, dried over anhydrous $Na_2SO_4$, and concentrated under reduced pressure. The residue was dissolved in dichloromethane (100 ml) and the resultant solution was added dropwise to diethyl ether (1500 ml) with stirring. The solid formed was collected with filtration and washed with diethyl ether (3×50 ml). The white solid was dried in vacuo to give (1R,2S,5R)-2-((S)-3-(benzyloxycarbonylamino)-2-oxopyrrolidin-1-yl)-5-(isopropyl(methyl)amino)cyclohexanecarboxylic acid (31 g, 99%). The compound was used in the next step without further purification. LC/MS found $[M+H]^+$=432.

Example 7, Step 3: A stirring solution of (1R,2S,5R)-2-((S)-3-(benzyloxycarbonylamino)-2-oxopyrrolidin-1-yl)-5-(isopropyl(methyl)amino)cyclohexanecarboxylic acid (15.0 g, 0.0348 mol) in 1,4-dioxane (200 ml) was charged with N-methylmorpholine (5.26 g, 1.5 eq) and DPPA (14.3 g, 1.5 eq) at 0° C. The mixture was stirred at room temperature for 2 h. The mixture was charged with 2-(trimethylsilyl)ethanol (6.16 g, 1.5 eq) and then stirred for 2.5 h at 85° C. under the protection of nitrogen. The reaction was cooled to room temperature and the solvent was removed under reduced pressure. The resulting residue was dissolved in ethyl acetate (250 ml) and washed with saturated $NaHCO_3$ (3×80 ml) and brine (3×80 ml). The solution was dried over anhydrous $Na_2SO_4$, filtered, and concentrated in vacuo. The residue obtained was purified with silica gel column chromatography eluting with 1% and 2.5% of methanol in dichloromethane to give 2-(trimethylsilyl)ethyl (1R,2S,5R)-2-((S)-3-benzyloxycarbonylamino-2-oxopyrrolidin-1-yl)-5-(isopropyl(methyl)amino)cyclohexylcarbamate (9.3 g, 49%). LC/MS found $[M+H]^+$=547.

Example 7, Step 4: A stirring solution of 2-(trimethylsilyl)ethyl (1R,2S,5R)-2-((S)-3-benzyloxycarbonylamino-2-oxopyrrolidin-1-yl)-5-(isopropyl(methyl)amino)cyclohexylcarbamate (272 mg, 0.5 mmol) in dichloromethane (3 mL) was charged with trifluoroacetic acid (2 mL). The reaction was stirred for 2 h at room temperature and concentrated in vacuo. The residue was dissolved in dichloromethane (50 ml) and washed with saturated $NaHCO_3$ (15 ml). the aqueous layer was extracted with dichloromethane (4×30 ml). Combined all the dichloromethane layers and dried over anhydrous $Na_2SO_4$, filtered, and concentrated in vacuo to give benzyl (S)-1-((1S,2R,4R)-2-amino-4-(isopropyl(methyl)amino)cyclohexyl)-2-oxopyrrolidin-3-ylcarbamate (190 mg, 94.5%). LC/MS found $[M+H]^+$=403.

Example 7, Step 5: To 460 mg (10 mmol) of formic acid, acetic anhydride (204 mg, 2 mmol) was added. The mixture was stirred at room temperature for 2 h. Then one fifth of the above solution was added to a mixture of benzyl (S)-1-((1S,2R,4R)-2-amino-4-(isopropyl(methyl)amino)cyclohexyl)-2-oxopyrrolidin-3-ylcarbamate (60 mg, 0.149 mmol) in dichloromethane (3 ml) and triethylamine (62.3 µl, 3 eq) at 0° C. with stirring. The reaction was stirred for 1 h at room temperature and 1 ml of water was added to quench the reaction. The mixture was diluted with dichloromethane (60 ml) and washed with saturated $NaHCO_3$ (20 ml). The solution was dried over anhydrous $Na_2SO_4$, filtered, and concentrated in vacuo to give benzyl (S)-1-((1S,2R,4R)-2-formamido-4-(isopropyl(methyl)amino)cyclohexyl)-2-oxopyrrolidin-3-ylcarbamate (50 mg, 78%). LC/MS found $[M+H]^+$=431.

Example 7, Step 6: To a solution of benzyl (S)-1-((1S,2R,4R)-2-formamido-4-(isopropyl(methyl)amino)cyclohexyl)-2-oxopyrrolidin-3-ylcarbamate (50 mg, 0.116 mmol) in methanol (3 mL) was added 10% Pd/C (40 mg of 50% wet catalyst). The flask was evacuated and back-filled with hydrogen from a hydrogen balloon. The mixture was stirred at room temperature for 1 h and the catalyst was removed by filtration. The filtrate was concentrated in vacuo to provide N-((1R,2S,5R)-2-((S)-3-amino-2-oxopyrrolidin-1-yl)-5-(isopropyl(methyl)amino)cyclohexyl)formamide (35 mg, 100%) which was taken on to the next step without further purification. LC/MS found $[M+H]^+=297$.

Example 7, Step 7: To a solution of N-((1R,2S,5R)-2-((S)-3-amino-2-oxopyrrolidin-1-yl)-5-(isopropyl(methyl)amino)cyclohexyl)formamide (34 mg, 0.115 mmol) in isopropanol (3 mL) was added 4-chloro-6-(trifluoromethyl)quinazoline (32 mg, 1.2 eq, see: P. H. Carter et al., PCT application WO 2005/021500) and triethylamine (29.1 mg, 2.5 eq). The mixture was stirred at room temperature for overnight. The solvent was removed under reduced pressure. The residue was purified with preparative HPLC to provide the title compound as its TFA salt (76 mg, 91.7%). LC/MS found $[M+H]^+=493$. $^1$H-NMR (400 MHz, CD$_3$OD), δ ppm: 8.73-8.90 (2H, m), 8.26 (1H, d, J=8.65 Hz), 8.09 (1H, s), 7.96 (1H, d, J=9.16 Hz), 5.35 (1H, t, J=9.66 Hz), 4.30 (2H, s), 3.57-3.92 (4H, m), 2.77-2.83 (3H, m), 2.56-2.68 (1H, m), 1.91-2.46 (6H, m), 1.29-1.48 (6H, m).

Example 8

N-((1R,2S,5R)-5-(dimethylamino)-2-((3S)-2-oxo-3-((6-(trifluoromethyl)-4-quinazolinyl)amino)-1-pyrrolidinyl)cyclohexyl)acetamide

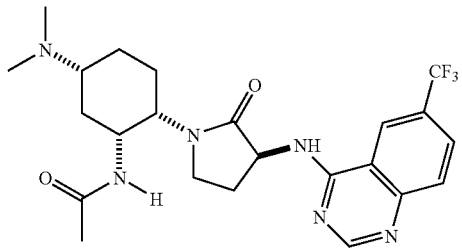

Example 8, Step 1: A stirring solution of tert-butyl (1R,3R,4S)-3-acetamido-4-((S)-3-(benzyloxycarbonylamino)-2-oxopyrrolidin-1-yl)cyclohexylcarbamate (66 g, 0.135 mol; see Example 1, Step 6) in dichloromethane (216 mL) was charged with trifluoroacetic acid (216 mL). The reaction was stirred for 2 h at room temperature and concentrated in vacuo. The residue was dissolved in methanol and the resultant solution was concentrated in vacuo; this was repeated once. Benzyl (S)-1-((1S,2R,4R)-2-acetamido-4-aminocyclohexyl)-2-oxopyrrolidin-3-ylcarbamate was obtained as an oil. LC/MS found $[M+H]^+=389.4$. $^1$H-NMR (400 MHz, d-MeOH): δ 7.3-7.4 (m, 5H), 5.12 (s, 2H), 4.41 (br. s, 1H), 4.15 (m, 1H), 4.00 (t, J=9.3 Hz, 1H), 3.81 (t, J=9.1 Hz, 1H), 3.65 (q, J=8.4 Hz, 1H), 3.3-3.4 (m, 1H), 2.45 (m, 1H), 1.95-2.24 (m, 5H), 2.00 (s, 3H), 1.6-1.8 (m, 2H).

Example 8, Step 2: To a solution of benzyl (S)-1-((1S,2R,4R)-2-acetamido-4-aminocyclohexyl)-2-oxopyrrolidin-3-ylcarbamate, TFA salt (500 mg, 0.99 mmol) in CH$_2$Cl$_2$ (20 mL) was added sequentially formaldehyde (5 mL, 37 wt % solution), triethylamine (0.35 mL, 2.4 mmol), and sodium triacetoxyborohydride (315 mg, 1.5 mmol). After 16 h, the solution was diluted with CH$_2$Cl$_2$ and washed with saturated NaHCO$_3$. The organic layer was collected and extracted with aq. HCl solution (5 mL 1N HCl and 20 mL water). The aqueous phase was collected and basified with aq. NaOH solution (~10 mL 1N NaOH and 20 mL water) and then extracted with dichloromethane (2×50 mL). The organic extracts were combined, dried (Na$_2$SO$_4$), filtered, and concentrated in vacuo to give benzyl (S)-1-((1S,2R,4R)-2-acetamido-4-(dimethylamino)cyclohexyl)-2-oxopyrrolidin-3-ylcarbamate as an oil (280 mg, 68% yield). LC/MS found $[M+H]^+=417$.

Example 8, Step 3: To a mixture of benzyl (S)-1-((1S,2R,4R)-2-acetamido-4-(dimethylamino)cyclohexyl)-2-oxopyrrolidin-3-ylcarbamate (70 mg) and 10% Pd/C (30 mg of 50% wet catalyst) was added EtOAc (50 mL) and then the flask was evacuated and back-filled with hydrogen. The mixture was stirred under 1 atm H$_2$ for 16 h and the catalyst was removed by filtration through Celite. The filtrate was concentrated in vacuo to give N-((1R,2S,5R)-2-((S)-3-amino-2-oxopyrrolidin-1-yl)-5-(dimethylamino)cyclohexyl)acetamide as a white solid (40 mg, 85% yield), which was taken on to the next step without further purification. LC/MS found $[M+H]^+=283$.

Example 8, Step 4: To a solution of N-((1R,2S,5R)-2-((S)-3-amino-2-oxopyrrolidin-1-yl)-5-(dimethylamino)cyclohexyl)acetamide (40 mg, 0.14 mmol) in isopropanol (6 mL) was added 4-chloro-6-(trifluoromethyl)quinazoline (39 mg, 0.17 mmol) and triethylamine (0.02 mL, 0.14 mmol). The mixture was stirred at RT for 16 h and concentrated in vacuo to a crude oil, which was purified by semi-preparative reverse phase HPLC (gradient elution, water/methanol/TFA) to give the title compound (70 mg, 71% yield). LC/MS found $[M+H]^+=479$. $^1$H-NMR (400 MHz, CD$_3$OD), δ ppm: 8.87 (s, 1H), 8.72 (s, 1H), 8.22 (m, 1H), 7.87 (m, 1H), 5.49 (m, 1H), 4.23 (m, 1H), 4.2 (m, 1H), 4.12 (m, 1H), 3.75 (m, 1H), 3.65 (m, 1H), 3.38 (m, 1H), 2.82 (s, 6H), 2.51 (m, 1H), 2.35 (m, 1H), 2.15 (m, 1H), 2.14-1.86 (m, 5H), 1.84 (s, 3H).

Example 9

N-((3S)-1-((1S,2R,4R)-2-acetamido-4-(isopropyl(methyl)amino)cyclohexyl)-2-oxo-3-pyrrolidinyl)-6-tert-butyl-2-pyridinecarboxamide

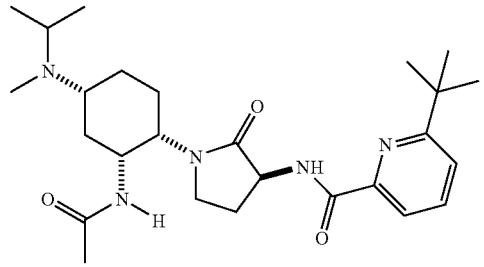

Example 9, Step 1: 6-tert-Butylpicolinonitrile (662 mg, 4.1 mmol; see: P. H. Carter et al., PCT application WO 2005/021500) was dissolved in glacial acetic acid (6.8 mL) prior to the addition of conc. HCl (1.6 mL). This mixture was heated in an oil bath (95° C.) overnight. After cooling, the solution was concentrated. The resulting crude solid was transferred in 50/50 Et$_2$O/hexane to a Buchner funnel. This solid was washed with additional 50/50 Et$_2$O/hexane to provide 6-tert-butylpicolinic acid, HCl salt (880 mg). LC/MS found $(M+H)^+=180.0$.

Example 9, Step 2: N-((1R,2S,5R)-2-((S)-3-amino-2-oxopyrrolidin-1-yl)-5-(isopropyl(methyl)amino)cyclohexyl)acetamide (70 mg, 0.22 mmol; see Example 1, Step 10) was dissolved in DMF (2 mL) prior to the addition of 4-methylmorpholine (0.1 mL, 0.91 mmol) and tert-butylpicolinic acid HCl salt (90 mg, 0.50 mmol). After cooling to 0° C., BOP (175 mg, 0.39 mmol) was added. The solution was warmed to room temperature and was stirred overnight. The solution was then filtered and was concentrated. The resulting residue was purified by reverse phase HPLC (gradient elution, water/methanol/TFA) to provide the title compound as its TFA salt (85.1 mg). LC/MS found [M+H]$^+$=487.45. $^1$H-NMR (400 MHz, CD$_3$OD), δ ppm: 7.9 (m, 2H), 7.67 (m, 1H), 4.47 (m, 1H), 4.38 (t, 1H), 4.24 (m, 1H), 3.97-3.74 (m, 3H), 3.64 (m, 1H), 2.82 (s, 3H), 2.6 (m, 1H), 2.34 (m, 2H), 2.25-2.05 (m, 2H), 2.01 (s, 3H), 1.95-1.8 (m, 2H), 1.45 (s, 9H), 1.37 (m, 3H).

Example 10

N-((1R,2S,5R)-5-amino-2-((3S)-2-oxo-3-((6-(trifluoromethyl)-4-quinazolinyl)amino)-1-pyrrolidinyl)cyclohexyl)propanamide

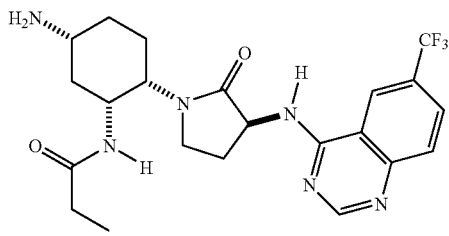

Example 10, Step 1: To the solution of (1R,2S,5R)-2-((S)-3-(benzyloxycarbonylamino)-2-oxopyrrolidin-1-yl)-5-(tert-butoxycarbonylamino)cyclohexanecarboxamide (2.0 g, 4.21 mmol; see Example 1, Step 5) in MeCN (150 mL) and H$_2$O (205 mL), iodobenzene diacetate (1.357 g, 4.21 mmol) was added. The mixture was stirred at 0° C. for 1 h and then allowed to warm to room temperature in the melting ice bath over 14 h. The mixture was acidified to pH 4 with the addition of acetic acid, and then extracted with diethyl ether (2×60 mL). The aqueous layer was concentrated under reduced pressure to remove acetonitrile. The residual solution was extracted with methylene chloride (2×80 mL) after adjusting the pH to 9-10 using saturated NaHCO$_3$. The methylene chloride layer was dried (Na$_2$SO$_4$) and concentrated in vacuo to give the desired tert-butyl (1R,3R,4S)-3-amino-4-((S)-3-benzyloxycarbonylamino-2-oxopyrrolidin-1-yl)cyclohexylcarbamate (1.8 g, 4.03 mmol, 96% yield). LC/MS found [M+H]$^+$=447.

Example 10, Step 2: To a solution of tert-butyl (1R,3R,4S)-3-amino-4-((S)-3-benzyloxycarbonylamino-2-oxopyrrolidin-1-yl)cyclohexylcarbamate (1.8 g, 4.03 mmol) in 3 mL of DMF was added propionic acid (0.285 g, 3.85 mmol), BOP (1.704 g, 3.85 mmol) and triethylamine (0.059 mL, 0.423 mmol). The mixture was stirred at room temperature for 1.5 h and then poured into water (75 mL). The resultant mixture was extracted with EtOAc (2×60 mL). The organic phases were combined and washed with sat. NaHCO$_3$ (2×40 mL) and brine (50 mL). The organic phase was then dried (MgSO$_4$), filtered, and concentrated in vacuo. The residue was dispersed in diethyl ether. The precipitated solid was collected by filtration, washed with diethyl ether (2×40 mL), and dried in vacuo to afford the tert-butyl (1R,3R,4S)-4-((S)-3-(benzyloxycarbonylamino)-3-propionamido-2-oxopyrrolidin-1-yl)cyclohexylcarbamate (1.6 g, 3.18 mmol, 79% yield). LC/MS found [M+H]$^+$=503.

Example 10, Step 3: To a solution of tert-butyl (1R,3R,4S)-4-((S)-3-(benzyloxycarbonylamino)-3-propionamido-2-oxopyrrolidin-1-yl)cyclohexylcarbamate (900 mg, 1.79 mmol) in 10 mL of MeOH was added palladium hydroxide on carbon, 20% (340 mg, 2.42 mmol). The mixture was evacuated and back filled with hydrogen from a hydrogen balloon. The mixture was stirred at room temperature for 1.5 h under 1 atm H$_2$. Filtration, followed by concentration under reduced pressure provided tert-butyl (1R,3R,4S)-4-((S)-3-amino-2-oxopyrrolidin-1-yl)-3-propionamidocyclohexylcarbamate (650 mg, 1.764 mmol, 99% yield), which was used in the next step without further purification. LC/MS found [M+H]$^+$=369.

Example 10, Step 4: To a solution of tert-butyl (1R,3R,4S)-4-((S)-3-amino-2-oxopyrrolidin-1-yl)-3-propionamidocyclohexylcarbamate (650 mg, 1.764 mmol) in 5 mL of isopropanol was added 4-chloro-6-(trifluoromethyl)quinazoline (492 mg, 2.117 mmol) and triethylamine (0.492 mL, 3.53 mmol). The mixture was stirred at 50° C. for 4 h. The solvent was removed under reduced pressure and the residue was diluted with 30 mL of 20% AcOH in water before being extracted with diethyl ether (2×20 mL). The ethereal layer was extracted with 20% AcOH solution in water (3×30 mL). The aqueous layers were combined and basified with Na$_2$CO$_3$ and extracted with methylene chloride (3×50 mL). The organic extracts were combined, washed with brine (40 mL), dried over anhydrous Na$_2$SO$_4$ and concentrated under reduced pressure to give tert-butyl (1R,3R,4S)-4-((S)-2-oxo-3-(6-(trifluoromethyl)quinazolin-4-ylamino)pyrrolidin-1-yl)-3-propionamidocyclohexylcarbamate, LC/MS found [M+H]$^+$=565. The entirety of this crude product was dissolved in 5 mL of methylene chloride. The resultant solution was charged with TFA (3 mL), stirred at room temperature for 30 min, and then concentrated in vacuo. The residue was purified with preparative reverse-phase HPLC to give the title compound as its TFA salt in aqueous methanol solution. This solution was concentrated in vacuo to remove the methanol and the residue solution was basified with saturated NaHCO$_3$ and extracted with methylene chloride (3×50 mL), dried (Na$_2$SO$_4$) and concentrated in vacuo to give the title compound as its free base (550 mg, 1.184 mmol, 67% yield). LC/MS found [M+H]$^+$=465. $^1$H-NMR (400 MHz, CD$_3$OD), δ ppm: 8.77 (1H, s), 8.57 (1H, s), 8.03 (1H, dd, J=9.16, 2.03 Hz), 7.88 (1H, d, J=8.65 Hz), 5.24 (1H, t, J=8.65 Hz), 4.55 (1H, d, J=3.56 Hz), 3.97-4.05 (1H, m), 3.52-3.67 (2H, m), 3.35-3.41 (1H, m), 2.47-2.58 (1H, m), 2.20-2.34 (3H, m), 1.62-2.04 (6H, m), 1.14 (3H, t, J=7.63 Hz).

Example 11

2-tert-butyl-N—((S)-1-((1S,2R,4R)-4-(tert-butylamino)-2-(methylsulfonamido)cyclohexyl)-2-oxopyrrolidin-3-yl)pyrimidine-4-carboxamide

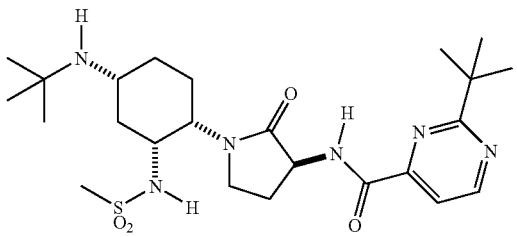

Example 11, Step 1: An oven-dried 3-neck round-bottom flask was equipped with a dried stir bar, a dried reflux condenser, and two septa. After cooling under N$_2$, the flask was charged sequentially with (1R,2S,5R)-2-((S)-3-(benzyloxycarbonylamino)-2-oxopyrrolidin-1-yl)-5-(tert-butoxycarbonylamino)cyclohexanecarboxylic acid (60 g, 126 mmol; see Example 1, Step 4), acetonitrile (800 mL), N-methylmorpholine (27.7 mL, 252 mmol), and diphenylphosphoryl azide (29.9 mL, 139 mmol). The reaction was stirred at RT for 1 h 40 min, at which time 2-trimethylsilylethanol (90 mL, 631 mmol) was added. The reaction was set to heat, and reached reflux 30 min later. It was allowed to reflux for 1 h, at which time it was allowed to cool to 50° C. gradually and then cooled to 15° C. with external cooling. The reaction was quenched with the addition of acetic acid (1.734 mL, 30.3 mmol). The reaction was concentrated in vacuo and then dissolved in EtOAc (1.2 L). It was washed sequentially with water (1×0.3 L), sat. NaHCO₃ (2×0.3 L), 1N HCl (1×0.3 L), and brine (2×0.3 L). The organic phase was dried (Na₂SO₄), filtered, and concentrated in vacuo. A solid appeared very early on in the concentration process. After the volatiles were removed, 800 mL 10% EtOAc/Hexanes was added, and the mixture was stirred overnight. The solid was collected and dried to yield tert-butyl (1R,3R,4S)-4-((S)-3-benzyloxycarbonylamino-2-oxopyrrolidin-1-yl)-3-((2-trimethylsilyl)ethoxycarbonylamino)cyclohexylcarbamate (60.5 g, 102 mmol, 81% yield). HPLC showed that the material was 72% pure, with two 12% impurities. This material was taken into the next step without purification. The filtrate was later concentrated to yield another 4.38 g of product. Total yield=64.9 g (87%).

Example 11, Step 2: A dry 500 mL round-bottom flask was equipped with a stir bar and charged sequentially with tert-butyl (1R,3R,4S)-4-((S)-3-benzyloxycarbonylamino-2-oxopyrrolidin-1-yl)-3-((2-trimethylsilyl)ethoxycarbonylamino)cyclohexylcarbamate (60.5 g), CH₂Cl₂ (180 mL), and a solution of para-toluenesulfonic acid monohydrate (19.48 g, 102 mmol) in CH₂Cl₂ (120 mL) and methanol (30 mL). The mixture was placed on a rotary evaporator and the bulk of the CH₂Cl₂ was removed (bath temp ca. 20° C.). When the mixture began to foam, the vacuum was released, and the bath temperature increased to 46° C. (the temperature varied between 44 and 51° C.; it was controlled with the addition of external ice). The mixture was rotated at this temperature for exactly one hour (gas evolution was visible throughout) and then diluted with EtOAc (1 L). The organic phase was washed with 0.5 N NH₄OH (2×250 mL). The aqueous washes were combined and set aside. The organic phase was washed with sat. NH₄Cl (1×250 mL) and sat. NaCl (1×250 mL); these aqueous washes were discarded. The initial combined NH₄OH washes were back-extracted with EtOAc (1×250 mL), and that organic extract was washed with sat. NH₄Cl (1×60 mL) and sat. NaCl (1×60 mL). All of the organic extracts were combined, dried (Na₂SO₄), filtered, and concentrated. The residue was purified by elution through a SiO₂ plug (13 cm wide×7.5 cm tall). The first eluant was pure EtOAc (ca. 4 L). The second eluant was 1:9 (10% NH₄OH in MeOH)/CH₂Cl₂ (ca. 5 L). The fractions containing the desired product were pooled together and evaporated to afford the desired 2-(trimethylsilyl)ethyl (1R,2S,5R)-5-amino-2-((S)-3-benzyloxycarbonylamino-2-oxopyrrolidin-1-yl)cyclohexylcarbamate (31.6 g, 64.4 mmol, 63% yield).

Example 11, Step 3: To a solution of 2-(trimethylsilyl)ethyl (1R,2S,5R)-5-amino-2-((S)-3-benzyloxycarbonylamino-2-oxopyrrolidin-1-yl)cyclohexylcarbamate (1.03 g, 2.099 mmol) in methanol (10 ml) was added 3,5-di-tert-butyl-1,2-benzoquinone (0.555 g, 2.52 mmol). This mixture was stirred for 2 hr before THF (6 mL) and water (2 mL) were added along with oxalic acid to pH 4. This mixture was concentrated. The resulting residue was dissolved in ethyl acetate and washed with brine. The organic layer was dried (MgSO₄), filtered, and concentrated. This was purified via flash chromatography to give 2-(trimethylsilyl)ethyl (1R,2S)-2-((S)-3-benzyloxycarbonylamino-2-oxopyrrolidin-1-yl)-5-oxocyclohexylcarbamate (0.550 g, 1.123 mmol, 53.5% yield). LC/MS found [M+H]⁺=491.3.

Example 11, Step 4: To a solution of 2-(trimethylsilyl)ethyl (1R,2S)-2-((S)-3-benzyloxycarbonylamino-2-oxopyrrolidin-1-yl)-5-oxocyclohexylcarbamate (0.550 g, 1.123 mmol) in methylene chloride (0.4 mL) was added t-butylamine (1.180 ml, 11.23 mmol) and Titanium(IV) isopropoxide (6.63 ml, 22.47 mmol). This mixture was stirred for 2 h before sodium cyanoborohydride (127 mg, 2.022 mmol) and MeOH (1 mL) were added. After 2 h, methylene chloride (50 mL) was added, followed by 1N NaOH. The mixture was filtered through Celite to remove the titanium salts. The filtrate was dried and concentrated in vacuo to give 2-(trimethylsilyl)ethyl (1R,2S,5R)-2-((S)-3-benzyloxycarbonylamino-2-oxopyrrolidin-1-yl)-5-(tert-butylamino)cyclohexylcarbamate and its 5S diastereomer as a mixture (510 mg, 0.933 mmol, 83% yield). LC/MS found [M+H]⁺=547.31.

Example 11, Step 5: The product from Step 4 (510 mg, 0.933 mmol) was dissolved in CH₂Cl₂ (2 ml) and trifluoroacetic acid (2.87 ml, 37.3 mmol). After 30 min, the solution was concentrated to give the bis-TFA salt of benzyl (S)-1-((1S,2R,4R)-2-amino-4-(tert-butylamino)cyclohexyl)-2-oxopyrrolidin-3-ylcarbamate as a mixture with its 4S diastereomer (520 mg, 0.825 mmol, 88% yield). LC/MS found [M+H]⁺=403.25.

Example 11, Step 6: A portion of the amine from Step 5 (362 mg, 0.57 mmol) was dissolved in methylene chloride (3 mL). The resultant solution was charged successively with triethylamine (0.125 ml, 0.900 mmol) and methanesulfonyl chloride (0.070 ml, 0.900 mmol). The mixture was stirred for 2 h at RT and washed with sat. NaHCO₃ solution, dried (Na₂SO₄), filtered and concentrated in vacuo. The residue was dissolved in methanol (3 ml). The vessel was charged with Pd/C (150 mg, 1.410 mmol) and fitted with a hydrogen balloon. After 1 h, the solution was filtered and concentrated in vacuo. The residue was re-dissolved in methanol (3 mL) and the vessel was again charged with Pd/C (150 mg, 1.410 mmol) and fitted with a hydrogen balloon. After 1 h, the solution was filtered and concentrated in vacuo to give N-((1R,2S,5R)-2-((S)-3-amino-2-oxopyrrolidin-1-yl)-5-(tert-butylamino)cyclohexyl)methanesulfonamide as a mixture with its 5S diastereomer (190 mg, 0.548 mmol, 75% yield). LC/MS found [M+H]⁺=347.3.

Example 11, Step 7: The product amine from Step 7 (190 mg, 0.548 mmol) was dissolved in methylene chloride (3 mL). The 2-tert-butylpyrimidine-4-carboxylic acid (196 mg, 1.09 mmol; see P. H. Carter et al., PCT application WO 2005/021500), EDC (210 mg, 1.097 mmol), and N-methylmorpholine (0.247 ml, 2.193 mmol) were added prior to the addition of HOBt (364 mg, 2.7 mmol). This mixture was stirred overnight. The solution was concentrated, filtered, and purified by preparative reverse-phase HPLC to give the TFA salt of the title compound in diastereomerically-pure form (123 mg, 0.198 mmol, 36%). LC/MS found [M+H]⁺=509.35. ¹H-NMR (400 MHz, CD₃OD), δ ppm: 9.36 (br d, 1H), 8.97 (d, 1H), 7.88 (d, 1H), 4.49 (m, 2H), 3.94-3.75 (m, 3H), 3.64 (m, 1H), 3.04 (s, 3H), 2.58 (m, 1H), 2.33 (m, 2H), 2.2-1.96 (m, 4H), 1.88 (m, 1H), 1.48 (s, 9H), 1.44 (s, 9H).

Example 12

2-tert-butyl-N-((3S)-1-((1S,2R,4R)-4-(tert-butylamino)-2-(propionylamino)cyclohexyl)-2-oxo-3-pyrrolidinyl)-4-pyrimidinecarboxamide

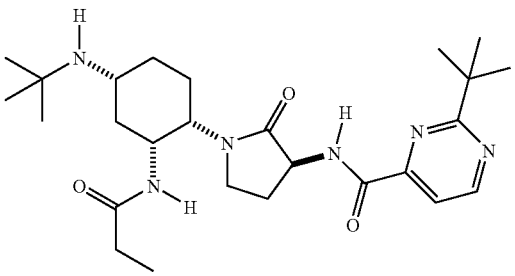

Example 12, Step 1: A sample of 2-(trimethylsilyl)ethyl (1R,2S,5R)-2-((S)-3-benzyloxycarbonylamino-2-oxopyrrolidin-1-yl)-5-(tert-butylamino)cyclohexylcarbamate and its 5S diastereomer (68 mg, 0.141 mmol; see Example 11, Step 4) was dissolved in MeOH (3 ml) prior to the addition of 10% Pd/C (100 mg, 0.940 mmol) and a hydrogen balloon. After 1 h, the solution was filtered and concentrated in vacuo. The reaction was then set-up again with fresh reagents. After 1 h, the solution was filtered and concentrated to give 2-(trimethylsilyl)ethyl (1R,2S,5R)-2-((S)-3-amino-2-oxopyrrolidin-1-yl)-5-(tert-butylamino)cyclohexylcarbamate as a mixture with its 5S diastereomer (139.4 mg, 0.338 mmol, 99% yield): LC/MS found [M+H]$^+$=413.4.

Example 12, Step 2: The product from Step 1 above (139.4 mg, 0.338 mmol) was dissolved in CH$_2$Cl$_2$ (3 mL). The solution was charged sequentially with 2-tert-butylpyrimidine-4-carboxylic acid (122 mg, 0.676 mmol), 1H-benzo[d][1,2,3]triazol-1-ol (91 mg, 0.676 mmol), and 4-methylmorpholine (0.149 ml, 1.351 mmol). The solution was then charged with 1-(3-dimethylamino)propyl)-3-ethyl-carbodiimide hydrochloride (130 mg, 0.676 mmol). This mixture was stirred overnight. The solution was concentrated, filtered, and purified by preparative reverse-phase HPLC (Phenomenex 21×250 mm, 0% to 100% methanol-water containing 0.1% trifluoroacetic acid over 30 min, 15 mL/min, 220 nM, product RT=29.9 min) to give the TFA salt of 2-(trimethylsilyl)ethyl (1R,2S,5R)-5-(tert-butylamino)-2-((S)-3-(2-tert-butylpyrimidine-4-carboxamido)-2-oxopyrrolidin-1-yl)cyclohexylcarbamate (92 mg, 0.134 mmol, 39.5% yield). LC/MS found [M+H]$^+$=575.5.

Example 12, Step 3: The product of Step 2 (92 mg, 0.134 mmol) was dissolved in CH$_2$Cl$_2$ (2 ml) prior to the addition of trifluoroacetic acid (3.09 ml, 40.1 mmol). After 30 min, the solution was concentrated to give the TFA salt of N—((S)-1-((1S,2R,4R)-2-amino-4-(tert-butylamino)cyclohexyl)-2-oxopyrrolidin-3-yl)-2-tert-butylpyrimidine-4-carboxamide (87 mg, 0.132 mmol, 99% yield). LC/MS found [M+H]$^+$=431.37.

Example 12, Step 4: The TFA salt of N—((S)-1-((1S,2R,4R)-2-amino-4-(tert-butylamino)cyclohexyl)-2-oxopyrrolidin-3-yl)-2-tert-butylpyrimidine-4-carboxamide (87 mg, 0.132 mmol) was dissolved in CH$_2$Cl$_2$ (3 ml) prior to the addition of triethylamine (0.092 ml, 0.660 mmol). The solution was cooled to 0° C. and charged with propionic anhydride (0.051 ml, 0.396 mmol). After 30 min, the solution was concentrated, filtered, and purified by preparative reverse-phase HPLC (Phenomenex 21×100 mm, 0% to 100% methanol-water containing 0.1% trifluoroacetic acid over 10 min, 20 mL/min, 220 nM, product RT=8.2 min) to give the title compound as its TFA salt. This material was dissolved in methylene chloride. The resultant solution was washed with sat Na$_2$CO$_3$ and then dried and concentrated in vacuo to give the title compound (46 mg, 0.095 mmol, 72% yield). LC/MS found [M+H]$^+$=487.45. $^1$H-NMR (400 MHz, CD$_3$OD), δ ppm: 8.84 (d, 1H), 7.73 (d, 1H), 4.57 (t, 1H), 4.29 (m, 1H), 3.95 (m, 1H), 3.51 (m, 2H), 2.97 (m, 1H), 2.42 (m, 1H), 2.12 (q, 2H), 2.06 (m, 1H), 1.9 (m, 1H), 1.75-1.55 (m, 5H), 1.36 (s, 9H), 1.36-1.02 (m, 12H).

Example 13

N-((1R,2S,5R)-5-(tert-butylamino)-2-((3S)-3-((6-tert-butylpyrimido[5,4-d]pyrimidin-4-yl)amino)-2-oxo-1-pyrrolidinyl)cyclohexyl)methanesulfonamide

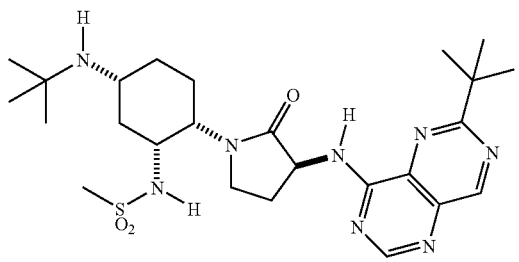

Example 13, Step 1: A sample of 2-(trimethylsilyl)ethyl (1R,2S,5R)-2-((S)-3-benzyloxycarbonylamino-2-oxopyrrolidin-1-yl)-5-(tert-butylamino)cyclohexylcarbamate and its 5S diastereomer (100 mg, 0.183 mmol; see Example 11, Step 4) was dissolved in dichloromethane (2 ml) prior to the addition of trifluoroacetic acid (2.54 ml, 32.9 mmol). After 30 min, the solution was concentrated in vacuo. The residue was dissolved in dichloromethane (3 ml) prior to the addition of triethylamine (0.100 ml, 0.720 mmol) and methanesulfonyl chloride (0.018 ml, 0.234 mmol). After 2 h, this was washed with sat NaHCO$_3$ solution and the organic layer was dried (Na$_2$SO$_4$), filtered and concentrated to afford benzyl (S)-1-((1S,2R,4R)-4-(tert-butylamino)-2-(methylsulfonamido)cyclohexyl)-2-oxopyrrolidin-3-ylcarbamate as a mixture with its 4S diastereomer (66 mg, 0.137 mmol, 76% yield). LC/MS found [M+H]$^+$=481.22.

Example 13, Step 2: The product from Step 1 above (0.066 g, 0.137 mmol) was dissolved in MeOH (4 ml) prior to the addition of 10% Pd/C (150 mg, 1.410 mmol) and a hydrogen balloon. After 1 h, the solution was filtered and concentrated in vacuo. The reaction was then set-up again with fresh reagents. After 1 h, the solution was filtered and concentrated to give N-((1R,2S,5R)-2-((S)-3-amino-2-oxopyrrolidin-1-yl)-5-(tert-butylamino)cyclohexyl)methanesulfonamide as a mixture with its 5S diastereomer (47.5 mg, 0.137 mmol, 100% yield). LC/MS found [M+H]$^+$=347.3.

Example 13, Step 3: The product from Step 2 (47.5 mg, 0.137 mmol) was dissolved in 2-Propanol (2 ml). The resultant solution was charged sequentially with triethylamine (0.057 ml, 0.411 mmol) and 2-tert-butyl-8-chloropyrimido[5,4-d]pyrimidine (45.8 mg, 0.206 mmol; see P. H. Carter et al., PCT application WO 2005/021500). After stirring for 2 h, the solution was concentrated. The residue was purified by preparative reverse-phase HPLC (Phenomenex Luna 5u C18 21.2×100 mm, % methanol-water containing 0.1% trifluoroacetic acid, gradient over 12 min, 20 mL/min, 220 nM, product retention time=8.2 min) to give the product as a TFA salt. This was dissolved in dichloromethane and washed with 20% Na$_2$CO$_3$ solution. The organic layer was concentrated to give the title compound (18 mg, 0.034 mmol, 24.66% yield). LC/MS found [M+H]$^+$=533.3. $^1$H-NMR (400 MHz, CD$_3$OD), δ ppm: 9.15 (s, 1H), 8.47 (s, 1H), 5.16 (m, 1H), 3.91 (m, 2H), 3.83 (m, 1H), 3.55 (m, 1H), 3.14 (m, 1H), 2.91 (s, 3H), 2.53 (m, 1H), 2.1 (m, 2H), 1.9 (m, 1H), 1.77-1.55 (m, 4H), 1.40 (s, 9H), 1.07 (s, 9H).

Example 14

N-((1R,2S,5R)-5-(tert-butylamino)-2-((3S)-3-((1-oxido-6-(trifluoromethyl)-4-quinazolinyl)amino)-2-oxo-1-pyrrolidinyl)cyclohexyl)acetamide

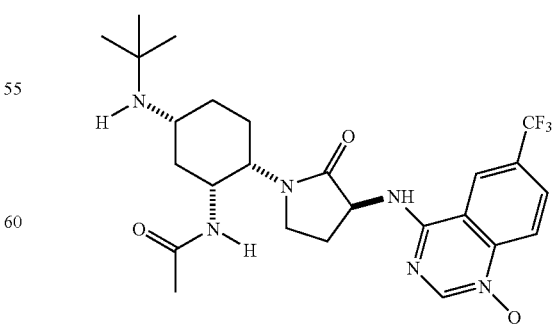

Example 14, Step 1: To a solution of tert-butyl (1R,3R,4S)-3-acetamido-4-((S)-3-(benzyloxycarbonylamino)-2-oxopyrrolidin-1-yl)cyclohexylcarbamate (100 g, 0.205 mol; see Example 1, Step 6) in dichloromethane (400 ml) was added TFA (400 ml) at −20° C. The reaction solution was stirred at room temperature for 2 h. The solvent and most of TFA were removed under reduced pressure, and the residue was diluted with dichloromethane (2 L) and aqueous $K_2CO_3$ solution (2 L). The pH was adjusted to 10 with 1N HCl. The aqueous layer was extracted with dichloromethane (3×1 L). The combined organic layer was dried over $Na_2SO_4$, and concentrated to give benzyl (S)-1-((1S,2R,4R)-2-acetamido-4-aminocyclohexyl)-2-oxopyrrolidin-3-ylcarbamate as an oil (81 g, 100% yield). This amine was used directly in the next step without further purification.

Example 14, Step 2: A solution of benzyl (S)-1-((1S,2R,4R)-2-acetamido-4-aminocyclohexyl)-2-oxopyrrolidin-3-ylcarbamate (13.3 g, 34 mmol) and 3,5-di-tert-butylcyclohexa-3,5-diene-1,2-dione (7.54 g, 34 mmol) in methanol (160 ml) was stirred at room temperature for 2 h. The solution was concentrated and diluted with acetone (132 ml) and water (33 ml), followed by addition of Dowex-50WX8-200 (33 g). The reaction was stirred at room temperature for 2 h. Dowex-50WX8-200 was removed by filtration and washed with dichloromethane (300 ml). The filtrate was concentrated under vacuum to remove most of acetone. The residue was diluted with dichloromethane (200 ml) and washed with aqueous $NaHCO_3$ solution (200 ml) and brine (200 ml). The combined aqueous layers were extracted with dichloromethane (2×100 ml). The combined organic extracts were dried over $Na_2SO_4$ and concentrated. The product benzyl (S)-1-((1S,2R)-2-acetamido-4-oxocyclohexyl)-2-oxopyrrolidin-3-ylcarbamate was obtained as a solid (12 g, 90% yield) by crystallization in EtOAc (100 ml) and Hexane (200 ml). $^1$H-NMR (500 MHz, DMSO-$d_6$) δ ppm 7.99 (d, J=9.35 Hz, 1H), 7.44 (d, J=8.80 Hz, 1H), 7.28-7.39 (m, 5H), 5.03 (s, 2H), 4.50 (s, 1H), 4.31 (d, J=12.10 Hz, 1H), 4.18 (q, J=8.98 Hz, 1H), 3.27 (m, 2H), 2.82 (dd, J=15.12, 5.22 Hz, 1H), 2.52-2.65 (m, 1H), 2.40 (dd, J=12.92, 4.67 Hz, 1H), 2.15-2.31 (m, 2H), 2.09 (d, J=15.40 Hz, 1H), 1.90 (m, 1H), 1.81 (s, 3H), 1.68 (m, 1H). m/z: 388.46 [M+H].

Example 14, Step 3: To a solution of $TiCl_4$ (1M in dichloromethane, 36 ml, 36 mmol) in dichloromethane (30 ml) at 0° C. was added $Ti(OiPr)_4$ (10.8 ml, 36 mmol). The mixture was then stirred at room temperature for 10 min. To a solution of benzyl (S)-1-((1S,2R)-2-acetamido-4-oxocyclohexyl)-2-oxopyrrolidin-3-ylcarbamate (23.25 g, 60 mmol) in dichloromethane (600 ml) was added tert-butylamine (30 ml, 300 mmol) at room temperature, followed by the addition of the $TiCl_4/Ti(OiPr)_4$ solution at −50° C. The reaction was allowed to warm slowly to room temperature. The reaction was finished after 2 h (The reaction was monitored on HPLC by quenching an HPLC sample with $NaBH_4$ in methanol). The solution was cooled to 10° C. and $BH_3.SMe_2$ (1M in dichloromethane, 66 ml, 66 mmol) was added. The mixture was stirred at room temperature for 5 h then quenched with $Na_2CO_3$ aqueous solution (300 ml). The precipitate was filtered off. The two layers were separated and the aqueous layer was extracted with dichloromethane (600 ml). The combined dichloromethane layers were extracted with 1N HCl twice (150 ml and 15 ml). (The product and the undesired trans isomer were both in the acidic aqueous phase.) The combined acidic aqueous layers were neutralized with 12 M aqueous solution of $NH_4OH$ (12 ml) to pH~8 and extracted with dichloromethane twice (600 ml, 450 ml). (The product was in organic phase, while the trans isomer was still in aqueous layer.) The combined organic layers were washed with $NH_4Cl$ aqueous solution 3 times (3×200 ml) until there was no trans isomer left in organic layer. The organic layer was dried over $Na_2SO_4$ and concentrated. The residue was purified by crystallization in EtOAc/Hexane (200 ml/800 ml) to give the desired benzyl (S)-1-((1S,2R,4R)-2-acetamido-4-(tert-butylamino)cyclohexyl)-2-oxopyrrolidin-3-ylcarbamate (20.80 g, 78% yield) as a white solid with 99.5% purity. $^1$H-NMR (500 MHz, DMSO-$d_6$) δ ppm 8.76 (s, 1H), 7.27-7.46 (m, 6H), 5.03 (m, 2H), 4.14 (m, 1H), 4.07 (q, J=8.80 Hz, 1H), 3.83 (m, 1H), 3.36 (m, 2H), 2.91 (s, 1H), 2.18 (m, 1H), 2.04 (m, 1H), 1.78 (s, 3H), 1.41-1.74 (m, 7H), 1.04 (s, 9H). m/z: 445.54 [M+H].

Example 14, Step 4: To a solution of benzyl (S)-1-((1S,2R,4R)-2-acetamido-4-(tert-butylamino)cyclohexyl)-2-oxopyrrolidin-3-ylcarbamate (43.3 g, 98 mmol) in methanol (400 ml), 10% wet Pd/C (4.34 g) was added. The mixture was evacuated and back-filled with hydrogen with a hydrogen balloon. The mixture was stirred at room temperature for 5 h. The mixture was filtered and washed with methanol (500 ml) and concentrated under vacuum to dryness. The crude product obtained was distilled with IPA (2×100 ml) under reduced pressure to give product N-((1R,2S,5R)-2-((S)-3-amino-2-oxopyrrolidin-1-yl)-5-(tert-butylamino)cyclohexyl)acetamide as an oil (30 g, 98% yield). This amine was used in the next step without further purification.

Example 14, Step 5: To a solution of N-((1R,2S,5R)-2-((S)-3-amino-2-oxopyrrolidin-1-yl)-5-(tert-butylamino)cyclohexyl)acetamide (50 mg, 0.161 mmol, prepared as described above) and 4-phenoxy-6-(trifluoromethyl)quinazoline 1-oxide (99 mg, 0.161 mmol; see Example 5, Alternative Preparation, Step 2) in i-PrOH (2 ml) was added N,N-diisopropylethylamine (0.056 ml, 0.322 mmol). The vessel was sealed under argon atmosphere and heated in a microwave for 1 hr at 120° C. LC/MS found: (M+H)$^+$=523.3 as the major product peak. The reaction was repeated on the same scale in a separate vessel. The two reactions were combined and evaporated to give an oily residue, which was purified by automated flash chromatography (40 g silica gel) with elution by 8:92 (10% $cNH_4OH$ in MeOH). The fractions containing the desired product were pooled and concentrated in vacuo. The residue was crystallized from $CH_2Cl_2$ and hexane. The two crops were combined and dried under vacuum to afford 4-((S)-1-((1S,2R,4R)-2-acetamido-4-(tert-butylamino)cyclohexyl)-2-oxopyrrolidin-3-ylamino)-6-(trifluoromethyl)quinazoline 1-oxide (101 mg). Analysis by $^1$H-NMR showed that this material contained ~0.6 molar equivalents of $CH_2Cl_2$. LC/MS found: [M+H]$^+$=523.30. $^1$H-NMR (400 MHz, $CD_3OD$), δ ppm: 9.00 (s, 1H), 8.80 (s, 1H), 8.61 (d, J=9.0 Hz, 1H), 8.32 (dd, J=9.0, 1.6 Hz, 1H), 5.28 (t, J=8.3 Hz, 1H), 4.57 (brs, 1H), 4.02 (brd, 1H), 3.65-3.51 (m, 2H), 3.24 (brs, 1H), 2.59-2.51 (m, 1H), 2.34-2.20 (m, 1H), 2.04 (s, 3H), 2.04 (m, 1H), 1.89 (brs, 3H), 1.74 (brs, 2H), 1.20 (s, 9H).

Example 15

N-(((1S,2S,5R)-5-methoxy-2-((3S)-2-oxo-3-((6-(trifluoromethyl)-4-quinazolinyl)amino)-1-pyrrolidinyl)cyclohexyl)methyl)acetamide

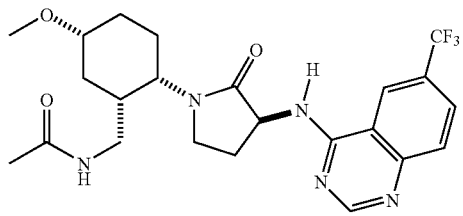

Example 15, Step 1: A sample of benzyl (1R,2S,5R)-7-oxo-6-oxabicyclo[3.2.1]octan-2-ylcarbamate (9 g, 32.7 mmol; see P. H. Carter et al., PCT application WO 2005/021500) was dissolved in THF (50 ml) and water (16.67 ml) at room temperature prior to the addition of sodium borohydride (1.237 g, 32.7 mmol). The reaction mixture was stirred for 22 h. It was quenched with saturated NaHCO$_3$ solution. The reaction mixture was extracted with a 1:9 MeOH—CH$_2$Cl$_2$ mixture (5×). The combined organic layer was then washed with brine and dried over anhydrous MgSO$_4$. The desired product, benzyl (1S,2R,4R)-4-hydroxy-2-(hydroxymethyl)cyclohexyl carbamate (8.75 g, 31.3 mmol, 96% yield) was obtained as a white foamy solid. LC/MS found [M+H]$^+$=280.30.

Example 15, Step 2: A sample of benzyl (1S,2R,4R)-4-hydroxy-2-(hydroxymethyl)cyclohexylcarbamate (20.5 g, 73.4 mmol) was dissolved in anhydrous pyridine (140 mL) at room temperature prior to the addition of trityl chloride (20.46 g, 73.4 mmol) in one portion. The reaction mixture was stirred for two days. Pyridine was evaporated and the residue was dissolved in EtOAc. The solution was washed with water (2×) followed by brine. The combined aqueous layer was re-extracted with EtOAc. This organic layer was washed with brine. The combined organic layer was then dried over anhydrous Na$_2$SO$_4$ and evaporated to get an oily residue which yielded white crystalline product from EtOAc and hexane. The mother liquor was chromatographed (400 g silica gel eluted with 20% EtOAc/hexane followed by 40% and finally 70%). The desired regioisomer, benzyl (1S,2R,4R)-4-hydroxy-2-(trityloxymethyl)cyclohexylcarbamate (33.08 g, 63.4 mmol, 86% yield) was obtained as a white solid. MS found [M–H]$^-$=520.2 (AP/CI). $^1$H-NMR (400 MHz, CDCl$_3$) δ, ppm 7.4 (d, J=7.12 Hz, 6H), 7.19-7.34 (m, 15H), 5.25-5.31 (m, 1H), 4.98-5.09 (m, 2H), 3.92 (s, 1H), 3.66 (bs, 1H), 3.14-3.24 (m, 1H), 2.97 (dd, J=9.41, 4.83 Hz, 1H), 1.98-2.08 (m, 1H), 1.91 (d, J=11.9 Hz, 2H), 1.76-1.84 (m, 1H), 1.36-1.49 (m, 2H), 1.39-1.43 (m, 1H), 1.19-1.30 (m, 1H). A small amount of the undesired isomer, benzyl (1S,2R,4R)-2-(hydroxymethyl)-4-(trityloxy)cyclohexyl carbamate (1.17 g, 2.243 mmol, 3.06% yield) was also obtained. MS found [M–H]$^-$=520.2 (AP/CI). $^1$H-NMR (400 MHz, CDCl$_3$) δ, ppm 7.48 (d, J=7.12 Hz, 6H), 7.32-7.40 (m, 5H), 7.21-7.32 (m, 10H), 5.05-5.14 (m, 2H), 4.96 (d, J=8.65 Hz, 1H), 3.89 (dd, J=8.39, 2.8 Hz, 1H), 3.84 (dd, J=10.7, 4.58 Hz, 1H), 3.46 (ddd, J=14.5, 9.92, 4.07 Hz, 1H), 3.07 (ddd, J=15.26, 10.43, 4.3 Hz, 1H), 1.66 (dd, J=14.24, 3.05 Hz), 1.43-1.51 (m, 1H), 1.30-1.40 (m, 2H), 1.14-1.23 (m, 1H), 0.79-0.91 (m, 1H), 0.72-0.79 (m, 1H).

Example 15, Step 3: A sample of benzyl (1S,2R,4R)-4-hydroxy-2-(trityloxymethyl)cyclohexylcarbamate (11.5 g, 21.47 mmol) was dissolved in CH$_2$Cl$_2$ (100 mL) at room temperature under N$_2$ prior to the addition of, in sequence, 1,8-bis(dimethylamino)naphthalene (11.50 g, 53.7 mmol), molecular sieves (powdered 4A, 5 g) and trimethyloxonium tetrafluoroborate (6.35 g, 42.9 mmol, in three portions). Reaction mixture was stirred for 48 h. Starting material still remained. Additional amounts of trimethyloxonium tetrafluoroborate (1.5 g) and molecular sieves (1 g) were added and the reaction mixture stirred for another 5 h. It was diluted with 200 ml of CH$_2$Cl$_2$ and filtered through Celite. The filterate was washed with 0.5N HCl (3× with 50 ml) followed by saturated Na$_2$CO$_3$ and dried over anhydrous MgSO$_4$. Then the solution was evaporated and dried in vacuo to yield a pale yellow foam. The yellow foam was taken in 100 ml of AcOH:water (7:3) and stirred at 60° C. for 3 h. The resulting pink solution was concentrated and made basic with 1N NaOH. The mixture was extracted with EtOAc (5×, 150 ml each). The combined organic layer was washed with brine, dried over anhydrous MgSO$_4$, concentrated and chromatographed (300 g silica gel; eluted with 7:3 EtOAc:hexane, followed by EtOAc). The desired benzyl(1S,2R,4R)-2-(hydroxymethyl)-4-methoxycyclohexyl carbamate (6.1 g, 20.79 mmol, 97%) was obtained as an oil. LC/MS found [M+H]$^+$=294.41.

Example 15, Step 4: A sample of triphenylphosphine (7.39 g, 28.2 mmol) was dissolved in THF (60 mL) at 0° C. prior to the dropwise addition of the diethylazodicarboxylate (4.46 mL, 28.2 mmol). Stirring was continued for 30 min at 0° C., when a solution of the benzyl(1S,2R,4R)-2-(hydroxymethyl)-4-methoxycyclohexyl carbamate (4.13 g, 14.08 mmol) in THF (40 mL) was added to the reaction mixture slowly. The reaction mixture was stirred at 0° C. for 30 min when a solution of hydrogen azide (14.08 ml, 28.2 mmol) (as a 2M solution in benzene) was added slowly. The reaction mixture was stirred at 0° C. for 90 min. It was quenched with MeOH and stirred overnight at room temperature. The reddish yellow solution was concentrated and chromatographed. The benzyl (1S,2S,4R)-2-(azidomethyl)-4-methoxycyclohexylcarbamate (4.19 g, 13.16 mmol, 93% yield) was obtained as a very viscous oil. LC/MS found [M+H]$^+$=319.5.

Example 15, Step 5: A sample of benzyl (1S,2S,4R)-2-(azidomethyl)-4-methoxycyclohexylcarbamate (4.7 g, 14.76 mmol) was dissolved in THF at room temperature prior to the addition of water (0.293 ml, 16.24 mmol) and triphenylphosphine (4.26 g, 16.24 mmol). The reaction was stirred at 60° C. for 4 h. It was then cooled and treated with a saturated aqueous solution of Na$_2$CO$_3$ (3.13 g, 29.5 mmol) followed by di-t-butyldicarbonate (3.77 ml, 16.24 mmol). The reaction mixture was stirred overnight at room temperature. It was partitioned between EtOAc and water. The organic layer was washed with brine and dried over anhydrous MgSO$_4$. The solution was concentrated and chromatographed (500 ml silica gel eluted with 30% EtOAc/hexane). The desired tert-butyl ((1S,2S,5R)-2-benzyloxycarbonylamino-5-methoxycyclohexyl)methylcarbamate was obtained as a viscous oil. LC/MS found [M–Boc+H]$^+$=293.25.

Example 15, Step 6: A sample of the product from Step 5 was dissolved in MeOH (100 ml). Palladium on carbon (0.185 g, 1.743 mmol) was added to the solution and the reaction mixture was stirred under 50 psi hydrogen for 2 h. The reaction mixture was filtered through Celite with EtOAc. The resulting solution was concentrated in vacuo to yield tert-butyl ((1S,2S,5R)-2-amino-5-methoxycyclohexyl)methylcarbamate as a clear oil which was used without any further purification. A quantitative yield was assumed. LC/MS found [M+H]$^+$=259.41.

Example 15, Step 7: A sample of tert-butyl ((1S,2S,5R)-2-amino-5-methoxycyclohexyl)methylcarbamate (2.53 g, 9.79 mmol) was dissolved in CH$_2$Cl$_2$ (50 ml) at room temperature. The solution was charged sequentially with 1-hydroxybenzotriazole (1.456 g, 10.77 mmol), N-carbobenzyloxy-L-methionine (4.16 g, 14.69 mmol) and 1-(3-dimethylaminopropyl)-3-ethylcarbodiimide hydrochloride (2.440 g, 12.73 mmol). The reaction mixture was stirred overnight. It was diluted with EtOAc and washed with saturated Na$_2$CO$_3$, followed by brine. The solution was dried (MgSO$_4$), filtered, and concentrated in vacuo to yield tert-butyl ((1S,2S,5R)-2-((S)-2-benzyloxycarbonylamino-4-(methylthio)butanamido)-5-methoxycyclohexyl)methylcarbamate as a colorless sticky solid. LC/MS found [M+H]$^+$=524.31.

Example 15, Step 8: A sample of the product from Step 7 was dissolved in iodomethane (30 ml) and stirred at room temperature for two days. The reaction mixture was evaporated and dried in vacuo. The residue was dissolved in CH$_2$Cl$_2$ and evaporated. The process was repeated four more times. The resulting residue was dried in vacuo to yield a yellow foamy solid which was then taken in DMF (20 ml) and treated with $Cs_2CO_3$ (6.36 g, 19.52 mmol). The reaction mixture was stirred at room temperature overnight. It was diluted with EtOAc and washed with water (2×). The combined aqueous layer was extracted with EtOAc (2×). The combined organic layer was then washed with brine and dried over anhydrous $MgSO_4$. The solution was then concentrated and chromatographed to yield tert-butyl ((1S,2S,5R)-2-((S)-3-benzyloxycarbonylamino-2-oxopyrrolidin-1-yl)-5-methoxycyclohexyl)methylcarbamate as a white foamy solid. LC/MS found $[M+H]^+=476.4$ Example 15, Step 9: A sample of tert-butyl ((1S,2S,5R)-2-((S)-3-benzyloxycarbonylamino-2-oxopyrrolidin-1-yl)-5-methoxycyclohexyl)methylcarbamate (0.75 g, 1.577 mmol) was dissolved in $CH_2Cl_2$ (15 mL) at room temperature. The solution was charged with trifluoroacetic acid (1.215 mL, 15.77 mmol) and stirred for 6 h. It was then evaporated and dried in vacuo. The residue was dissolved in EtOAc and washed with saturated $Na_2CO_3$, followed by brine. The organic layer was then dried over anhydrous $Na_2SO_4$, concentrated and dried in vacuo to yield a pale yellow foam. This material was dissolved in $CH_2Cl_2$ (10 mL) at room temperature. The solution was charged sequentially with triethylamine (0.659 mL, 4.73 mmol), dimethylaminopyridine (0.019 g, 0.158 mmol), and acetic anhydride (0.164 mL, 1.734 mmol). The reaction mixture was stirred for 90 min and then quenched with saturated $NaHCO_3$. The reaction mixture was then extracted with $CH_2Cl_2$ (3×). The organic layers were combined, dried over anhydrous $MgSO_4$, concentrated and chromatographed. The desired product, benzyl (S)-1-((1S,2S,4R)-2-(acetamidomethyl)-4-methoxycyclohexyl)-2-oxopyrrolidin-3-ylcarbamate, was obtained as a white solid. LC/MS found $[M+H]^+=418.4$.

Example 15, Step 10: A sample of the benzyl (S)-1-((1S,2S,4R)-2-(acetamidomethyl)-4-methoxycyclohexyl)-2-oxopyrrolidin-3-ylcarbamate (614 mg, 1.471 mmol) and Pd/C (62.6 mg, 0.294 mmol) were stirred in MeOH (30 mL) at room temperature under 50 psi hydrogen atmosphere for 2 h. The suspension was filtered through Celite with EtOAc, concentrated and dried in vacuo to yield N-(((1S,2S,5R)-2-((S)-3-amino-2-oxopyrrolidin-1-yl)-5-methoxycyclohexyl)methyl)acetamide (410 mg, 1.447 mmol, 98% yield) as a white solid. LC/MS found $[M+H]^+=284.24$.

Example 15, Step 11: A sample of the N-(((1S,2S,5R)-2-((S)-3-amino-2-oxopyrrolidin-1-yl)-5-methoxycyclohexyl)methyl)acetamide (220 mg, 0.776 mmol) was dissolved in 2-propanol (10 ml) at room temperature. To this solution was added triethylamine (0.433 ml, 3.11 mmol), followed by 4-chloro-6-(trifluoromethyl)quinazoline (235 mg, 1.009 mmol). The reaction mixture was stirred overnight. It was concentrated and chromatographed (120 g silica gel eluting with 5% followed by 10% MeOH in $CH_2Cl_2$) to afford the title compound (300 mg, 0.626 mmol, 81% yield) as a white solid. LC/MS found $[M+H]^+=480.4$. $^1$H-NMR (400 MHz, $CDCl_3$), δ ppm: 8.6 (s, 1H), 8.51 (s, 1H), 7.92 (br s, 1H), 7.87-7.82 (m, 2H), 6.28 (br s, 1H), 5.00 (dd, J=16.02, 8.65 Hz, 1H), 4.36-4.35 (m, 1H), 3.72-3.68 (m, 1H), 3.63-3.56 (m, 1H), 3.37-3.23 (m, 2H), 3.31 (s, 3H), 3.18-3.13 (m, 1H), 2.69-2.66 (m, 1H), 2.12-2.07 (m, 1H), 2.06-1.89 (m, 4H), 1.96 (s, 3H), 1.74-1.67 (m, 1H), 1.57-1.51 (m, 1H), 1.30-1.28 (m, 1H).

Comparative Pharmacological Characteristics

Assays and data comparing the pharmacological characteristics of compounds of the present invention and compounds found in WO2005021500 (corresponding to U.S. Pat. No. 7,163,937, assigned to present applicant) are presented below.

Human Peripheral Blood Mononuclear Cell Binding ("CCR2 Binding")

See also: Yoshimura et al., *J. Immunol.* 1990, 145, 292. The human CCR2 binding assay was established with human peripheral blood mononuclear cells (hPBMCs) using $^{125}$I-human MCP-1 as the tracer ligand. hPBMCs were isolated from human leukopak (Biological Specialty Inc.) using a standard protocol with Ficoll-Hypaque (Mediatech Cellgro). Isolated hPBMCs were washed and diluted to $1 \times 10^7$/ml in binding buffer (RPMI-1640, 0.1% BSA, 20 mM Hepes, pH 7.4). $^{125}$I-MCP-1 (NEN/Perk Elmer) was diluted to 0.45 nM in binding buffer. The compound was diluted in binding buffer at 3-fold the final concentrations used in the binding assay. The binding assay was performed using a 96-well filter plate (Millipore). Total $^{125}$I-MCP-1 binding was assessed as follows: to each reaction of a total volume of 150 μl were added $5 \times 10^5$ cells, 0.15 nM [25]-MCP-1, and compound such that the final concentration ranged from 0 to 100 nM. The plate was incubated at room temperature for 30 minutes followed by three washes with RPMI-1640, 0.1% BSA, 0.4 M NaCl, 20 mM Hepes, pH 7.4 using a vacuum manifold filtration (Millipore). After washing, the plate was air-dried for 60 minutes at room temperature. This was followed by adding 25 μl of Microscint 20 into each well. The plate was sealed and counted on the Trilux for 1 minute. Non-specific binding was determined in the presence of 300 nM cold MCP-1 (Pepro-Tech Inc.). Specific 1-MCP-1 was calculated as the difference between total and non-specific binding. All conditions were tested in duplicate. The IC50 is defined as the concentration of competing compound required to reduce specific binding by 50%.

hERG Flux

HEK293 cells stably-expressing hERG channels were grown (37° C., 5% $CO_2$) in Dulbecco's Modified Eagle's Media supplemented with 10% Sigma fetal bovine serum, non-essential amino acids, 2 mM L-glutamine and 500 μg/ml G418, at incubator. Cell dissociation buffer was used to extract the cells from flasks, which were then plated into 384-well Corning poly-D-lysine coated black/clear plates at a density of $2 \times 10^4$ cells per well (20 μl) in 10% serum media, and incubated for 15-24 hours at 37° C. in a 5% $CO_2$ incubator until a confluent monolayer of cells was obtained.

A 2 mM stock of BTC-AM dye (Molecular Probes, Eugene, Oreg.) was prepared in 100% DMSO and then added 1:1 to 10% (w/v) pluronic acid in DMSO on the day of assay. The dye was then diluted in hERG external EP buffer (140 mM NaCl, 4.0 mM KCl, 1.8 mM $CaCl_2$, 1.0 mM $MgCl_2$, 10 mM HEPES, pH 7.3 and 10 mM glucose; all buffer components obtained from Sigma Chemical). This BTC dye mixture (3011) was added to the cells and produced a final loading concentration of 2.5 μM. Cells are incubated at 21° C. for 45 minutes.

Test compounds were diluted to 10 mM DMSO in 6011. These compounds were then serially-diluted at a 1:2 ratio in DMSO in columns 1-10 and 11-20 of a 384-well plate. Assay-ready plates were generated by stamping 2.5 μl from the DMSO serially diluted plate, which was prepared on the Velocity 11 BioCel. Aqueous plates were created by adding 48 μl of EP buffer and then were diluted 30-45 minutes before the assay was read on the FLIPR. After dye loading, aqueous-diluted compounds were added to the cells of the three replicate plates (10 µl) yielding a ten point concentration range of 80 µM to 0.156 nM. Final DMSO concentration in the assay is 1%. Assay-ready aqueous plates were prepared and diluted on a Cybio liquid handler.

Cells loaded with dye were read on the FLIPR384 (Molecular Devices, Sunnyvale, Calif.), which excites the dye using the 488 nm line of an argon laser. Emission was filtered using a 540±30 nm bandpass filter. hERG channels are stimulated to open by the addition of 20 1l/well EP buffer containing 66 mM $K_2SO_4$ and 1.3 mM $Tl_2SO_4$ (Sigma/Aldrich). For each plate, data were collected every second for a period of 12 seconds, at which time the $Tl^+$-containing stimulus buffer was added. Data collection proceeded every second for 48 seconds, and then continued every three seconds for an additional 2 minutes.

The dynamic range of the assay was determined from blanks and totals wells. The totals wells (columns 21 and 22) define maximal hERG activation for the plate (no test compound present), and the blanks wells (columns 23 and 24) define 100% hERG inhibition. The blanks wells contain 400 nM of either of the standard hERG inhibitors dofetilide (Ficker et al., 1998) or E-4031. Raw data points in each sample well were first corrected for cell/signal variation, negative control (blanks) background, and normalized to the positive controls (totals) using the online FLIPR software. Test compound concentration response curves for the hERG $Tl^+$ flux data were then fit using Excel Fit (ID Business Solutions Limited, Surrey, UK) with a single-site logistic equation, $Y=A+((B-A)/1+((C/X)^\wedge D)))$ where A=maximal inhibition. Data were analyzed by fitting maximum amplitudes of change in fluorescence for $Tl^+$ flux for a given condition of test compound. Potencies ($IC_{50}$ values) of compounds were calculated from the average of triplicate wells.

Sodium Channel, Site 2 Binding Assay

See also: W. A. Catterall, et al. *J. Biol. Chem.* 1981, 256, 8922. The standard binding buffer contained 50 mM HEPES, 50 mM Tris-HCl, pH 7.4, 130 mM Choline Chloride, 5.4 mM KCl, 0.8 mM $MgCl_2$, 5.5 mM glucose, 40 µg/mL LqT. Binding reactions were initiated by adding synaptosomes (prepared from Wistar rat brain) to the reaction mixture containing 5 nM [$^3$H]-Batrachotoxin in a standard binding buffer and the compound to be tested at the desirable concentration. Samples were then mixed and incubated at 37° C. for 60 minutes. The reactions were stopped by adding ice-cold washing buffer containing 50 mM HEPES, 50 mM Tris-HCl, pH 7.4, 1.8 mM $CaCl_2$, 0.8 mM $MgCl_2$ and 1 mg/mL bovine serum albumin. The synaptosomes were immediately collected onto glass fiber filters and washed 3 times with washing buffers. The radioactivity of [$^3$H]-Batrachotoxin remaining on the filters was counted using liquid scintillation spectrometers.

Parallel Artificial Membrane Permeability Assay (PAMPA)

The Parallel Artificial Membrane Permeability Assay (PAMPA) consists of a specially formulated lecithin-based lipid combination referred to as the gastrointestinal tract (GIT) lipid. The GIT lipid is used to form a membrane in a sandwich plate assembly similar to that used in the Caco-2 assays. The GIT lipid closely resembles in vivo membrane composition and performance as measured by standard compounds that are known to be passively absorbed in humans. PAMPA is widely used as an in vitro model for permeability screening of discovery compounds. The rate of passage of compounds through the PAMPA membrane is used to determine a permeability coefficient (Pc), which can be related to the in vivo passive permeability of the compound.

The permeability coefficient (Pc) of a particular compound is examined in a pH-dependent setting with apical and basolateral pH of 7.4. All experiments are conducted in triplicate determinations.

Compounds (10 mM stocks in 100% DMSO) were diluted 1:100 in pH 7.4 donor well buffer (pION CAT # 110151), providing a 100 µM assay solution in 1% DMSO. Compound diluted in donor well buffer was transferred to a Whatman Unifilter plate and filtered prior to dispensing 200 µl into the donor well of the assay plate (pION CAT #110163). The PAMPA membrane was formed by pipetting 4 µl of the lipid solution (pION CAT #110169) onto the filter plate (VWR CAT #13503). The membrane was then covered with 200 µl of acceptor well buffer at pH 7.4 (pION CAT #110139). The PAMPA assay plate (donor side and acceptor side) was combined and allowed to incubate at room temperature for 4 hours. The plate was then disassembled and spectrophotometer plates (VWR CAT #655801) were filled (150 µl/well). The donor, acceptor, reference, and blank plates were read in the SpectraMax UV plate reader. Data was captured by the pION software, which analyzes the spectra and generates Pc values.

CCR2 Chemotaxis

The human CCR2 chemotaxis assay was conducted with the human monocytic cell line, THP-1. THP-1 cells were first labeled with the fluorescent dye Calcein-AM in phenol red-free, BSA-free RPMI-1640 (pH 7.4) at 37° C. for 30 minutes with gentle mixing every 15 minutes. The labeled cells were then washed and re-suspended at $1\times10^5$/ml in chemotaxis buffer (phenol red-free RPMI-1640, 0.1% BSA, pH 7.4). The test compound was diluted in chemotaxis buffer such that the final assay concentration ranged from 0.01 nM to 1 µM. The ligand MCP-1 (PeproTech Inc.) was diluted to 20 nM in chemotaxis buffer. To perform the assay, an equal volume of test compound dilutions was mixed with an equal volume of labeled THP-1 cells (Mixture 1), and an equal volume of test compound dilutions was mixed with an equal volume of diluted MCP-1 ligand (Mixture 2). Both mixtures were incubated independently at 37° C. for 10 minutes followed by gentle mixing. MCP-1-induced chemotaxis was then measured in a chemotaxis plate (Becton Dickinson) by placing 50 µl of Mixture 1 in the top chamber and 225 µl of Mixture 2 in the bottom chamber. The plate was covered with a lid and incubated at 37° C. for 30 minutes. 30 minutes later, the plate was read on a Cytofluor. All conditions were tested in duplicate. For signal to noise determination, 50 µl of labeled THP-1 cells alone ($5\times10^4$/well) were placed into the top chamber and 225 µl of ligand MCP-1 alone was placed in the bottom chamber (final concentration of 10 nM). The inhibition achieved by graded concentrations of test compound was calculated as a percentage of the compound-free MCP-1 control. The IC50 is defined as the concentration of test compound required to reach 50% inhibition of cellular chemotaxis.

hERG Patch Clamp

Whole-cell patch-clamp was used to directly measure hERG currents in HEK-293 cells stably expressing the cloned hERG potassium channel α subunit. The compound was tested in an aqueous buffer with pH 7.4 at room temperature.

Repetitive test pulses (0.05 Hz) were applied from a holding potential of −80 mV to +20 mV for 2 seconds and tail currents were elicited following the test pulses by stepping the voltage to −65 mV. The effects from the compound were calculated by measuring inhibition of peak tail current Sodium Channel Patch Clamp Whole-cell patch-clamp was used to directly measure inward sodium currents in HEK-293 cells expressing the human cardiac sodium channel, SCN5A. The compound was tested at a protein-free aqueous buffer. For determining steady state inhibition, sodium currents were elicited every 5 seconds using the following voltage protocol: cells were held at a potential of −90 mV and stepped to −20 mV for 60 ms. Effects were calculated by measuring inhibition of peak current during the test pulse to −20 mV. Rate-dependence of inhibition was assessed by stimulation at frequencies of 1 Hz and 4 Hz.

Single-dose Pharmacokinetics in Rats

Male Sprague-Dawley rats (250-300 g) were used for the pharmacokinetic studies. Rats were fasted overnight prior to PO dosing and fed 4 h post dose. Blood samples (~0.3 mL) were collected from the jugular vein into $K_2$EDTA-containing tubes and then centrifuged at 4° C. (1500-2000×g) to obtain plasma. In an oral bioavailability study, 2 groups of animals (N=2-3 per group) received the test compound either as an intravenous (IV) infusion (over 10 min) via the jugular vein or by oral gavage. Serial blood samples were obtained at 0.17 (for IV only), 0.25, 0.5, 0.75, 1, 2, 4, 6, 8, and 24 h post dose. Plasma samples, obtained by centrifugation at 4° C. (1500-2000×g), were stored at −20° C. until analysis by LC/MS/MS.

Single-dose Pharmacokinetics in Monkeys

The pharmacokinetics of various test compounds were evaluated in male Cynomolgus monkeys in a crossover-design. Monkeys were fasted overnight prior to PO dosing and fed 4 h post dose. A group of 1-3 animals (3 to 5 kg) received the compound by IV infusion (over 10 min) via a femoral vein and by oral gavage, with a 1-week washout between treatments. Serial blood samples (~0.3 mL) were collected from a femoral artery at 0.17 (IV only), 0.25, 0.5, 0.75, 1, 2, 4, 6, 8, and 24 h post dose, and centrifuged at 4° C. (1500-2000×g) to obtain plasma. Samples were stored at −20° C. until analysis by LC/MS/MS.

Data Analysis for Pharmacokinetic Assays

The pharmacokinetic parameters were obtained by non-compartmental analysis of plasma concentration vs. time data (KINETICA™ software, Version 4.2, InnaPhase Corporation, Philadelphia, Pa.). The peak concentration (Cmax) and time for Cmax were recorded directly from experimental observations. The area under the curve from time zero to the last sampling time (AUC(0-T)) was calculated using a combination of linear and log trapezoidal summations. The total plasma clearance (CLTp), steady-state volume of distribution (Vss), apparent elimination half-life (T1/2) and mean residence time (MRT) were estimated after IV administration. Estimations of T1/2 was made using a minimum of 3 time points with quantifiable concentrations. The absolute oral bioavailability (F) was estimated as the ratio of dose-normalized AUC values following oral and IV doses.

THP-1 Binding

The human CCR2 binding assay was also established with the THP-1 human monocytic leukemic cell line, which expresses endogenous CCR2, using 125I-human MCP-1 as the tracer ligand. Radioligand competition binding assays were used for assessment of binding affinity of test compounds to the CCR2 receptor. For radioligand competition studies, 100 µl containing $2.5 \times 10^5$ THP-1 cells/well (in assay buffer containing 50 mM HEPES, pH7.4, 5 mM $MgCl_2$, 1 mM $CaCl_2$ and 0.5% BSA) were added to 96-well assay plates containing test compound in 3-fold serial dilution, with final concentrations ranging from 5 µM to 100 µM. Subsequently, 50 µl $^{125}$I-MCP-1 radioligand at a final concentration of 0.2 nM in assay buffer were added to the reaction. After a 90 minute incubation period at room temperature, the binding reaction was terminated by harvesting on GF/B filter plates (PerkinElmer Cat. No. 6005177) followed by washing with ice-cold wash buffer (50 mM HEPES, pH 7.4, 0.1% BSA, 0.5 M NaCl) to remove unbound ligand. After washing, the plate was dried for 45 minutes at 60° C. followed by addition of 40 µl MicroScint 20 scintillation fluid, sealed and analyzed by the Packard TopCount reader. Non-specific binding was determined in the presence of 10 µM (a molar excess of 5000 fold) of an in-house CCR2 small molecule antagonist (Example 2k, WO2005021500; CCR2 IC50=2 nM). Specific binding of 1-MCP-1 was calculated as the difference between total and non-specific binding. The competition data was plotted as a percentage inhibition of radioligand specific bound in the absence of test compound (percent of total signal). After correcting for non-specific binding, IC50 values were determined. The IC50 is defined as the concentration of test compound required to reduce $^{125}$I-MCP-1 specific binding by 50% and was calculated using the four parameter logistic equation to fit the normalized data.

Find below data for each compound as measured in the assays described above.

TABLE 1

| | Comparative in vitro data. | | | |
|---|---|---|---|---|
| Compound | CCR2 Binding $IC_{50}$ (nM) | hERG FLUX $IC_{50}$ (nM) | $Na^+$ channel binding (% inhibition) | PAMPA permeability (nm/sec) |
| Example 12as, WO2005021500 | 0.27 (1) | 2.8 | Not available | Not available |

TABLE 1-continued

Comparative in vitro data.

| Compound | CCR2 Binding IC$_{50}$ (nM) | hERG FLUX IC$_{50}$ (nM) | Na$^+$ channel binding (% inhibition) | PAMPA permeability (nm/sec) |
| --- | --- | --- | --- | --- |
| Example 12aj, WO2005021500 | 0.43 ± 0.06 (2) | 0.77 | Not available | Not available |
| Example 2k, WO2005021500 | 0.88 ± 0.60 (23) | 51,000 | 97%, 10,000 nM | 529 ± 157 (9) |
| Example 12bd, WO2005021500 | 1.15 ± 0.07 (2) | >80,000 | 54%, 10,000 nM | 392 |
| Example 8a, WO2005021500 | 1.83 ± 0.80 (12) | >80,000 | 3%, 10,000 nM<br>33%, 30,000 nM | 94 ± 58 (10) |
| Example 8e, WO2005021500 | 2.20 ± 0.03 (2) | >80,000 | −6%, 10,000 nM | 2 ± 2 (2) |
| Example 9c, WO2005021500 | 0.96 ± 0.26 (19) | >80,000 | 48%, 10,000 nM<br>75%, 30,000 nM | 145 ± 71 (8) |
| Example 1, Present invention | 3.34 ± 0.32 (3) | >80,000 | 13%, 10,000 nM<br>6%, 30,000 nM | 187 |
| Example 3, Present invention | 4.74 ± 0.58 (3) | >80,000 | 17%, 10,000 nM<br>42%, 30,000 nM | 235 ± 68 (5) |
| Example 7, Present invention | 1.72 ± 0.54 (7) | >80,000 | 22%, 10,000 nM<br>44%, 30,000 nM | 326 ± 221 (2) |
| Example 8, Present invention | 3.58 ± 0.78 (3) | >80,000 | −14%, 10,000 nM<br>19%, 30,000 nM | 557 |
| Example 9, Present invention | 1.69 ± 0.67 (3) | >80,000 | 13%, 10,000 nM<br>48%, 30,000 nM | 266 |
| Example 10, Present invention | 5.18 ± 1.98 (6) | >80,000 | 18%, 10,000 nM<br>45%, 30,000 nM | 228 |
| Example 11, Present invention | 1.91 ± 0.52 (3) | >80,000 | 14%, 10,000 nM<br>34%, 30,000 nM | 350 |
| Example 12, Present invention | 4.49 ± 1.35 (3) | >80,000 | 18%, 10,000 nM<br>36%, 30,000 nM | 239 |
| Example 13, Present invention | 4.02 ± 1.31 (3) | >80,000 | 5%, 10,000 nM<br>21%, 30,000 nM | 541 ± 63 (2) |
| Example 15, Present invention | 3.34 ± 0.71 (4) | >80,000 | −5%, 10,000 nM<br>5%, 30,000 nM | 186 |

TABLE 2a

Additional comparative in vitro data.

| Compound | CCR2 Chemotaxis IC$_{50}$ (nM) | hERG patch clamp (% inhibition) | Na$^+$ channel patch clamp (% inhibition) |
| --- | --- | --- | --- |
| Example 2k, WO2005021500 | 0.24 ± 0.16 (12) | 83%, 10,000 nM | 52%, 10,000 nM<br>90%, 30,000 nM |
| Example 8a, WO2005021500 | 2.63 ± 1.24 (4) | 4%, 10,000 nM | 22%, 10,000 nM<br>49%, 30,000 nM |
| Example 9c, WO2005021500 | 0.21 | 4%, 10,000 nM | 19%, 10,000 nM<br>39%, 30,000 nM |
| Example 1, Present invention | 3.85 ± 0.36 (2) | 8%, 10,000 nM<br>17%, 30,000 nM | 13%, 30,000 nM |
| Example 3, Present invention | 2.20 ± 1.59 (5) | 6%, 10,000 nM<br>24%, 30,000 nM | 3%, 30,000 nM |
| Example 7, Present invention | 2.85 | 12%, 10,000 nM<br>29%, 30,000 nM | 10%, 30,000 nM |
| Example 8, Present invention | 4.09 ± 1.21 (4) | 18%, 10,000 nM<br>37%, 30,000 nM | 11%, 30,000 nM |
| Example 9, Present invention | 0.35 | 26%, 10,000 nM<br>41%, 30,000 nM | 6%, 30,000 nM |
| Example 10, Present invention | 1.6 ± 0.42 (4) | 33%, 30,000 nM | 35%, 30,000 nM |
| Example 11, Present invention | 0.92 | 15%, 30,000 nM | Not available |
| Example 12, Present invention | 0.88 | 6%, 10,000 nM<br>7%, 30,000 nM | Not available |
| Example 13, Present invention | 0.49 | 10%, 30,000 nM | Not available |
| Example 15, Present invention | 0.92 ± 0.67 (6) | 29%, 30,000 nM<br>47%, 100,000 nM | Not available |

TABLE 2B

Comparative In Vivo Pharmacokinetic Data in the Rat

| Compound | Dose IV/PO (mg/kg) | Cl (mL/min/kg) | F % | Oral AUC (nM * h) |
|---|---|---|---|---|
| Example 2k WO2005021500 | 2.5/25 | 40 | 68 | 9294 |
| Example 8a WO2005021500 | 6/72 | 42 | 1.4 | 690 |
| Example 9c, WO2005021500 | 4/43 | 54 | 14 | 1855 |
| Example 1, Present invention | Not available | Not available | Not available | Not available |
| Example 3, Present invention | 2/10 | 31 | 88 | 10068 |
| Example 7, Present invention | Not available | Not available | Not available | Not available |
| Example 8, Present invention | 8.6 (PO) | Not available | Not available | 7281 |
| Example 9, Present invention | Not available | Not available | Not available | Not available |
| Example 10, Present invention | 1.6/9.3 | 45 | 57 | 4227 |
| Example 11, Present invention | 2/10 | 56 | 52 | 3043 |
| Example 12, Present invention | 2/10 | 59 | 91 | 5228 |
| Example 13, Present invention | 2/10 | 26 | 88 | 10522 |
| Example 15, Present invention | 2.7/11 | 23 | 93 | 16221 |

TABLE 2C

Comparative In Vivo Pharmacokinetic Data in the Monkey

| Compound | Dose IV/PO (mg/kg) | Cl (mL/min/kg) | F % | Oral AUC (nM * h) |
|---|---|---|---|---|
| Example 2k WO2005021500 | 1/1.4 | 25 | 46 | 862 |
| Example 8a WO2005021500 | 1/11 | 14 | 9.4 | 1896 |
| Example 9c, WO2005021500 | 1/10 | 12 | 26 | 6763 |
| Example 1, Present invention | Not available | Not available | Not available | Not available |
| Example 3, Present invention | 1/1 | 15 | 91 | 2051 |
| Example 7, Present invention | Not available | Not available | Not available | Not available |
| Example 8, Present invention | 0.8 (PO) | Not available | Not available | 558 |
| Example 9, Present invention | Not available | Not available | Not available | Not available |
| Example 10, Present invention | 1/1 | 21 | 67 | 1085 |
| Example 11, Present invention | Not available | Not available | Not available | Not available |
| Example 12, Present invention | 1 (PO) | Not available | Not available | 413 |
| Example 13, Present invention | 1.7 (PO) | Not available | Not available | 263 |
| Example 15, Present invention | 0.9/1.5 | 28 | 19 | 333 |
| Example 6, Present invention | Not available | | | 139.1 (1) |
| Example 14, Present invention | 14.9 ± 5.2 (2) | | | 19.9 (1) |

| Compound | PBMC Binding IC$_{50}$ (nM) | THP-1 Binding IC$_{50}$ (nM) |
|---|---|---|
| Example 2, Present invention | 15.0 ± 7.3 (6) | 27 (1) |
| Example 4, Present invention | 3.46 ± 1.10 (5) | 4.22 ± 1.22 (4) |
| Example 5, Present invention | 27.5 ± 1.4 (2) | 21.3 (1) |

Utility

Representative compounds of the examples are shown to be modulators of chemokine receptor activity using assays know by those skilled in the art. In this section, we describe such assays and give their literature reference. More assays are described herein in the section titled "Comparative Pharmacological Characteristics", supra. By displaying activity in these assays of MCP-1 antagonism, compounds of the examples are expected to be useful in the treatment of human diseases associated with chemokines and their cognate receptors. The definition of activity in these assays is a compound demonstrating an IC$_{50}$ of 30 μM or lower in concentration when measured in a particular assay.

Antagonism of MCP-1 Binding to Human PBMC (Yoshimura et al., *J. Immunol.* 1990, 145, 292)

At least one of the compounds described in the examples have activity in the antagonism of MCP-1 binding to human PBMC (human peripheral blood mononuclear cells) described here.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration compound, is combined with 50 μl of $^{125}$-I labeled human MCP-1 (to give a final concentration of 150 μM radioligand) and 50 μl of binding buffer containing 5×10$^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-induced Calcium Influx (Sullivan et al., *Methods Mol. Biol.* 1999, 114, 125-133)

At least one compounds described in the examples have activity in the antagonism of MCP-1-induced calcium influx assay described here.

Calcium mobilization is measured using the fluorescent Ca$^{2+}$ indicator dye, Fluo-3. Cells are incubated at 8×10$^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes isolated as described by Weiner et al., *J. Immunol. Methods* 1990, 36, 89-97 or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2\text{-}4\times10^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-induced Human PBMC Chemotaxis (Bacon et al., *Brit. J. Pharmacol.* 1988, 95, 966)

At least one compounds described in the examples have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1\times10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell Derivation and Cell Culture

A pool of HT1080 cells stably expressing endogenous CC chemokine receptor 5 (CCR5) were developed using the methods outlined by Harrington, Sherf, and Rundlett (see U.S. Pat. No. 6,361,972 and U.S. Pat. No. 6,410,266). The highest-expressing clones were isolated using repetitive flow cytometry, followed by sub-cloning. These cells were then cultured in 6-well dishes at $3\times10^5$ cells/well and transfected with a DNA vector containing the chimeric HA-tagged G protein Gqi5 (Molecular Devices; 5 micrograms of linearized vector DNA in 15 microL of Ex-Gen from Fermentes was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation

A cell pellet containing $1 \times 10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding Assay

The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of $[^{125}I]$-MIP-1 beta (Perkin Elmer; material was diluted in Binding buffer such that the addition of 50 microliters/well gives a final concentration of 0.1 nM [125I]-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-based Functional Assay

HT1080 cells (clone 3559.1.6) were plated at 10,000 cells/well (30 microliters) in 384-well plates (black/clear bottom Biocoat PDL, Beckton Dickinson) and charged with 30 microliters/well of Fluoro-4 AM fluorescent dye (prepared by dissolving 1 mg Fluoro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e. agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

At least one compound of the disclosure is an inhibitor of both CCR2 and CCR5 and may be used to treat diseases associated with either chemokine. These compounds of the present invention are considered dual antagonists.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylos-*

*toma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Compounds disclosed herein are useful to treat or prevent disorders selected from rheumatoid arthritis, osteoarthritis, septic shock, atherosclerosis, aneurism, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus, esophageal squamous cell carcinoma, neuropathic pain, and obesity.

In another aspect, the compounds are useful to treat or prevent inflammatory disorders selected from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

In another aspect, examples disclosed herein may be useful in for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

In another aspect, disclosed herein are methods of treating cancer, wherein the cancer is selected from breast cancer, liver cancer, prostate cancer, and melanoma. Additionally, compounds disclosed herein may be useful in the treatment of ovarian cancer, and multiple myeloma.

The present invention provides methods for the treatment of a variety of non-cancerous proliferative diseases.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds disclosed herein may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound is used contemporaneously with one or more other drugs, a pharmaceutical composition containing such other drugs in addition to the compound of the present invention may be used. Accordingly, the pharmaceutical compositions include those that also contain one or more other active ingredients, in addition to a compound of the present disclosure.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, compounds disclosed herein (or other formulae disclosed herein) may be administered in combination with other anti-cancer and cytotoxic agents and treatments useful in the treatment of cancer or other proliferative diseases. The invention herein further comprises use of the compounds herein (or other formulae disclosed herein), in preparing medicaments for the treatment of cancer, and/or it comprises the packaging of the compounds of herein together with instructions that the compounds be used in combination with other anti-cancer or cytotoxic agents and treatments for the treatment of cancer. The present invention further comprises combinations of the compounds of and one or more additional agents in kit form, e.g., where they are packaged together or placed in separate packages to be sold together as a kit, or where they are packaged to be formulated together.

The second (or more) anti-cancer agents may be selected from any one or more of the following:

alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors;

cell-cycle response modifiers; enzymes; farnesyl-protein transferase inhibitors;

hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors;

microtubule-disruptor agents, such as ecteinascidins or their analogs and derivatives; microtubule-stabilizing agents such as taxanes, and the naturally-occurring epothilones and their synthetic and semi-synthetic analogs;

microtubule-binding, destabilizing agents (including vinca alkaloids); and topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

The compounds are administered to a mammal in a therapeutically effective amount. By "therapeutically effective amount" it is meant an amount of a compound of the present disclosure that, when administered alone or in combination with an additional therapeutic agent to a mammal, is effective to prevent or ameliorate the disease condition or the progression of the disease.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington s Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

"Substantially pure" as used herein is intended to include a compound having a purity greater than about 90 weight percent, including about 90, 91, 92, 93, 94, 95, 96, 97, 98, 99, and 100 percent.

As one example, a compound disclosed herein may be substantially pure in having a purity greater than about 90 percent (by weight), where the remaining less than about 10 percent of material comprises other metabolite of the compound, a prodrug of the compound, and/or reaction and/or processing impurities arising from its preparation.

Obviously, numerous modifications and variations of the present invention are possible in light of the above teachings. It is therefore to be understood that within the scope of the appended claims, the invention may be practiced otherwise that as specifically described herein.

What is claimed is:

1. A compound selected from:
    (i) N-((1R,2S,5R)-5-(methylamino)-2-((3S)-2-oxo-3-((6-(trifluoromethyl)-4-quinazolinyl)amino)-1-pyrrolidinyl)cyclohexyl)acetamide;
    N-((1R,2S,5R)-5-(isopropyl(methyl)amino)-2-((3S)-2-oxo-3-((6-(trifluoromethyl)-4-quinazolinyl)amino)-1-pyrrolidinyl)cyclohexyl)formamide;
    N-((1R,2S,5R)-5-(dimethylamino)-2-((3S)-2-oxo-3-((6-(trifluoromethyl)-4-quinazolinyl)amino)-1-pyrrolidinyl)cyclohexyl)acetamide;
    N-((1R,2S,5R)-5-amino-2-((3S)-2-oxo-3-((6-(trifluoromethyl)-4-quinazolinyl)amino)-1-pyrrolidinyl)cyclohexyl)propanamide; and
    N-(((1S,2S,5R)-5-methoxy-2-((3S)-2-oxo-3-((6-(trifluoromethyl)-4-quinazolinyl)amino)-1-pyrrolidinyl)cyclohexyl)methyl)acetamide; or
    (ii) a pharmaceutically acceptable salt of (i) thereof.

2. A compound that is N-((1R,2S,5R)-5-(methylamino)-2-((3S)-2-oxo-3-((6-(trifluoromethyl)-4-quinazolinyl)amino)-1-pyrrolidinyl)cyclohexyl)acetamide, or a pharmaceutically acceptable salt thereof.

3. A compound of claim 1 that is N-((1R,2S,5R)-5-(isopropyl(methyl)amino)-2-((3S)-2-oxo-3-((6-(trifluoromethyl)-4-quinazolinyl)amino)-1-pyrrolidinyl)cyclohexyl)formamide, or a pharmaceutically acceptable salt thereof.

4. A compound that is N-((1R,2S,5R)-5-(diniethylamino)-2-((3S)-2-oxo-3-((6-(trifluoromethyl)-4-quinazolinyl)amino)-1-pyrrolidinyl)cyclohexyl)acetamide, or a pharmaceutically acceptable salt thereof.

5. A compound of claim 1 that is N-((1R,2S,5R)-5-amino-2-((3S)-2-oxo-3-((6-(trifluoromethyl)-4-quinazolinyl)amino)-1-pyrrolidinyl)cyclohexyl)propanamide, or a pharmaceutically acceptable salt thereof.

6. A compound that is N-(((1S,2S,5R)-5-methoxy-2-((3S)-2-oxo-3-((6-(trifluoromethyl)-4-quinazolinyl)amino)-1-pyrrolidinyl)cyclohexyl)methyl)acetamide, or a pharmaceutically acceptable salt thereof.

7. A compound selected from:
    (i) N-((1R,2S,5R)-5-(isopropylamino)-2-((3S)-2-oxo-3-((6-(trifluoromethyl)-4-quinazolinyl)amino)-1-pyrrolidinyl)cyclohexyl)acetamide;
    N-((1R,2S,5R)-5-amino-2-((3S)-2-oxo-3-((6-(trifluoromethyl)-4-quinazolinyl)amino)-1-pyrrolidinyl)cyclohexyl)acetamide;
    N-((1R,2S,5R)-5-(isopropyl(methyl)amino)-2-((3S)-3-((1-oxido-6-(trifluoromethyl)-4-quinazolinyl)amino)-2-oxo-1-pyrrolidinyl)cyclohexyl)acetamide;
    N-((1R,2S,5R)-5-(isopropylamino)-2-((3S)-3-((1-oxido-6-(trifluoromethyl)-4-quinazolinyl)amino)-2-oxo-1-pyrrolidinyl)cyclohexyl)acetamide; and
    N-((1R,2S,5R)-5-(tert-butylamino)-2-((3S)-3-((1-oxido-6-(trifluoromethyl)-4-quinazolinyl)amino)-2-oxo-1-pyrrolidinyl)cyclohexyl)acetamide; or
    (ii) a pharmaceutically acceptable salt of (i) thereof.

8. A pharmaceutical composition comprising at least one compound according to claim 1 or claim 7, and a pharmaceutically acceptable carrier or diluent.

9. A pharmaceutical composition comprising at least one compound according to claim 2, and a pharmaceutically acceptable carrier or diluent.

10. A pharmaceutical composition comprising at least one compound according to claim 4, and a pharmaceutically acceptable carrier or diluent.

11. A pharmaceutical composition comprising at least one compound according to claim 6, and a pharmaceutically acceptable carrier or diluent.

* * * * *

UNITED STATES PATENT AND TRADEMARK OFFICE
CERTIFICATE OF CORRECTION

PATENT NO. : 7,687,508 B2 Page 1 of 1
APPLICATION NO. : 11/782810
DATED : March 30, 2010
INVENTOR(S) : Percy H. Carter et al.

It is certified that error appears in the above-identified patent and that said Letters Patent is hereby corrected as shown below:

On the Title Page Item (75) (Inventors)
Line 7, "Narbeth," should read -- Narberth, --.

Column 1
Line 4, Please insert the following heading under the title of the invention:
-- RELATED APPLICATIONS --.

Column 63
Line 32, "diniethylamino" should read -- dimethylamino --.

Signed and Sealed this

Second Day of November, 2010

David J. Kappos
*Director of the United States Patent and Trademark Office*